(12) United States Patent
Keung et al.

(10) Patent No.: US 9,598,424 B2
(45) Date of Patent: Mar. 21, 2017

(54) HETEROARYLAMIDE INHIBITORS OF TBK1

(71) Applicant: Takeda Pharmaceutical Company Limited, San Diego, CA (US)

(72) Inventors: Walter Keung, San Diego, CA (US);
Lily Kwok, San Diego, CA (US);
Mark Sabat, San Diego, CA (US);
Nicholas Scorah, San Diego, CA (US);
Haixia Wang, San Diego, CA (US);
Steven John Woodhead, San Diego, CA (US); Anthony R Gangloff, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/123,992

(22) PCT Filed: Feb. 12, 2015

(86) PCT No.: PCT/US2015/015651
§ 371 (c)(1),
(2) Date: Sep. 6, 2016

(87) PCT Pub. No.: WO2015/134171
PCT Pub. Date: Sep. 11, 2015

(65) Prior Publication Data
US 2017/0015669 A1 Jan. 19, 2017

Related U.S. Application Data

(60) Provisional application No. 61/949,026, filed on Mar. 6, 2014.

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC .............................. C07D 487/04; C07D 471/04
USPC .................................................... 514/210.18
See application file for complete search history.

(56) References Cited

FOREIGN PATENT DOCUMENTS

| WO | WO 2007/095588 | 8/2007 |
|----|---------------|--------|
| WO | WO 2009/010530 | 1/2009 |
| WO | WO 2009/155388 | 12/2009 |
| WO | WO 2010/100144 | 9/2010 |
| WO | WO 2014/004863 | 1/2014 |
| WO | WO 2005/107760 | 11/2014 |

OTHER PUBLICATIONS

"The International Search Report and the Written Opinion of the International Search Authority, or the Declaration" dated Mar. 26, 2015, International Patent Application No. PCT/US2015/015651.

*Primary Examiner* — Yevegeny Valenrod
(74) *Attorney, Agent, or Firm* — Matthew J. Russo; David M. Stemerick

(57) ABSTRACT

The present invention provides compounds of formula 1:

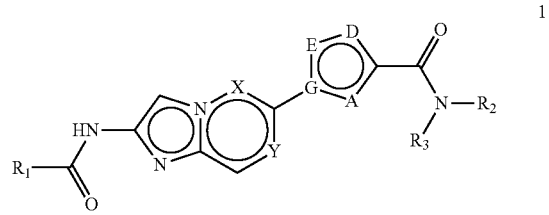

which are useful as inhibitors of TBK-1, pharmaceutical compositionst thereof, methods for treatment of conditions associated with TBK1, processes for making the compounds and intermediates thereof.

15 Claims, No Drawings

HETEROARYLAMIDE INHIBITORS OF TBK1

CROSS-REFERENCE TO RELATED APPLICATIONS

This application is the U.S. National Stage entry under 35 U.S.C. §371(c) of International Application PCT/US2015/015651, filed Feb. 12, 2015, which claims the benefit of U.S. Provisional Application No. 61/949,026, filed Mar. 6, 2014.

FIELD OF THE INVENTION

The present invention relates to medicinal chemistry, pharmacology, and medicine.

BACKGROUND OF THE INVENTION

TANK-binding kinase 1 (TBK1), also known NAK and T2K, has a role in innate immunity. TBK1 serves as an integrator of multiple signals induced by receptor-mediated pathogen detection and as a modulator of the levels of type I interferons. TBK1 is also activated by various growth factors.

Due to its central role in immunologic and inflammatory responses inhibitors of TBK1 are expected to provide benefit to patients suffering from septic shock, autoimmune diseases, chronic inflammation, and rejection of transplanted tissues. There is a need for treatment of such conditions and others described herein with compounds that are TBK-1 inhibitors. The present invention provides inhibitors of TBK1.

Certain inhibitors of PI3K are described in WO2010/100144, WO2007/095588, and WO2009/010530 and certain inhibitors of p38 kinase are described in WO2009/155388.

SUMMARY OF THE INVENTION

The present invention provides compounds of formula 1:

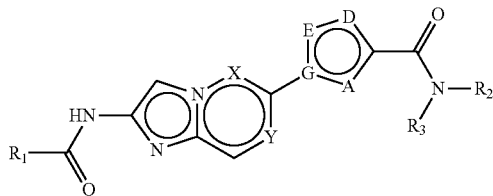

wherein
$R_1$ is selected from the group consisting of optionally substituted $C_{1-4}$ alkyl and optionally substituted $C_{3-8}$ cycloalkyl;
$R_2$ is selected from the group consisting of hydrogen and optionally substituted $C_{1-4}$ alkyl;
$R_3$ is selected from the group consisting of substituted $C_{1-6}$ alkyl, optionally substituted $C_{3-8}$ cycloalkyl, and optionally substituted $C_{3-6}$ heterocyclyl;
or
$R_2$ and $R_3$ together with the nitrogen to which they are attached form a 4 to 6 membered, saturated, ring optionally having an additional ring heteroatom selected from the group N, O, and S and optionally substituted on any ring carbon with 1 to 5 substituents independently selected from the group consisting of cyano, halo, hydroxy, amino, $C_{1-9}$ amide, $C_{1-4}$ alkyl, $C_{1-4}$ alkoxy, hydroxymethyl, and trifluoromethyl and optionally substituted on any optional additional ring nitrogen by optionally substituted $C_{1-4}$ alkyl;
X and Y are independently selected from the group consisting of N and $CR_4$;
$R_4$, each time taken, is independently selected from the group consisting of hydrogen, cyano, halo, hydroxy, $C_{1-2}$ alkyl, $C_{1-2}$ alkoxy, and trifluoromethyl;
G is carbon;
A is selected from the group consisting of N, O, S, $CR_5$ and $NR_6$;
D is selected from the group consisting of N, O, S, $CR_5$ and $NR_6$;
E is selected from the group consisting of N, O, S, $CR_5$ and $NR_6$;
provided that only one of A, D, and E can be O or S;
or G is N when A, D, and E are $CR_5$;
or G is N when one of A, D, or E is N and the others of A, D, and E are $CR_5$;
or G is N when two of A, D, or E are N and the other of A, D, and E is $CR_5$;
$R_5$, each time taken, is independently selected from the group consisting of hydrogen, cyano, halo, $C_{1-4}$ alkyl, $C_{1-4}$ alkoxy, and trifluoromethyl; and
$R_6$ is selected from the group consisting of hydrogen and $C_{1-4}$ alkyl;
or a pharmaceutically acceptable salt thereof.

The present invention also provides pharmaceutical compositions, comprising: a compound of formula 1 or a pharmaceutically acceptable salt thereof and a pharmaceutically acceptable excipient.

The compounds of the invention are inhibitors of TBK1 they are useful for the treatment of conditions associated with TBK1, including immunological disorders, such as autoimmune disorders, inflammatory disorders, fibrotic conditions, cancer, sepsis, and other disorders mentioned herein. Thus, the present invention provides for the use of the compounds of the invention as a medicament, including for the manufacture of a medicament. The present invention also provides methods of treating the conditions associated with TBK1, comprising: administering to a patient in need thereof an effective amount of the compounds of the invention.

The present invention also provides processes from making TBK1 inhibitors and intermediates thereof.

DETAILED DESCRIPTION OF THE INVENTION

The term "$C_{1-2}$ alkyl" refers to a methyl or ethyl.
The term "$C_{1-3}$ alkyl" refers to a straight or branched alkyl chain of one to three carbon atoms.
The term "$C_{1-4}$ alkyl" refers to a straight or branched alkyl chain of one to four carbon atoms.
The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{5-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

The term "$C_{2-4}$ alkyl" refers to a straight or branched alkyl chain of two to four carbon atoms, and included ethyl, propyl, butyl and the isomers of propyl and butyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{5-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-2}$ alkoxy" refers to a $C_{1-2}$ alkyl attached through an oxygen atom.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{5-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{5-10}$ aryl" refers to a monocyclic and polycyclic unsaturated, conjugated hydrocarbon having five to ten carbon atoms, and includes cyclopentyldienyl, phenyl, and naphthyl.

More particularly "$C_{5-10}$ aryl" refers to phenyl.

The term "optionally substituted $C_{5-10}$ aryl" refers to a $C_{5-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{5-10}$ aryl" refers to a $C_{5-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{5-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—CO$_2$H) and $C_{1-4}$ alkyl ester thereof.

The term "$C_{1-5}$ carbonyloxy" refers to a carbonyloxy group (—O$_2$CR$_f$), in which R$_f$ is selected from the group consisting of hydrogen and $C_{1-4}$ alkyl, for example, acetoxy.

The term "$C_{3-8}$ cycloalkyl" refers to an alkyl ring of three to eight carbon atoms, and includes cyclopropyl, cyclobutyl, cyclopentyl, cyclohexyl, and the like.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkyl, $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo atom.

The term "$C_{3-6}$ heterocyclyl" refers to a 4 to 8 membered monocyclic saturated or partially (but not fully) unsaturated ring having one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —SO$_2$—. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkyl, halo, hydroxy, nitro, oxo, and optionally substituted phenyl; and optionally substituted on any ring nitrogen with a substituent independently selected from the group consisting of optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidinyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-9}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pryidone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—$R_g$ group wherein $R_g$ is selected from the group consisting of $C_{1-6}$ alkyl and optionally substituted phenyl.

The term "aminosulfonyl" refers to a —S(O)$_2$NH$_2$.

The term "$C_{1-10}$ aminosulfonyl" refers to a —S(O)$_2$NR$_h$R$_i$ group wherein R$_h$ is selected from the group consisting of hydrogen and $C_{1-4}$ alkyl and R$_i$ is selected from the group consisting of $C_{1-4}$ alkyl, and optionally substituted phenyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, that the mentioned number refers to the mentioned group and does not include any carbons that may be present in any optional substituent(s) thereon.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the present invention exist as tautomers. All tautomeric forms the compounds of the invention are contemplated to be within the scope of the present invention.

Compounds of the invention also include all pharmaceutically acceptable isotopic variations, in which at least one atom is replaced by an atom having the same atomic number, but an atomic mass different from the predominant atomic mass. Use of isotopic variations (e.g., deuterium, $^2$H) may afford greater metabolic stability. Additionally, certain isotopic variations of the compounds of the invention may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies.

The terms "compounds of the invention" and "a compound of the invention" include the embodiment of formula 1 and the other more particular embodiments encompassed by formula 1 described herein and exemplified compounds described herein and a pharmaceutically acceptable salt of each of these embodiments.

It is understood that the feature:

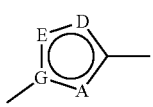

of formula 1 includes the divalent radicals depicted below:

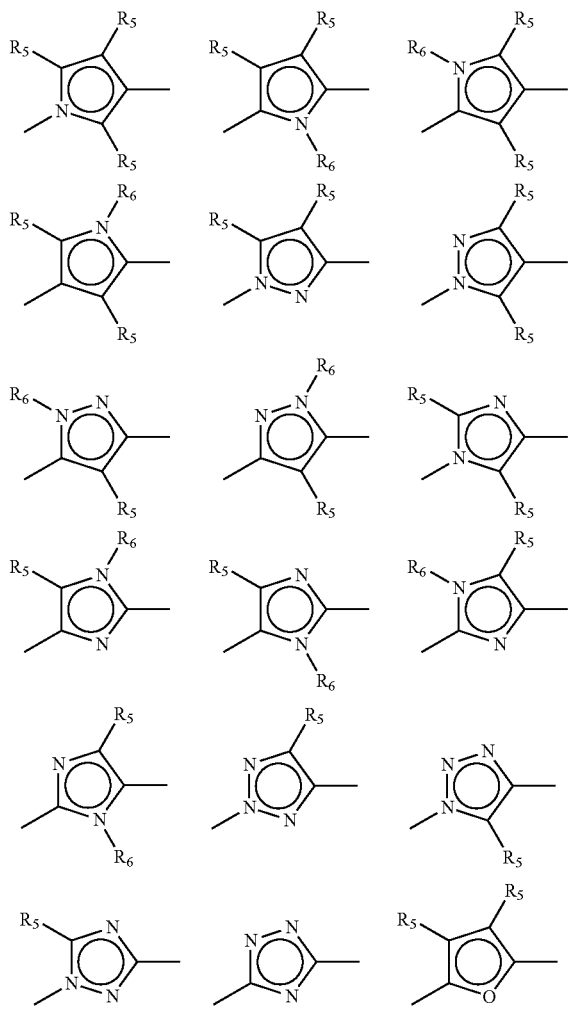

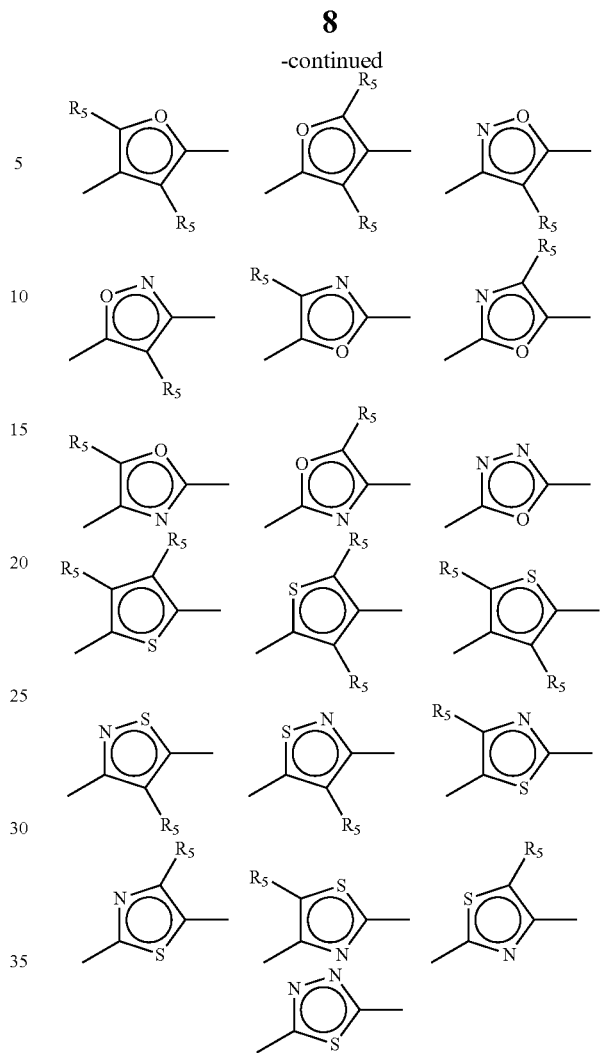

In $R_3$ the term "substituted $C_{1-6}$ alkyl" refers to a $C_{1-6}$ alkyl substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-5}$ oxycarbonyl, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{5-10}$ aryl; more particularly substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl; and even more particularly substituted with 1 to 7 substituents independently selected from the group consisting of optionally substituted $C_{3-8}$ cycloalkyl, halo, and optionally substituted $C_{3-6}$ heterocyclyl; and still more particularly substituted with 1 to 7 substituents independently selected from the group consisting of fluoro, $C_{3-8}$ cycloalkyl optionally substituted with 1 to 2 substituents selected from the group consisting of hydroxy, oxy, and, and $C_{3-6}$ heterocyclyl optionally substituted on carbon with 1 to 2 substituents selected from the group consisting of $C_{1-4}$ alkyl, $C_{1-4}$ alkoxy, halo, and hydroxy, and optionally substituted on any ring nitrogen with a $C_{1-4}$ alkyl.

In $R_3$ the term "optionally substituted $C_{3-8}$ cycloalkyl" more particularly refers to a $C_{3-8}$ cycloalkyl optionally substituted with 1 to 6 substituents independently selected from the group consisting of optionally substituted $C_{1-4}$ alkyl, $C_{1-4}$ alkoxy, halo, and hydroxy; even more particularly 1 to 6 substituents independently selected from the group consisting of $C_{1-4}$ alkyl, trifluoromethyl, $C_{1-4}$ alkoxy, halo, and hydroxy.

In $R_3$ the term "optionally substituted $C_{3-6}$ heterocyclyl" the $C_{3-6}$ heterocyclyl includes in particular azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl; more particularly, pyrrolidinyl, piperidinyl, piperazinyl, morpholinyl, oxetanyl, tetrahydropyranyl, tetrahydrothiopyranyl, and tetrahydrofuryl; and even more particularly pyrrolidinyl, piperidinyl, morpholinyl, and tetrahydrofuryl.

In $R_3$ the term "optionally substituted $C_{3-6}$ heterocyclyl" the optionally substituents more particularly include on the ring carbons with 1 to 4 substituents independently selected from the group consisting of optionally substituted $C_{1-4}$ alkyl, in particularly trifluoromethyl, $C_{1-4}$ alkoxy, cyano, $C_{3-8}$ cycloalkyl, halo, and hydroxy; and optionally substituted on any ring nitrogen with a substituent independently selected from the group consisting of $C_{1-4}$ alkyl and $C_{3-8}$ cycloalkyl.

When $R_2$ and $R_3$ are together with the nitrogen to which they are attached form a 4 to 6 membered, saturated, ring optionally having an additional ring heteroatom selected from the group N, O, and S it is understood to include in particular azetidinyl, pyrrolidinyl, piperidinyl, piperazinyl, morpholinyl, thiomorpholinyl, hexahydropyrimidinyl, tetrahydropyrimidinyl, and dihydroimidazolyl; more particularly, pyrrolidinyl, piperidinyl, piperazinyl, morpholinyl; and even more particularly pyrrolidinyl and piperidinyl. To be completely clear, each of the specifically mentioned rings above are optionally substituted on any ring carbon with 1 to 5 substituents independently selected from the group consisting of cyano, halo, hydroxy, amino, $C_{1-6}$ alkyl, $C_{1-4}$ alkoxy, and trifluoromethyl and optionally substituted on any optional additional ring nitrogen by optionally substituted $C_{1-4}$ alkyl.

The present invention also includes intermediates of the formulae 2 and 3

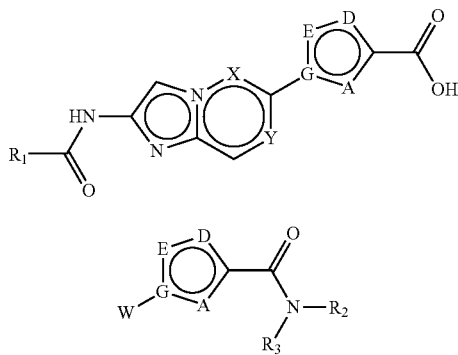

wherein X, Y, $R_1$, $R_2$, $R_3$, A, D, E, and G are as defined for formula 1 and W is hydrogen when G is N and W is halo when G is carbon.

Further embodiments of compounds of the invention are provided below:

(a) One embodiment relates to compounds of formula 1 and compounds of formula 3 wherein $R_3$ is substituted $C_{1-6}$ alkyl.

(b) One embodiment relates to compounds of formula 1 and compounds of formula 3 wherein $R_3$ is substituted $C_{1-6}$ alkyl substituted with 1 to 7 substituents independently selected from the group consisting of $C_{1-4}$ alkoxy, cyano, $C_{3-8}$ cycloalkyl, halo, hydroxy, and $C_{3-6}$ heterocyclyl.

(c) One embodiment relates to compounds of formula 1 and compounds of formula 3 wherein $R_3$ is substituted $C_{1-6}$ alkyl substituted with 1 to 7 substituents independently selected from the group consisting of optionally substituted $C_{3-8}$ cycloalkyl, halo, and optionally substituted $C_{3-6}$ heterocyclyl.

(d) One embodiment relates to compounds of formula 1 and compounds of formula 3 wherein $R_3$ is substituted $C_{1-6}$ alkyl substituted with 1 to 7 substituents independently selected from the group consisting of fluoro, $C_{3-8}$ cycloalkyl, and $C_{3-6}$ heterocyclyl.

(e) One embodiment relates to compounds of formula 1 and compounds of formula 3 wherein $R_3$ is $C_{1-6}$ alkyl substituted with 1 to 6 fluorines. One embodiment relates to compounds of formula 1 and compounds of formula 3 wherein $R_3$ is $C_{1-4}$ alkyl substituted with 1 to 6 fluorines.

(f) One embodiment relates to compounds of formula 1 and compounds of formula 3 wherein $R_3$ is selected from the group consisting of 2-fluoroethyl, 2,2-difluoroethyl, 2,2,2-trifluoroethyl, 1-methyl-2,2,2-trifluoroethyl, 3-fluoropropyl, 2,2-difluoropropyl, and 3,3,3-trifluoropropyl. A further embodiment relates to compounds of formula 1 and compounds of formula 3 wherein $R_3$ is 2,2,2-trifluoroethyl.

(g) One embodiment relates to compounds of formula 1 and compounds of formula 3 wherein $R_3$ is optionally substituted $C_{3-8}$ cycloalkyl.

(h) One embodiment relates to compounds of formula 1 and compounds of formula 3 wherein $R_3$ is optionally substituted $C_{3-8}$ cycloalkyl substituted with 1 to 6 substituents independently selected from the group consisting of optionally substituted $C_{1-4}$ alkyl, $C_{1-4}$ alkoxy, halo, and hydroxy.

(i) One embodiment relates to compounds of formula 1 and compounds of formula 3 wherein $R_3$ is optionally substituted $C_{3-8}$ cycloalkyl substituted with 1 to 6 substituents independently selected from the group consisting of $C_{1-4}$ alkyl, trifluoromethyl, $C_{1-4}$ alkoxy, halo, and hydroxy.

(j) One embodiment relates to compounds of formula 1 and compounds of formula 3 wherein $R_3$ is optionally substituted $C_{3-6}$ heterocyclyl wherein the $C_{3-6}$ heterocyclyl is selected from the group consisting of azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl; each optionally substituted on the ring carbons with 1 to 4 substituents independently selected from the group consisting of optionally substituted $C_{1-4}$ alkyl, in particularly trifluoromethyl, $C_{1-4}$ alkoxy, cyano, $C_{3-8}$ cycloalkyl, halo, and hydroxy; and optionally substituted on any ring nitrogen with a substituent independently selected from the group consisting of $C_{1-4}$ alkyl and $C_{3-8}$ cycloalkyl.

(k) One embodiment relates to compounds of formula 1 and compounds of formula 3 wherein $R_3$ is optionally substituted $C_{3-6}$ heterocyclyl wherein the $C_{3-6}$ heterocyclyl is selected from the group consisting of pyrrolidinyl, piperidinyl, morpholinyl, tetrahydropyranyl, and tetrahydrofuryl;

each optionally substituted on the ring carbons with 1 to 4 substituents independently selected from the group consisting of optionally substituted $C_{1-4}$ alkyl, in particularly trifluoromethyl, $C_{1-4}$ alkoxy, cyano, $C_{3-8}$ cycloalkyl, halo, and hydroxy; and optionally substituted on any ring nitrogen with a substituent independently selected from the group consisting of $C_{1-4}$ alkyl and $C_{3-8}$ cycloalkyl.

(l) One embodiment relates to compounds of formula 1 and compounds of formula 3 wherein $R_3$ is pyrrolidinyl optionally substituted on the ring carbons with 1 to 4 substituents independently selected from the group consisting of $C_{1-4}$ alkyl, trifluoromethyl, $C_{1-4}$ alkoxy, halo, and hydroxy.

(m) One embodiment relates to compounds of formula 1 and compounds of formula 3 wherein $R_3$ is tetrahydrofuryl optionally substituted with 1 to 4 substituents independently selected from the group consisting of $C_{1-4}$ alkyl, $C_{1-4}$ alkoxy, halo, and hydroxy.

(n) One embodiment relates to compounds of formula 1 and compounds of formula 3 and embodiments (a), (b), (c), (d), (e), (f), (g), (h), (i), (j), (k), (l), and (m) wherein $R_2$ is selected from the group consisting of hydrogen and optionally substituted $C_{1-4}$ alkyl.

(o) One embodiment relates to compounds of formula 1 and compounds of formula 3 and embodiments (a), (b), (c), (d), (e), (f), (g), (h), (i), (j), (k), (l), and (m) wherein $R_2$ is hydrogen. A further embodiment relates to compounds of formula 1 and compounds of formula 3 and embodiments (a), (b), (c), (d), (e), (f), (g), (h), (i), (j), (k), (l), and (m) wherein $R_2$ is $C_{2-4}$ alkyl optionally substituted with 1 or 2 hydroxyl. In yet a further embodiment relates to compounds of formula 1 and compounds of formula 3 and embodiments (a), (b), (c), (d), (e), (f), (g), (h), (i), (j), (k), (l), and (m) wherein $R_2$ is optionally substituted $C_{1-4}$ alkyl. One embodiment relates to compounds of formula 1 and compounds of formula 3 and embodiments (a), (b), (c), (d), (e), (f), (g), (h), (i), (j), (k), (l), and (m) wherein $R_2$ is selected from the group consisting of hydrogen and $C_{2-4}$ alkyl optionally substituted with 1 or 2 hydroxyl.

(p) One embodiment relates to compounds of formula 1 and compounds of formula 3 wherein $R_2$ and $R_3$ are together with the nitrogen to which they are attached form a 4 to 6 membered, saturated, ring optionally having an additional ring heteroatom selected from the group N, O, and S selected from the group consisting of azetidinyl, pyrrolidinyl, piperidinyl, piperazinyl, morpholinyl, thiomorpholinyl, hexahydropyrimidinyl, tetrahydropyrimidinyl, and dihydroimidazolyl; each optionally substituted on any carbon with 1 to 5 substituents independently selected from the group consisting of cyano, halo, hydroxy, amino, $C_{1-6}$ alkyl, $C_{1-4}$ alkoxy, and trifluoromethyl.

(q) One embodiment relates to compounds of formula 1 and compounds of formula 3 wherein $R_2$ and $R_3$ are together with the nitrogen to which they are attached form a 4 to 6 membered, saturated, ring optionally having an additional ring heteroatom selected from the group N, O, and S selected from the group consisting of pyrrolidinyl and piperidinyl; each optionally substituted on any carbon with 1 to 5 substituents independently selected from the group consisting of cyano, halo, hydroxy, amino, $C_{1-6}$ alkyl, $C_{1-4}$ alkoxy, and trifluoromethyl.

(r) Another embodiment relates to compounds of formula 1 and compounds of formula 2 and embodiments (a), (b), (c), (d), (e), (f), (g), (h), (i), (j), (k), (l), (m), (n), (o), (p), and (q) wherein $R_1$ is $C_{3-8}$ cycloalkyl.

(s) Another embodiment relates to compounds of formula 1 and compounds of formula 2 and embodiments (a), (b), (c), (d), (e), (f), (g), (h), (i), (j), (k), (l), (m), (n), (o), (p), and (q) wherein $R_1$ is cyclopropyl.

(t) Another embodiment relates to compounds of formula 1 and compounds of formula 2 and compounds of formula 3 and embodiments (a), (b), (c), (d), (e), (f), (g), (h), (i), (j), (k), (l), (m), (n), (o), (p), (q), (r), and (s) wherein A is $CR_5$, D is S, E is $CR_5$, and G is carbon.

(u) Another embodiment relates to compounds of formula 1 and compounds of formula 2 and compounds of formula 3 and embodiments (a), (b), (c), (d), (e), (f), (g), (h), (i), (j), (k), (l), (m), (n), (o), (p), (q), (r), and (s) wherein A is $CR_5$, D is $NR_6$, E is N, and G is carbon.

(v) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein A is $CR_5$; D is N, E is $NR_6$; and G is carbon.

(w) Another embodiment relates to compounds of formula 1 and compounds of formula 2 and compound of formula 3 and embodiments (a), (b), (c), (d), (e), (f), (g), (h), (i), (j), (k), (l), (m), (n), (o), (p), (q), (r), and (s) wherein A is N, D is S, E is $CR_5$, and G is carbon.

(x) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G is N when A, D, and E are $CR_5$.

(y) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G is N, A is N, and D and E are $CR_5$.

(z) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G is N, D is N, and A and E are $CR_5$.

(aa) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G is N, E is N, and A and D are $CR_5$.

(ab) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G, A, and D are N and E is $CR_5$.

(ac) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G, A, and E are N and D is $CR_5$.

(ad) Another embodiment relates to compounds of formula 1 and compounds of formula 3 and embodiments (a), (b), (c), (d), (e), (f), (g), (h), (i), (j), (k), (l), (m), (n), (o), (p), (q), (r), and (s) wherein G, E, and D are N and A is $CR_5$.

(ae) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein X and Y are $CR_4$.

(af) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein X and Y are $CR_4$ and each $R_4$ is hydrogen.

(ag) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein X is N and Y is $CR_4$.

(ah) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein X is N and Y is $CR_4$ and $R_4$ is hydrogen.

(ai) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein Y is N and X is $CR_4$.

(aj) Another embodiment relates to compounds of formula 1 and compounds of formula 2 and embodiments (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), and (ad) wherein Y is N and X is $CR_4$ and $R_4$ is hydrogen.

(ay) Another embodiment relates to a pharmaceutically acceptable salt of each of the above embodiments.

(az) Another embodiment relates to a pharmaceutically acceptable salt of each of the exemplified compounds.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991).

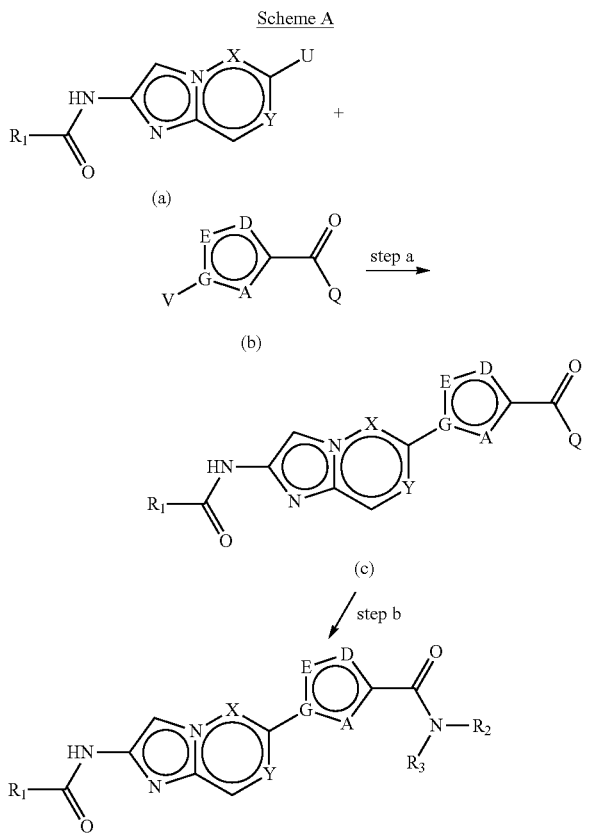

Scheme A, step a, the coupling of an appropriate compound of formula (a) and an appropriate compound of formula (b) to give a compound of formula (c). An appropriate compound of formula (a) is one in which $R_1$, X, and Y are as desired in the final compound of formula 1 and U is a boronic acid or boronic ester or a leaving group, such as halo. An appropriate compound of formula (b) is one in which A, D, E, and G are as desired in the final product of formula 1, Q is $-NR_2R_3$ as desired in the final product of formula 1, or a group that gives rise to $-NR_2R_3$ as desired in the final product of formula 1, as will be discussed in step b, and V is a boronic acid or boronic ester, a leaving group, such as halo, or hydrogen.

Where G is carbon, typically, either one of U or V is boronic acid or boronic ester residue and the other is a leaving group, such as halo, in particular bromo or iodo and Scheme A, step 1, depicts a metal catalyzed carbon-carbon bond forming reactions such as the Suzuki coupling, which are very well known in the art. Other aryl-aryl coupling reactions may be employed using compound having U or V other than boronic acids or esters.

Where G is N, typically U is a leaving group, such as halo and V is hydrogen and Scheme A, step 1, depicts an Ullmann-type reaction. Such reactions are well understood and appreciated. For example, such a reaction is generally carried out in a solvent, such as DMSO, THF, DMF, DMA, and the like. The reaction is carried out with the use of a suitable base, such as alkali metal hydroxides, such as sodium hydroxide, and alkali metal alkoxides, such as sodium alkoxides and potassium alkoxides, alkali metal carbonates, such as sodium carbonate and potassium carbonate and amine bases, such diisopropylethylamine (DIPEA), triethylamine and the like. The reaction may be carried out in the presence of a catalyst, such as copper catalysts. The reaction is typically carried out at temperatures of from 0° C. to 100° C. The reaction typically requires 1 to 72 hours.

Scheme A, step b, depicts the conversions of a compound of formula (c) in which Q gives rise to $-NR_2R_3$ to a desired final product of formula 1. Typical groups Q that are suitable for this purpose is $-OH$ of a carboxylic acid or $-OR$ in which R is methyl, ethyl, t-butyl, or optionally substituted benzyl. Of course, it is understood that under some circumstances a compound of formula (c) in which Q is $-OR$ can be used directly, but that such compounds can also be hydrolyzed to the carboxylic acid in which Q is $-OH$. Using a compound of formula (c) in which Q is $-OH$ or $-OR$, Scheme A, step b, depicts an amidation reaction to give a compound of formula 1. Such amide forming reactions are well understood and appreciated in the art.

It will be recognized by one of ordinary skill in the art that a compound of formula (a), (b), (c) or formula 1 can be elaborated in a variety of ways to give compounds of formula 1. Such reactions include hydrolysis, oxidation, reduction, alkylation, amidations, sulfonations, and the like.

Also, in an optional step, not shown, the compounds of formula 1 can be converted to pharmaceutically acceptable salts by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d6 (deuterodimethylsulfoxide), CD$_3$OD (deuteromethanol), and THF-d8 (deuterotetrahydrofuran). The mass spectra were recorded using either electrospray ionization (ESI) or atmospheric pressure chemical ionization.

The examples below were carried out in appropriate vessels and were typically stirred. Where indicated, products of certain preparations and examples are purified by mass-triggered HPLC (e.g., Pump: Waters™ 2525; MS: ZQ™; Software: MassLynx™), flash chromatography, or preparative thin layer chromatography (TLC). Reverse phase chromatography can be carried out using a variety of systems, including on a column (Gemini™ 5μ C18 110A, Axia™, ID30×75 mm, 5μ) under acidic conditions, eluting with acetonitrile (ACN) and water mobile phases containing 0.035% and 0.05% trifluoroacetic acid (TFA), respectively, or 0.1% formic acid (FA) in 20/80 (v/v) water/methanol or under basic conditions, eluting with water and 20/80 (v/v) water/acetonitrile mobile phases, both containing 10 mM NH$_4$HCO$_3$; or (XSelect™ C18, 5μ, ID30×75 mm) under acidic conditions, eluting with ACN and water mobile phases containing 0.1% FA or under basic conditions, eluting with 0.1% ammonium hydroxide in water (pH=9.5-10) and 0.1% ammonium hydroxide in ACN (pH=9.5-10). After isolation by chromatography, the solvent is removed and the product is obtained by evaporating product containing fractions (e.g., GeneVac™), rotary evaporator, evacuated flask, lyophilization, etc.

Preparation 1 N-(2-bromoacetyl)cyclopropanecarboxamide

Combined cyclopropanecarboxamide (5.0 g, 58.8 mmol) and 2-bromoacetyl bromide (5.10 mL, 58.8 mmol) in dioxane (120 mL) and stirred at 60° C. for 4 h. The reaction was concentrated in vacuo and the residue was treated with saturated aqueous NaHCO$_3$ (50 mL). The resulting solid was isolated by filtration, washed with water and dried in vacuo to give the title compound (54.6% yield) as an off-white solid. $^1$H NMR (400 MHz, DMSO-d$_6$) δ ppm 0.82-0.95 (m, 4 H) 1.99-2.09 (m, 1 H) 4.34 (s, 2 H) 11.28 (br. s., 1 H); ESI-MS: m/z 206.0 [M+H]$^+$.

Preparation 2 N-(6-bromoimidazo[1,2-a]pyridin-2-yl)cyclopropanecarboxamide

Combined 5-bromopyridin-2-amine (4.20 g, 24.27 mmol) and N-(2-bromoacetyl)cyclopropanecarboxamide (5.0 g, 24.27 mmol) and DMA (48.5 ml) followed by sodium phosphate, dibasic (10.33 g, 72.8 mmol) and stirred at 80° C. for 18 h. The mixture was cooled and poured over ice. The resulting solid was isolated by filtration, washed with water and dried in vacuo to give the title compound (52.7% yield) as a brown solid. $^1$H NMR (400 MHz, DMSO-d$_6$) δ ppm 0.76-0.83 (m, 4 H) 1.89-1.98 (m, 1 H) 7.27-7.34 (m, 1 H) 7.37-7.44 (m, 1 H) 8.06 (s, 1 H) 8.87 (d, J=1.26 Hz, 1 H) 11.03 (s, 1 H); ESI-MS: m/z 280.1 [M+H]$^+$.

Preparation 3 4-(2-(cyclopropanecarboxamido)imidazo[1,2-a]pyridin-6-yl)thiophene-2-carboxylic acid Combined N-(6-bromoimidazo[1,2-a]pyridin-2-yl)cyclopropanecarboxamide (0.4 g, 1.428 mmol), (5-(methoxycarbonyl)thiophen-3-yl)boronic acid (0.292 g, 1.571 mmol), [1,1'-bis(diphenylphosphino)ferrocene]-dichloropalladium (II) (0.104 g, 0.143 mmol), dioxane (6.35 ml) and aqueous saturated sodium bicarbonate solution (3.17 ml). The resulting mixture was irradiated in a microwave at 120° C., 30 mins, high absorbance then diluted the reaction mixture with ethyl acetate, 25 mL and sonicated for 5 mins, then transferred to a separatory funnel and separated the layers. The aqueous layer was extracted with ethyl acetate (2×10 mL). Combined all organic layers and filtered through a pad of Celite® then rinsed with ethyl acetate. Combined all organics and concentrated to get a reddish brown residue. Added ethyl acetate (2 mL), sonicated then added ether, 10 mL, to slurry crude product then filtered to get methyl 4-(2-(cyclopropanecarboxamido)imidazo[1,2-a]pyridin-6-yl)thiophene-2-carboxylate (61.5% yield) as a brown solid. ESI-MS m/z 342.2 [M+H]$^+$.

Methyl 4-(2-(cyclopropanecarboxamido)imidazo[1,2-a]pyridin-6-yl)thiophene-2-carboxylate (1.2 g, 3.52 mmol) was dissolved in dioxane (14.06 ml) and treated with LiOH, 1 M (14.06 ml, 14.06 mmol). The mixture was stirred at room temperature for several hours. The reaction was concentrated to about half initial volume to remove dioxane. The aqueous layer was washed with ether (2×10 mL) and the ether was discarded. The aqueous layer as acidified to about pH 1-2 with 1N HCl. The resulting solid was isolated by filtration, washed with water and dried in vacuo to give the title compound (96% yield) as a dark brown solid. ESI-MS: m/z 328.2 [M+H]$^+$.

Preparation 4 3-(2-(cyclopropanecarboxamido)imidazo[1,2-a]pyridin-6-yl)-1-methyl-1H-pyrazole-5-carboxylic acid Combined N-(6-bromoimidazo[1,2-a]pyridin-2-yl)cyclopropanecarboxamide (300 mg, 1.071 mmol), methyl 1-methyl-3-(4,4,5,5-tetramethyl-1,3,2-dioxaborolan-2-yl)-1H-pyrazole-5-carboxylate (285 mg, 1.071 mmol) and [1,1'-bis(diphenylphosphino)ferrocene]dichloropalladium(II), complex with dichloromethane (88 mg, 0.107 mmol) in dioxane (8.0 mL) followed by sodium carbonate (2M, 2.142 mL, 4.28 mmol) and stirred at 125° C. for 30 min (normal absorbance) in the microwave. The crude material was diluted with MeOH (20 mL) and filtered. The filtrate was concentrated in vacuo to give methyl 3-(2-(cyclopropanecarboxamido)imidazo[1,2-a]pyridin-6-yl)-1-methyl-1H-pyrazole-5-carboxylate as a brown solid. ESI-MS: m/z 340.3 [M+H]$^+$.

Combined methyl 3-(2-(cyclopropanecarboxamido)imidazo[1,2-a]pyridin-6-yl)-1-methyl-1H-pyrazole-5-carboxylate (363 mg, 1.070 mmol) and lithium hydroxide (3.0 ml, 3.00 mmol) in dioxane (5.0 mL) and stirred at 23° C. for 1 h. The mixture was filtered and concentrated in vacuo. The residue was treated with 1M HCl (3.0 mL) taken up in MeOH and filtered then concentrated in vacuo to give 3-(2-(cyclopropanecarboxamido)imidazo[1,2-a]pyridin-6-yl)-1-methyl-1H-pyrazole-5-carboxylic acid (100% yield) as a brown solid. ESI-MS: m/z 326.3 [M+H]$^+$.

Preparation 5 N-(6-bromoimidazo[1,2-a]pyridin-2-yl)-2-methoxyacetamide

Combined 6-bromoimidazo[1,2-a]pyridin-2-amine (212 mg, 1.000 mmol) and potassium acetate (196 mg, 2.000 mmol) in DCM (4.0 mL) followed by 2-methoxyacetyl chloride (0.100 mL, 1.100 mmol) and stirred at 23° C. for 1 h. The reaction was concentrated in vacuo and the residue was taken up in water. The resulting solid was isolated by filtration, washed with water and dried in vacuo to give the title compound (57.7% yield) as a brown solid. $^1$H NMR (400 MHz, DMSO-d$_6$) δ ppm 3.35 (s, 3 H) 4.06 (s, 2 H) 7.33 (dd, J=9.47, 1.89 Hz, 1 H) 7.38-7.45 (m, 1 H) 8.15 (s, 1 H) 8.90 (d, J=1.26 Hz, 1 H) 10.51 (s, 1 H); ESI-MS: m/z 284.1 [M+H]$^+$.

Preparation 6 N-(6-bromoimidazo[1,2-a]pyridin-2-yl)-3-methoxypropanamide

Prepared by the methodology of Preparation 5 to give the title compound (48.3% yield) as a brown solid. $^1$H NMR (400 MHz, DMSO-d$_6$) δ ppm 2.60 (t, J=6.19 Hz, 2 H) 3.23

(s, 3 H) 3.61 (t, J=6.19 Hz, 2 H) 7.27-7.45 (m, 2 H) 8.11 (s, 1 H) 8.89 (d, J=1.26 Hz, 1 H) 10.76 (s, 1 H); ESI-MS: m/z 298.2 [M+H]$^+$.

Preparation 7 4-bromo-N-(1,1,1-trifluoropropan-2-yl)-1H-imidazole-2-carboxamide

Combined 4-bromo-1H-imidazole-2-carboxylic acid (215 mg, 1.123 mmol), 1,1,1-trifluoropropan-2-amine hydrochloride (168 mg, 1.123 mmol), and EDC (209 mg, 1.348 mmol) and HOBT (182 mg, 1.348 mmol) in DMF (5.0 ml) followed by N-methylmorpholine (0.988 ml, 8.99 mmol) and stirred at 23° C. for 2 h. The mixture was poured onto cold water (20 mL). The aq layer was extracted with EtOAc and the organic layer was washed with saturated aqueous NaHCO$_3$ and brine, then dried (MgSO$_4$) and concentrated in vacuo. The reaction mixture was purified by prep HPLC 25-50% ACN in water (0.1% FA) to give the title compound (36.7% yield) as a white solid. $^1$H NMR (400 MHz, DMSO-d$_6$) δ ppm 1.36 (d, J=7.07 Hz, 3 H) 4.76 (dd, J=15.79, 7.96 Hz, 1 H) 7.52 (s, 1 H) 9.13 (d, J=9.09 Hz, 1 H) 13.60 (br. s., 1 H); ESI-MS: m/z 286.1 [M+H]$^+$.

Preparation 8 N-(2,2-difluoroethyl)-4-(4,4,5,5-tetramethyl-1,3,2-dioxaborolan-2-yl)thiophene-2-carboxamide Prepared by the methodology of Preparation 7 to give the title compound (28.8% yield) as a white solid. $^1$H NMR (400 MHz, DMSO-d$_6$) δ ppm 1.29 (s, 12 H) 3.54-3.70 (m, 2 H) 5.91-6.27 (m, 1 H) 8.06 (s, 1 H) 8.18 (d, J=0.76 Hz, 1 H) 8.93 (t, J=5.68 Hz, 1 H); ESI-MS: m/z 318.2 [M+H]$^+$.

Preparation 9 N-(2,2,2-trifluoroethyl)-1H-pyrazole-3-carboxamide

Prepared by the methodology of Preparation 7 to give the title compound (36.8% yield) as a white solid. $^1$H NMR (400 MHz, DMSO-d$_6$) δ ppm 3.91-4.10 (m, 2 H) 6.72 (br. s., 1 H) 7.84 (br. s.) 8.73 (br. s., 1 H) 13.36 (br. s., 1 H); ESI-MS: m/z 194.1 [M+H]$^+$.

Preparation 10 N-(6-bromoimidazo[1,2-a]pyridin-2-yl)-2-cyanoacetamide

Prepared by the methodology of Preparation 5 to give the title compound (28.7% yield) as a tan solid. $^1$H NMR (400 MHz, DMSO-d$_6$) δ ppm 3.96 (s, 2 H) 7.31-7.48 (m, 2 H) 8.11 (s, 1 H) 8.92 (d, J=1.01 Hz, 1 H) 11.16 (s, 1 H); ESI-MS: m/z 279.1 [M+H]$^+$.

Preparation 11 (2-(cyclopropanecarboxamido)imidazo[1,2-a]pyridin-6-yl)boronic acid Combined (4,4,5,5-tetramethyl-1,3,2-dioxaborolan-2-yl)pyridin-2-amine (4.467 g, 20.30 mmol) and N-(2-bromoacetyl)cyclopropanecarboxamide (5.02 g, 24.36 mmol) in DMA (40.6 ml) followed by sodium phosphate, dibasic (8.64 g, 60.9 mmol) and stirred at 80° C. for 18 h. The reaction mixture was filtered and purified by prep HPLC 5-20% ACN in water (0.1% FA) to give the title compound (26.1% yield) as a yellow solid. $^1$H NMR (400 MHz, DMSO-d$_6$) δ ppm 0.74-0.85 (m, 4 H) 1.88-1.98 (m, 1 H) 7.34 (d, J=9.09 Hz, 1 H) 7.50 (d, J=8.84 Hz, 1 H) 7.98 (s, 1 H) 8.20 (s, 2 H) 8.72 (s, 1 H) 10.94 (s, 1 H); ESI-MS: m/z 246.2 [M+H]$^+$.

Preparation 12 5-bromo-4-methyl-N-(2,2,2-trifluoroethyl)-1H-pyrazole-3-carboxamide Combined 2,2,2-trifluoroethanamine hydrochloride (126 mg, 0.927 mmol), 5-bromo-4-methyl-1H-pyrazole-3-carboxylic acid (190 mg, 0.927 mmol), and EDC (173 mg, 1.112 mmol) and HOBT (150 mg, 1.112 mmol) in DMF (5.0 mL) followed by N-methylmorpholine (0.509 mL, 4.63 mmol) and stirred at 23° C. for 4 h. The reaction was diluted with cold water. The aqueous mixture was extracted with EtOAc, washed with brine then dried (MgSO$_4$) and concentrated in vacuo to give the title compound (64.5% yield) as a yellow solid. $^1$H NMR (400 MHz, DMSO-d$_6$) δ ppm 2.14 (s, 3 H) 2.89 (s, 2 H) 7.95 (s, 1 H) 8.69 (br. s., 1 H); ESI-MS: m/z 286.1 [M+H]$^+$.

Preparation 13 N-(2,2-difluoroethyl)-1H-pyrazole-3-carboxamide

Prepared by the methodology of 7 to give the title compound (50.9% yield) as a white solid. $^1$H NMR (400 MHz, DMSO-d$_6$) δ ppm 3.61 (tdd, J=15.28, 15.28, 5.94, 4.42 Hz, 2 H) 5.92-6.26 (m, 1 H) 6.66 (t, J=2.02 Hz, 1 H) 7.84 (s, 1 H) 8.43 (t, J=5.94 Hz, 1 H) 13.31 (br. s., 1 H); ESI-MS: m/z 176.0 [M+H]$^+$.

Preparation 14 5-bromo-N-(2,2,2-trifluoroethyl)thiazole-2-carboxamide

Combined 2,2,2-trifluoroethanamine hydrochloride (135 mg, 1.000 mmol), 5-bromothiazole-2-carboxylic acid (208 mg, 1.000 mmol), and EDC (186 mg, 1.200 mmol) and HOBT (162 mg, 1.200 mmol) in DMF (5.0 mL) followed by N-methylmorpholine (0.550 mL, 5.00 mmol) and stirred at 23° C. for 18 h. The reaction was diluted with ice water and the resulting solid was isolated by filtration, washed with water and dried in vacuo to give the title compound (57.1% yield) as a tan solid. $^1$H NMR (400 MHz, DMSO-d$_6$) δ ppm 3.95-4.11 (m, 2 H) 8.19 (s, 1 H) 9.55 (t, J=6.44 Hz, 1 H); ESI-MS: m/z 289.1 [M+H]$^+$.

Preparation 15 N-(6-bromoimidazo[1,2-a]pyridin-2-yl)-2-fluoroacetamide

Prepared by the methodology of Preparation 5 to give the title compound (68.0% yield) as a brown solid. $^1$H NMR (400 MHz, DMSO-d$_6$) δ ppm 4.93-5.14 (m, 2 H) 7.28-7.50 (m, 2 H) 8.17 (s, 1 H) 8.91 (d, J=1.26 Hz, 1 H) 10.96 (s, 1 H); ESI-MS: m/z 272.1 [M+H]$^+$.

Preparation 16 N-(6-bromoimidazo[1,2-a]pyrazin-2-yl)cyclopropanecarboxamide

Combined 5-bromopyrazin-2-amine (1.0 g, 5.75 mmol) and N-(2-bromoacetyl)cyclopropanecarboxamide (1.184 g, 5.75 mmol) and DMA (11.49 ml) followed by sodium phosphate, dibasic (2.448 g, 17.24 mmol) and stirred at 80° C. for 6 h. The mixture was cooled and poured over ice. The resulting solid was isolated by filtration, washed with water and dried in vacuo to give the title compound (26.4% yield) as a brown solid. $^1$H NMR (400 MHz, DMSO-d$_6$) δ ppm 0.84 (d, J=6.06 Hz, 4 H) 1.95 (quin, J=6.13 Hz, 1 H) 8.26 (s, 1 H) 8.74 (s, 1 H) 8.93 (d, J=1.01 Hz, 1 H) 11.35 (s, 1 H); ESI-MS: m/z 281.1 [M+H]$^+$.

Preparation 17 4-(2-(cyclopropanecarboxamido)imidazo[1,2-b]pyridazin-6-yl)thiazole-2-carboxylic acid Combined N-(6-iodoimidazo[1,2-b]pyridazin-2-yl)cyclopropanecarboxamide (50 mg, 0.152 mmol), methyl 4-(4,4,5,5-tetramethyl-1,3,2-dioxaborolan-2-yl)thiazole-2-carboxylate (41.0 mg, 0.152 mmol) and [1,1'-bis(diphenylphosphino)ferrocene]dichloropalladium(II), complex with dichloromethane (12.54 mg, 0.015 mmol) in dioxane (2.0 mL) followed by aqueous sodium carbonate (2.0 M, 0.305 mL, 0.610 mmol) and stirred at 120° C. for 30 min (normal absorbance) in the microwave. The reaction mixture was filtered and the crude material was purified by prep HPLC 20-45% ACN in water (0.1 FA) to give the title compound (43.8% yield) as a white solid. $^1$H NMR (400 MHz, DMSO-d$_6$) δ ppm 0.80-0.90 (m, 4 H) 1.97 (t, J=4.93 Hz, 1 H) 7.89 (d, J=9.35 Hz, 1 H) 8.12 (d, J=9.60 Hz, 1 H) 8.28 (s, 1 H) 8.72 (s, 1 H) 11.27 (s, 1 H); ESI-MS: m/z 330.3 [M+H]$^+$.

Preparation 18 4-(2-(cyclopropanecarboxamido)imidazo[1,2-a]pyrazin-6-yl)thiazole-2-carboxylic acid Prepared by the methodology of 17 to give the title compound (3% yield) as a light yellow solid. $^1$H NMR (400 MHz, DMSO-d$_6$) δ ppm 0.80-0.89 (m, 4 H) 1.97 (t, J=5.68

Hz, 1 H) 8.42 (s, 1 H) 8.46 (s, 1 H) 8.96 (s, 1 H) 9.29 (d, J=1.01 Hz, 1 H) 11.27 (s, 1 H); ESI-MS: m/z 330.1 [M+H]$^+$.

Preparation 19 4-(2-(cyclopropanecarboxamido)imidazo[1,2-a]pyridin-6-yl)thiazole-2-carboxylic acid Combined N-(6-bromoimidazo[1,2-a]pyridin-2-yl)cyclopropanecarboxamide (750 mg, 2.68 mmol), methyl 4-(4,4,5,5-tetramethyl-1,3,2-dioxaborolan-2-yl)thiazole-2-carboxylate (1441 mg, 5.35 mmol), [1,1'-bis(diphenylphosphino)ferrocene]-dichloropalladium(II) (196 mg, 0.268 mmol) in dioxane (11.9 mL) and saturated aqueous sodium bicarbonate (5.95 mL). The resulting mixture was irradiated at 115° C. for 40 minutes, then MeOH (10 mL) was added and the mixture was thoroughly sonicated and then filtered through Celite® and all solvent removed in vacuo to give a residue which re-dissolved in iPrOH (20 mL) and 1N LiOH (10 mL) and stirred at room temperature. After 1 hour, the volatile solvent removed in vacuo and EtOAc (20 mL) was added. The mixture was thoroughly sonicated and filtered. The filtrate was transferred to a separatory funnel and organic separated. Aqueous washed with EtOAc (25 mL). Aqueous was acidified with 2N HCl to pH~4 (tan semisolid precipitate). Mixture filtered to a wet solid and washed with water (5 mL). The wet filtercake/filter paper was treated with DMF (25 mL) and sonicated thoroughly to give a tan suspension. The liquid/suspension was decanted off the filter paper and the DMF removed in vacuo to give the title compound as a tan solid (864 mg, 98% yield). $^1$H NMR (400 MHz, DMSO-d6) δ ppm 0.76-0.86 (m, 3 H) 1.90-1.98 (m, 1 H) 7.52 (d, J=9.35 Hz, 1 H) 7.80 (dd, J=9.22, 1.89 Hz, 1 H) 8.15 (s, 1 H) 8.37-8.42 (m, 1 H) 9.17 (dd, J=1.77, 0.76 Hz, 1 H) 11.01 (s, 1 H); ESI-MS: m/z 329.2 [M+H]$^+$.

Preparation 20 4-(2-(cyclopropanecarboxamido)imidazo[1,2-a]pyrazin-6-yl)thiazole-2-carboxylic acid Combined N-(6-bromoimidazo[1,2-a]pyrazin-2-yl)cyclopropanecarboxamide (500 mg, 1.779 mmol), methyl 4-(4,4,5,5-tetramethyl-1,3,2-dioxaborolan-2-yl)thiazole-2-carboxylate (957 mg, 3.56 mmol), and [1,1'-bis(diphenylphosphino)ferrocene]-dichloropalladium(II) (130 mg, 0.178 mmol) in dioxane (11.9 mL) and saturated aqueous sodium bicarbonate (5.95 mL). The resulting mixture was microwaved at 115° C. for 30 minutes, then EtOAc (25 mL) was added and mixture thoroughly sonicated. A precipitate did not go into solution and the mixture was filtered to give the title compound as a grey solid. The grey solid was sonicated with DCM (20 mL) and filtered to give the title compound (285 mg). The volatile solvent was removed from the filtrate and washed with EtOAc (2×25 mL). Aqueous was acidified with 2N HCl to pH~2 at which time a brown precipitate formed and was isolated by filtration. Solid was washed with water (5 mL) and filter cake transferred to Erlenmeyer and sonicated with DMF (20 mL). Liquid was decanted off and solvent removed in vacuo to give the title compound as a tan solid (295 mg). The combined yield was 99% (580 mg). $^1$H NMR (400 MHz, DMSO-d6) δ ppm 0.84 (br. s., 4 H) 1.97 (br. s., 1 H) 7.99 (s, 1 H) 8.34 (s, 1 H) 8.90 (s, 1 H) 9.20 (s, 1 H) 11.25 (s, 1 H); ESI-MS: m/z [M+H]$^+$ 330.2.

Preparation 21 5-bromo-N-(2,2,2-trifluoroethyl)-1H-imidazole-2-carboxamide

Combined HOBT (289 mg, 1.885 mmol), DIEA (823 μl, 4.71 mmol), EDC (602 mg, 3.14 mmol) and 5-bromo-1H-imidazole-2-carboxylic acid (300 mg, 1.571 mmol) in DMF (3142 μl). After 10 minutes, 2,2,2-trifluoroethanamine (185 μl, 2.356 mmol) was added and stirred overnight. Solvent removed in vacuo and residue partitioned between water (10 mL) and EtOAc (20 mL). The organic layer was separated and washed with saturated aqueous sodium bicarbonate (10 mL) and brine (10 mL), dried over magnesium sulfate, and filtered. Solvent removed in vacuo and residue purified by column chromatography (Moritex, 40 g, 2-5% MeOH/DCM) to give the title compound as a white solid (39% yield). $^1$H NMR (400 MHz, DMSO-d6) δ ppm 3.85 (qd, J=9.85, 6.57 Hz, 3 H) 3.92-4.06 (m, 2 H) 6.81 (t, J=6.69 Hz, 1 H) 7.53 (s, 1 H) 9.19 (t, J=6.44 Hz, 1 H) 13.64 (br. s., 1 H); ESI-MS: m/z [M+H]$^+$ 272.

Preparation 22 5-chloro-N-(2,2-difluoroethyl)-1H-pyrazole-3-carboxamide

Prepared by the methodology of Preparation 21 to give the title compound as a white solid (43% yield) which was used without further purification. ESI-MS m/z [M+H]$^+$ 210.1.

Preparation 23 5-chloro-N-(2,2,2-trifluoroethyl)-1H-pyrazole-3-carboxamide

Prepared by the methodology of Preparation 21 to give the title compound as a white solid which was used without further purification. ESI-MS: m/z [M+H]$^+$ 228.0.

Preparation 24 (R)-(5-chloro-1H-pyrazol-3-yl)(2-(trifluoromethyl)pyrrolidin-1-yl)methanone Prepared by the methodology of Preparation 21 to give the title compound as a white solid (47% yield) which was used without further purification. $^1$H NMR (400 MHz, DMSO-d6) δ ppm 3.70-3.96 (m, 4 H) 4.10 (d, J=5.31 Hz, 1 H) 5.05 (t, J=8.08 Hz, 2 H) 7.95 (s, 1 H) 13.92 (br. s., 1 H); ESI-MS: m/z [M+H]$^+$ 268.2.

Preparation 25 (S)-5-chloro-N-(tetrahydrofuran-3-yl)-1H-pyrazole-3-carboxamide

Prepared by the methodology of Preparation 21 to give the title compound (46% yield) which was used without further purification. $^1$H NMR (400 MHz, DMSO-d6) δ ppm 1.77-1.92 (m, 1 H) 2.09-2.22 (m, 1 H) 3.57 (dd, J=9.09, 3.79 Hz, 1 H) 3.70 (td, J=8.21, 5.81 Hz, 1 H) 3.77-3.91 (m, 2 H) 4.38-4.48 (m, 1 H) 6.93 (s, 1 H) 8.58 (d, J=6.57 Hz, 1 H) 13.80 (br. s., 1 H); ESI-MS: m/z [M+H]$^+$ 216.1.

Preparation 26 4-(2-(cyclopropanecarboxamido)imidazo[1,2-a]pyridin-6-yl)-1H-imidazole-2-carboxylic acid Combined ethyl 4-(2-(cyclopropanecarboxamido)imidazo[1,2-a]pyridin-6-yl)-1H-imidazole-2-carboxylate (220 mg, 0.648 mmol) and dioxane (3.24 mL) and then added LiOH (4.7 mL of 1M aqueous solution). The resulting mixture stirred at room temperature overnight, then the reaction was acidified using 2N HCl (pH=3-4) and the grey precipitate was collected by vacuum filtration, washed with cold water and dried in a vacuum oven at 45° C. for 18 hours affording the title compound as a grey solid which was without further purification. (69% yield). ESI-MS m/z [M+H]$^+$ 312.6.

Preparation of 27 methyl 1-(6-aminopyridin-3-yl)-1H-imidazol-4-carboxylate

Combined 5-bromopyridine-2-amine (1 g, 5.78 mmol), methyl 1H-imidazole-4-carboxylate (1.021 g, 8.09 mmol), copper(I) iodide (0.220 g, 1.156 mmol) and cesium carbonate (3.77 g, 11.56 mmol) in DMF 25 mL. The reaction was heated to 140° C. and stirred for 12 hours. After 12 hours of heating an additional 0.2 equivilants of copper(I) iodide was added along with 500 mg of methyl 1H-imidazole-4-carboxylate and the reaction was allowed to stir an additional 12 hours at 140° C. The reaction mixture was then filtered through a 0.45 μm PTFE syringe filter and purified on HPLC using a 1-20% ACN gradient in water (TFA) to give the title compound (39.5% yield) as a yellow solid. ESI-MS m/z [M+H]$^+$ 219.2.

Preparation of 28 methyl 1-(2-(cyclopropanecaroxamido)imidazol[1,2-a]pyridine-6-yl)-1H-imidazole-4-carboxylate Methyl 1-(6-aminopyridin-3-yl)-1H-imidazol-4-carboxylate (896 mg, 4.11 mmol), N-(2-bromoacetyl)cyclopropanecarboxamide (1.7 g, 8.21 mmol) and sodium phosphate, dibasic (1.7 g, 12.32 mmol) in DMA 20 mL were combined and stirred overnight. The product was purified by HPLC using a 10-25% ACN gradient in water (TFA) to give the title compound (2% yield) as a yellow solid. ESI-MS m/z [M+H]$^+$ 326.4.

Preparation of 29 1-(2-cyclopropanecarboxamido)imidazol[1,2-a]pyridine-6-yl)-1H-imidazole-4-carboxylic acid Combined methyl 1-(2-(cyclopropanecaroxamido)imidazol[1,2-a]pyridine-6-yl)-1H-imidazole-4-carboxylate (17 mg, 0.052 mmol) in THF 2 mL followed by the addition of 1M sodium hydroxide (0.105 mL, 0.105 mmol). The reaction was stirred for 3 hours then acidified with 1M HCl to adjust the pH 1-2. The reaction mixture was then concentrated and used in the next step without further purification. ESI-MS m/z [M+H]$^+$ 312.3.

Preparation 30 3-(2-(cyclopropanecarboxamido)imidazo[1,2-a]pyridin-6-yl)-1H-pyrazole-5-carboxylic acid Combined N-(6-bromoimidazo[1,2-a]pyridin-2-yl)cyclopropanecarboxamide (250 mg, 0.892 mmol), (5-(ethoxycarbonyl)-1H-pyrazol-3-yl)boronic acid (328 mg, 1.785 mmol), and [1,1'-bis(diphenylphosphino)ferrocene]-dichloropalladium(II) (65.3 mg, 0.089 mmol) in dioxane (3967 µl) and saturated sodium bicarbonate solution (1983 µl). The resulting mixture was irradiated at 120° C. for 30 minutes and high absorbance. Additional (5-(ethoxycarbonyl)-1H-pyrazol-3-yl)boronic acid (164 mg) was added and the reaction mixture was irradiated at 120° C. for 30 minutes and high absorbance. The reaction mixture was diluted with dioxane and filtered through a pad of Celite®. The filtrate was concentrated to dryness then suspended in water (20 mL), extracted with ethyl acetate. The organic layers where evaporated to give ethyl 3-(2-(cyclopropanecarboxamido) imidazo[1,2-a]pyridin-6-yl)-1H-pyrazole-5-carboxylate (100% yield); ESI-MS m/z [M+H]$^+$ 340.3.

Ethyl 3-(2-(cyclopropanecarboxamido)imidazo[1,2-a]pyridin-6-yl)-1H-pyrazole-5-carboxylate (303 mg, 0.893 mmol) was dissolved in dioxane (3572 µl) and treated with LiOH, 1 M (3572 µl, 3.57 mmol) at 23° C. After 1 hour the reaction mixture was placed on a heating block set at 50° C. After 5 hours, the reaction was removed from the heating block and stirred for two days at 23° C. Then the dioxane was removed in vacuo and the remaining aqueous layer was then acidified to pH 1-2 with 1N HCl. The reaction was chilled in an ice bath to give a precipitate which was filtered and dried to give the title compound (36.0% yield) as a brown solid. ESI-MS m/z [M+H]$^+$ 312.3.

EXAMPLE 1

3-(2-(cyclopropanecarboxamido)imidazo[1,2-a]pyridin-6-yl)-1-methyl-N-(2,2,2-trifluoroethyl)-1H-pyrazole-5-carboxamide

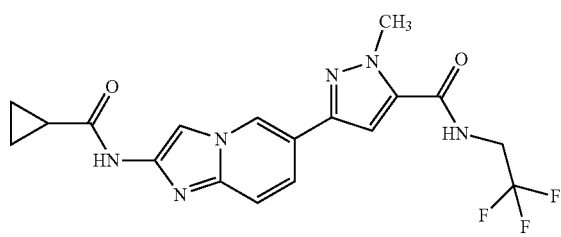 [SMILES: Cn1nc(-c2ccc3nc(NC(=O)C4CC4)cn3c2)cc1C(=O)NCC(F)(F)F]

Combined 3-(2-(cyclopropanecarboxamido)imidazo[1,2-a]pyridin-6-yl)-1-methyl-1H-pyrazole-5-carboxylic acid (50 mg, 0.154 mmol), 2,2,2-trifluoroethanamine hydrochloride (20.83 mg, 0.154 mmol), and EDC (28.6 mg, 0.184 mmol) and HOBT (24.92 mg, 0.184 mmol) in DMF (2.0 mL) followed by N-methylmorpholine (0.084 mL, 0.768 mmol) and stirred at 23° C. for 4 h. The crude material was purified by prep HPLC 20-45% ACN in water (0.1% FA) to give the title compound (7.5% yield) as a white solid. $^1$H NMR (400 MHz, DMSO-d$_6$) δ ppm 0.73-0.87 (m, 4 H) 1.93 (t, J=5.05 Hz, 1 H) 4.11 (br. s, 5 H) 7.34 (s, 1 H) 7.49 (d, J=9.35 Hz, 1 H) 7.60 (dd, J=9.22, 1.39 Hz, 1 H) 8.11 (s, 1 H) 8.96 (s, 1 H) 9.25 (t, J=6.44 Hz, 1 H) 11.00 (s, 1 H); ESI-MS: m/z 407.4 [M+H]$^+$. mp=251-255° C.

EXAMPLE 2

3-(2-(cyclopropanecarboxamido)imidazo[1,2-a]pyridin-6-yl)-N-(2,2-difluoroethyl)-1-methyl-1H-pyrazole-5-carboxamide

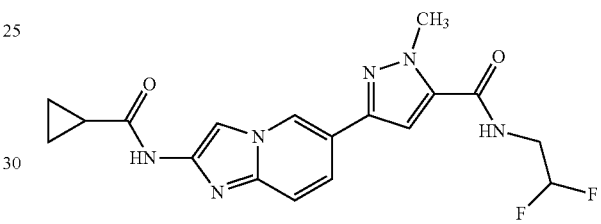

Prepared by the methodology of Example 1 using 2,2-difluoroethanamine to give the title compound (13.1% yield) as a tan solid. $^1$H NMR (400 MHz, DMSO-d$_6$) δ ppm 0.75-0.87 (m, 4 H) 1.93 (d, J=5.05 Hz, 1 H) 3.60-3.76 (m, 2 H) 4.11 (s, 3 H) 5.89-6.38 (m, 1 H) 7.29 (s, 1 H) 7.45-7.52 (m, 1 H) 7.59 (dd, J=9.22, 1.64 Hz, 1 H) 8.11 (s, 1 H) 8.94 (s, 1 H) 8.99 (t, J=5.94 Hz, 1 H) 10.99 (s, 1 H); ESI-MS: m/z 389.4 [M+H]$^+$. mp=284-290° C.

EXAMPLE 3

4-(2-(cyclopropanecarboxamido)imidazo[1,2-a]pyridin-6-yl)-N-(2,2-difluoropropyl)thiophene-2-carboxamide

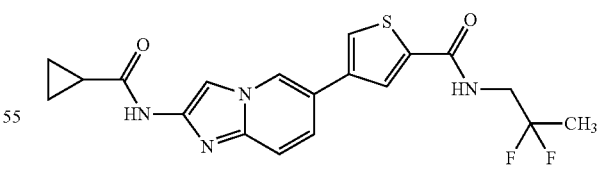

Prepare by the methodology of Example 1 using 4-(2-(cyclopropanecarboxamido)imidazo[1,2-a]pyridin-6-yl) thiophene-2-carboxylic acid and 2,2-difluoropropan-1-amine hydrochloride to give the title compound (32.1% yield) as a white solid. $^1$H NMR (400 MHz, DMSO-d$_6$) δ ppm 0.74-0.89 (m, 4 H) 1.64 (t, J=19.07 Hz, 3 H) 1.94 (t, J=6.82 Hz, 1 H) 3.74-3.80 (m, 2 H) 7.50-7.66 (m, 2 H) 8.05 (s, 1 H) 8.11 (s, 1 H) 8.31 (s, 1 H) 8.92 (s, 2 H) 11.07 (s, 1 H); ESI-MS: m/z 405.4 [M+H]$^+$. mp=117-119° C.

EXAMPLE 4

4-(2-(cyclopropanecarboxamido)imidazo[1,2-a]pyridin-6-yl)-N-(2,2,2-trifluoroethyl)thiazole-2-carboxamide

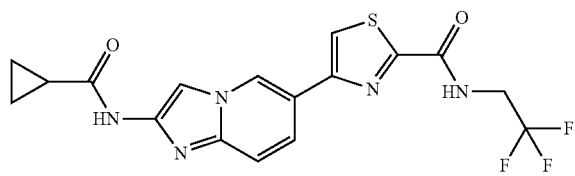

Prepared by the methodology of Example 1 using 4-(2-(cyclopropanecarboxamido)imidazo[1,2-a]pyridin-6-yl)thiazole-2-carboxylic acid to give the title compound (25.7% yield) as a white solid. $^1$H NMR (400 MHz, DMSO-$d_6$) δ ppm 0.76-0.87 (m, 4 H) 1.89-2.01 (m, 1 H) 4.07-4.21 (m, 2 H) 7.55 (d, J=9.09 Hz, 1 H) 7.90 (dd, J=9.35, 1.52 Hz, 1 H) 8.07 (s, 1 H) 8.44 (s, 1 H) 9.22 (s, 1 H) 9.51 (t, J=6.57 Hz, 1 H) 11.06 (s, 1 H); ESI-MS: m/z 410.3 [M+H]$^+$. mp=279-282° C.

EXAMPLE 5

4-(2-(cyclopropanecarboxamido)imidazo[1,2-a]pyrazin-6-yl)-N-(2,2-difluoroethyl)thiazole-2-carboxamide

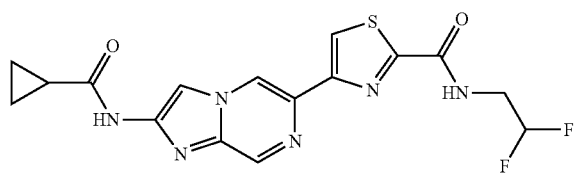

Prepared by the methodology of Example 1 using 4-(2-(cyclopropanecarboxamido)imidazo[1,2-a]pyrazin-6-yl)thiazole-2-carboxylic acid and 2,2-difluoroethanamine to give the title compound (24.8% yield) as a tan solid. $^1$H NMR (400 MHz, DMSO-$d_6$) δ ppm 0.77-0.91 (m, 4 H) 1.91-2.04 (m, 1 H) 3.68-3.85 (m, 2 H) 6.03-6.38 (m, 1 H) 8.30 (s, 1 H) 8.43 (s, 1 H) 8.98 (s, 1 H) 9.16 (t, J=6.06 Hz, 1 H) 9.24 (d, J=1.26 Hz, 1 H) 11.33 (s, 1 H); ESI-MS: m/z 393.3 [M+H]$^+$.

EXAMPLE 6

4-(2-(cyclopropanecarboxamido)imidazo[1,2-a]pyrazin-6-yl)-N-(2,2,2-trifluoroethyl)thiazole-2-carboxamide

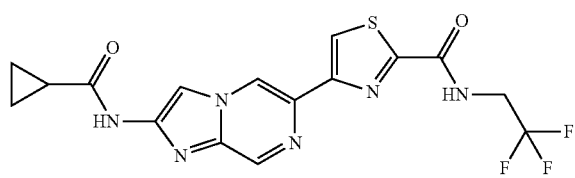 [SMILES: O=C(NCC(F)(F)F)c1nc(-c2cn3cc(NC(=O)C4CC4)nc3cn2)cs1]

Prepared by the methodology of Example 1 using 4-(2-(cyclopropanecarboxamido)imidazo[1,2-a]pyrazin-6-yl)thiazole-2-carboxylic acid to give the title compound (37.4% yield) as a tan solid. $^1$H NMR (400 MHz, DMSO-$d_6$) δ ppm 0.78-0.92 (m, 4 H) 1.92-2.04 (m, 1 H) 4.07-4.25 (m, 2 H) 8.31 (s, 1 H) 8.46 (s, 1 H) 8.98 (s, 1 H) 9.25 (d, J=1.26 Hz, 1 H) 9.48 (t, J=6.44 Hz, 1 H) 11.33 (s, 1 H); ESI-MS: m/z 411.4 [M+H]$^+$.

EXAMPLE 7

(R)-4-(2-(cyclopropanecarboxamido)imidazo[1,2-a]pyrazin-6-yl)-N-(1,1,1-trifluoropropan-2-yl)thiazole-2-carboxamide

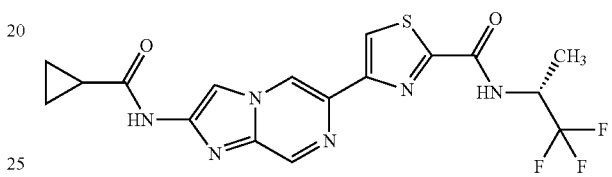

Prepared by the methodology of Example 1 using 4-(2-(cyclopropanecarboxamido)imidazo[1,2-a]pyridin-6-yl)thiazole-2-carboxylic acid and (R)-1,1,1-trifluoropropan-2-amine hydrochloride to give the title compound (15.5% yield) as a tan solid. $^1$H NMR (400 MHz, DMSO-$d_6$) δ ppm 0.75-0.88 (m, 4 H) 1.46 (d, J=6.82 Hz, 3 H) 1.90-2.00 (m, 1 H) 4.79-4.95 (m, 1 H) 7.57 (d, J=9.09 Hz, 1 H) 7.95 (dd, J=9.35, 1.52 Hz, 1 H) 8.08 (s, 1 H) 8.44 (s, 1 H) 9.25 (s, 1 H) 9.30 (d, J=9.09 Hz, 1 H) 11.09 (s, 1 H); ESI-MS: m/z 424.4 [M+H]$^+$.

EXAMPLE 8

4-(2-(cyclopropanecarboxamido)imidazo[1,2-b]pyridazin-6-yl)-N-(2,2-difluoroethyl)thiazole-2-carboxamide

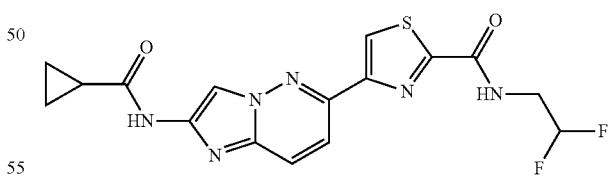

Prepared by the methodology of Example 1 using 4-(2-(cyclopropanecarboxamido)imidazo[1,2-b]pyridazin-6-yl)thiazole-2-carboxylic acid and 2,2-difluoroethanamine to give the title compound (37.0% yield) as a white solid. $^1$H NMR (400 MHz, DMSO-$d_6$) δ ppm 0.79-0.91 (m, 4 H) 1.92-2.03 (m, 1 H) 3.67-3.82 (m, 2 H) 6.03-6.36 (m, 1 H) 8.06 (d, J=9.35 Hz, 1 H) 8.18 (d, J=9.60 Hz, 1 H) 8.28 (s, 1 H) 8.69 (s, 1 H) 9.34 (t, J=6.19 Hz, 1 H) 11.28 (s, 1 H); ESI-MS: m/z 393.3 [M+H]$^+$.

EXAMPLE 9

4-{2-cyclopropaneamidoimidazo[1,2-a]pyridin-6-yl}-N-[(2R)-1,1,1-trifluoropropan-2-yl]-1H-imidazole-2-carboxamide

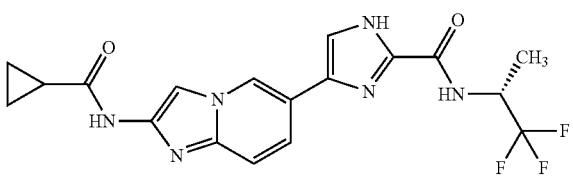

Prepared by the methodology of Example 1 using 4-(2-(cyclopropanecarboxamido)imidazo[1,2-a]pyridin-6-yl)-1H-imidazole-2-carboxylic acid and (R)-1,1,1-trifluoropropan-2-amine hydrochloride to give the title compound (88% yield) as an off-white solid. $^1$H NMR (500 MHz, DMSO-d$_6$) δ ppm 0.78-0.88 (m, 4 H) 1.42 (d, J=6.83 Hz, 3 H) 1.89-1.98 (m, 1 H) 4.69-4.96 (m, 1 H) 7.51 (d, J=9.28 Hz, 1 H) 7.81 (d, J=10.25 Hz, 2 H) 7.95-8.11 (m, 1 H) 8.87 (d, J=9.76 Hz, 1 H) 8.95-9.06 (m, 1 H) 11.08 (br. s., 1 H); ESI-MS m/z 407.6 [M+H]$^+$.

EXAMPLE 10

4-{2-cyclopropaneamidoimidazo[1,2-a]pyridin-6-yl}-N-[(2S)-1,1,1-trifluoropropan-2-yl]-1H-imidazole-2-carboxamide

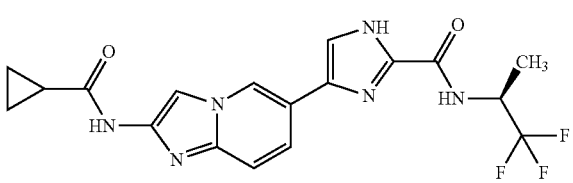 [SMILES: C[C@H](NC(=O)c1nc(-c2ccc3nc(NC(=O)C4CC4)cn3c2)c[nH]1)C(F)(F)F]

Prepared by the methodology of Example 1 using 4-(2-(cyclopropanecarboxamido)imidazo[1,2-a]pyridin-6-yl)-1H-imidazole-2-carboxylic acid and (S)-1,1,1-trifluoropropan-2-amine hydrochloride to give the title compound (89% yield) as an off-white solid. 1H NMR (500 MHz, DMSO-d6) δ ppm 0.75-0.89 (m, 4 H) 1.42 (d, J=6.83 Hz, 3 H) 1.87-2.01 (m, 1 H) 4.74-4.92 (m, 1 H) 7.50 (d, J=9.28 Hz, 1 H) 7.72-7.87 (m, 2 H) 8.02 (s, 1 H) 8.87 (d, J=8.30 Hz, 1 H) 8.98 (s, 1 H) 11.05 (br. s., 1 H); ESI-MS m/z [M+H]$^+$ 407.6.

EXAMPLE 11

4-{2-cyclopropaneamidoimidazo[1,2-a]pyridin-6-yl}-N-(2,2-difluoropropyl)-1H-imidazole-2-carboxamide

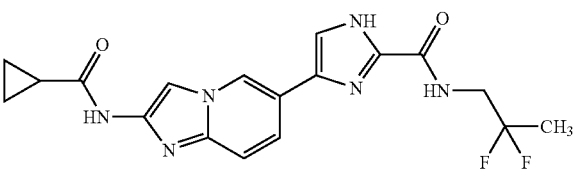 [SMILES: CC(F)(F)CNC(=O)c1nc(-c2ccc3nc(NC(=O)C4CC4)cn3c2)c[nH]1]

Prepared by the methodology of Example 1 using 4-(2-(cyclopropanecarboxamido)imidazo[1,2-a]pyridin-6-yl)-1H-imidazole-2-carboxylic acid and 2,2-difluoropropan-1-amine to give the title compound (60% yield) as a brown solid. $^1$H NMR (500 MHz, DMSO-d$_6$) δ ppm 0.81 (br. s., 4 H) 1.64 (t, J=18.79 Hz, 3 H) 1.94 (br. s., 1 H) 3.63-3.86 (m, 2 H) 7.45 (d, J=9.76 Hz, 1 H) 7.72 (d, J=9.28 Hz, 1 H) 7.81 (br. s., 1 H) 8.02 (s, 1 H) 8.59 (br. s., 1 H) 8.92 (s, 1 H) 10.96 (s, 1 H) 13.30 (br. s., 1 H); ESI-MS m/z [M+H]$^+$ 389.6.

EXAMPLE 12

4-{2-cyclopropaneamidoimidazo[1,2-a]pyridin-6-yl}-N-(2,2-difluoroethyl)-1H-imidazole-2-carboxamide

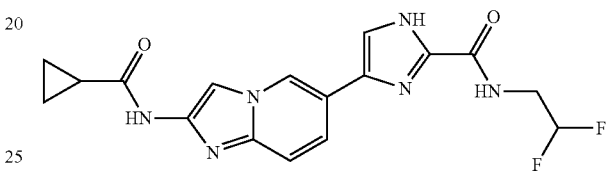

Prepared by the methodology of Example 1 using 4-(2-(cyclopropanecarboxamido)imidazo[1,2-a]pyridin-6-yl)-1H-imidazole-2-carboxylic acid and 2,2-difluoroethanamine to give the title compound (55% yield) as an off-white solid. $^1$H NMR (500 MHz, DMSO-d$_6$) δ ppm 0.74-0.88 (m, 4 H) 1.88-2.01 (m, 1 H) 3.61-3.77 (m, 2 H) 6.00-6.30 (m, 1 H) 7.46 (d, J=9.27 Hz, 1 H) 7.71 (dd, J=9.28, 1.46 Hz, 1 H) 7.81 (d, J=2.44 Hz, 1 H) 8.02 (s, 1 H) 8.66 (t, J=6.35 Hz, 1 H) 8.90 (s, 1 H) 10.96 (s, 1 H) 13.31 (br. s., 1 H); ESI-MS m/z [M+H]$^+$ 375.6.

EXAMPLE 13

4-(2-acetamidoimidazo[1,2-a]pyridin-6-yl)-N-(2,2,2-trifluoroethyl)thiophene-2-carboxamide

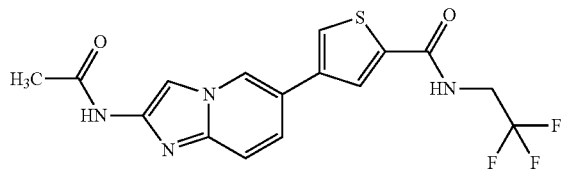 [SMILES: CC(=O)Nc1cn2cc(-c3csc(C(=O)NCC(F)(F)F)c3)ccc2n1]

Combined N-(6-bromoimidazo[1,2-a]pyridin-2-yl)acetamide (55 mg, 0.216 mmol), 4-(4,4,5,5-tetramethyl-1,3,2-dioxaborolan-2-yl)-N-(2,2,2-trifluoroethyl)thiophene-2-carboxamide (72.5 mg, 0.216 mmol) and [1,1'-bis(diphenylphosphino)ferrocene]dichloropalladium(II), complex with dichloromethane (17.81 mg, 0.022 mmol) in dioxane (2.0 mL) followed by sodium carbonate (2M, 0.433 mL, 0.866 mmol) and stirred at 125° C. for 30 min (normal absorbance) in the microwave. Then the reaction was filtered and purified by prep HPLC 15-40% ACN in water (0.1% FA) to give the title compound (16.1% yield) as a white solid. $^1$H NMR (400 MHz, DMSO-d$_6$) δ ppm 2.08 (s, 3 H) 4.03-4.19 (m, 2 H) 7.48-7.59 (m, 2 H) 8.06-8.14 (m, 2 H)

8.29 (d, J=1.26 Hz, 1 H) 8.92 (s, 1 H) 9.19 (t, J=6.19 Hz, 1 H) 10.74 (s, 1 H); ESI-MS: m/z 383.3 [M+H]⁺. mp=180-182° C.

EXAMPLE 14

4-(2-(2-methoxyacetamido)imidazo[1,2-a]pyridin-6-yl)-N-(2,2,2-trifluoroethyl)thiophene-2-carboxamide

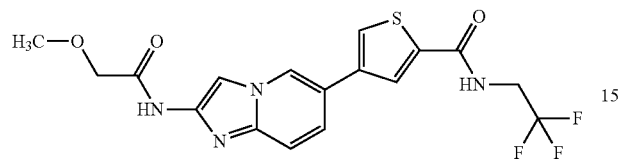

Prepared by the methodology of Example 13 using N-(6-bromoimidazo[1,2-a]pyridin-2-yl)-2-methoxyacetamide to give the title compound (32.2% yield) as a white solid. ¹H NMR (400 MHz, DMSO-d₆) δ ppm 3.36 (s, 3 H) 4.07 (s, 2 H) 4.12 (dd, J=9.73, 6.44 Hz, 2 H) 7.48-7.63 (m, 2 H) 8.11-8.18 (m, 2 H) 8.31 (d, J=1.26 Hz, 1 H) 8.95 (s, 1 H) 9.22 (t, J=6.19 Hz, 1 H) 10.49 (s, 1 H); ESI-MS: m/z 413.4 [M+H]⁺. mp=230-232° C.

EXAMPLE 15

4-(2-(3-methoxypropanamido)imidazo[1,2-a]pyridin-6-yl)-N-(2,2,2-trifluoroethyl)thiophene-2-carboxamide

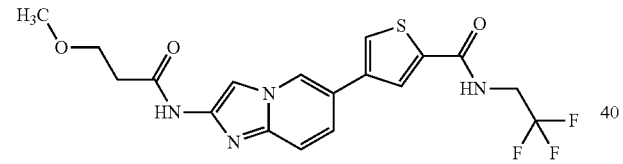

Prepared by the methodology of Example 13 using N-(6-bromoimidazo[1,2-a]pyridin-2-yl)-3-methoxypropanamide to give the title compound (45.9% yield) as a white solid. ¹H NMR (400 MHz, DMSO-d₆) δ ppm 2.61 (t, J=6.19 Hz, 2 H) 3.24 (s, 3 H) 3.63 (t, J=6.19 Hz, 2 H) 4.05-4.20 (m, 2 H) 7.48-7.62 (m, 2 H) 8.07-8.17 (m, 2 H) 8.31 (d, J=1.26 Hz, 1 H) 8.93 (s, 1 H) 9.20 (t, J=6.19 Hz, 1 H) 10.76 (s, 1 H); ESI-MS: m/z 427.4 [M+H]⁺. mp=231-233° C.

EXAMPLE 16

4-(2-(2-fluoroacetamido)imidazo[1,2-a]pyridin-6-yl)-N-(2,2,2-trifluoroethyl)thiophene-2-carboxamide

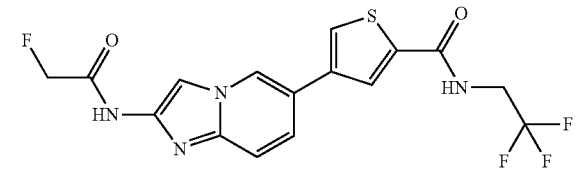 [SMILES: O=C(CF)Nc1cn2cc(-c3csc(C(=O)NCC(F)(F)F)c3)ccc2n1]

Prepared by the methodology of Example 13 using N-(6-bromoimidazo[1,2-a]pyridin-2-yl)-2-fluoroacetamide to give the title compound (5.4% yield) as a yellow solid. ¹H NMR (400 MHz, DMSO-d₆) δ ppm 4.06-4.19 (m, 2 H) 4.93-5.16 (m, 2 H) 6.61 (s, 1 H) 7.50-7.67 (m, 1 H) 8.15 (d, J=10.36 Hz, 2 H) 8.30 (s, 1 H) 8.96 (s, 1 H) 9.20 (t, J=6.19 Hz, 1 H) 10.95 (s, 1 H); ESI-MS: m/z 400.1 [M+H]⁺.

EXAMPLE 17

4-(2-(2-cyanoacetamido)imidazo[1,2-a]pyridin-6-yl)-N-(2,2,2-trifluoroethyl)thiophene-2-carboxamide

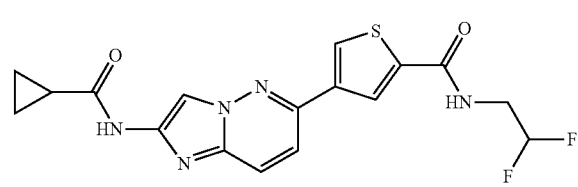

Prepared by the methodology of Example 13 using N-(6-bromoimidazo[1,2-a]pyridin-2-yl)-2-cyanoacetamide to give the title compound (12.7% yield) as a white solid. ¹H NMR (400 MHz, DMSO-d₆) δ ppm 3.97 (s, 2 H) 4.05-4.21 (m, 2 H) 7.52-7.65 (m, 2 H) 8.08-8.18 (m, 2 H) 8.30 (d, J=1.26 Hz, 1 H) 8.96 (s, 1 H) 9.20 (t, J=6.19 Hz, 1 H) 11.15 (s, 1 H); ESI-MS: m/z 408.4 [M+H]⁺.

EXAMPLE 18

4-(2-(cyclopropanecarboxamido)imidazo[1,2-b]pyridazin-6-yl)-N-(2,2-difluoroethyl)thiophene-2-carboxamide Prepared by the methodology of Example 13 using N-(6-iodoimidazo[1,2-b]pyridazin-2-yl)cyclopropanecarboxamide and N-(2,2-difluoroethyl)-4-(4,4,5,5-tetramethyl-1,3,2-dioxaborolan-2-yl)thiophene-2-carboxamide to give the title compound (44.6% yield) as an off-white solid. ¹H NMR (400 MHz, DMSO-d₆) δ ppm 0.77-0.91 (m, 4 H) 1.92-2.01 (m, 1 H) 3.61-3.75 (m, 2 H) 5.97-6.30 (m, 1 H) 7.75 (d, J=9.60 Hz, 1 H) 8.08 (d, J=9.35 Hz, 1 H) 8.21 (s, 1 H) 8.48-8.60 (m, 2 H) 9.15 (t, J=5.81 Hz, 1 H) 11.22 (s, 1 H); ESI-MS: m/z 392.4 [M+H]⁺.

EXAMPLE 19

4-(2-(cyclopropanecarboxamido)imidazo[1,2-a]pyrazin-6-yl)-N-(2,2-difluoroethyl)thiophene-2-carboxamide

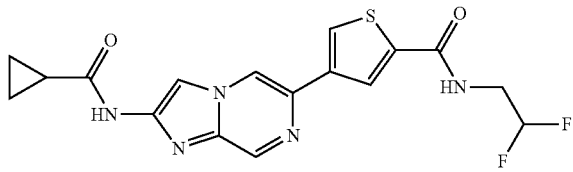

Prepared by the methodology of Example 13 using N-(6-bromoimidazo[1,2-a]pyrazin-2-yl)cyclopropanecarboxamide and N-(2,2-difluoroethyl)-4-(4,4,5,5-tetramethyl-1,3,2-dioxaborolan-2-yl)thiophene-2-carboxamide to give the title compound (55.6% yield) as an off-white solid. $^1$H NMR (500 MHz, DMSO-d$_6$) δ ppm 0.80-0.89 (m, 4 H) 1.93-2.01 (m, 1 H) 3.62-3.74 (m, 2 H) 5.99-6.28 (m, 1 H) 8.21 (d, J=0.98 Hz, 1 H) 8.23 (s, 1 H) 8.40 (d, J=1.46 Hz, 1 H) 8.94 (s, 1 H) 9.01-9.08 (m, 2 H) 11.29 (s, 1 H); ESI-MS: m/z 392.2 [M+H]$^+$.

EXAMPLE 20

4-(2-(cyclopropanecarboxamido)imidazo[1,2-b]pyridazin-6-yl)-5-methyl-N-(2,2,2-trifluoroethyl)thiazole-2-carboxamide

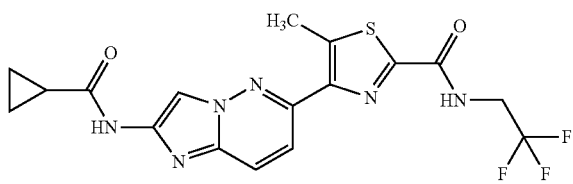

Prepared by the methodology of Example 13 using N-(6-chloroimidazo[1,2-b]pyridazin-2-yl)cyclopropanecarboxamide and 5-methyl-4-(4,4,5,5-tetramethyl-1,3,2-dioxaborolan-2-yl)-N-(2,2,2-trifluoroethyl)thiazole-2-carboxamide to give the title compound (4.0% yield) as a white solid. $^1$H NMR (400 MHz, DMSO-d$_6$) δ ppm 0.70-0.84 (m, 4 H) 1.91 (t, J=5.56 Hz, 1 H) 2.82 (s, 3 H) 4.04 (dd, J=9.47, 6.69 Hz, 2 H) 8.00 (d, J=9.35 Hz, 1 H) 8.08 (d, J=9.35 Hz, 1 H) 8.22 (s, 1 H) 9.49 (t, J=6.44 Hz, 1 H) 11.18 (s, 1 H); ESI-MS m/z [M+H]$^+$ 425.0.

EXAMPLE 21

4-(2-(cyclopropanecarboxamido)imidazo[1,2-b]pyridazin-6-yl)-N-(2,2,2-trifluoroethyl)thiazole-2-carboxamide

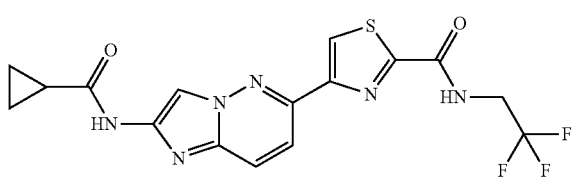 [SMILES: O=C(NCC(F)(F)F)c1nc(-c2ccc3nc(NC(=O)C4CC4)cn3n2)cs1]

Prepared by the methodology of Example 13 using N-(6-chloroimidazo[1,2-b]pyridazin-2-yl)cyclopropanecarboxamide and 5-methyl-4-(4,4,5,5-tetramethyl-1,3,2-dioxaborolan-2-yl)-N-(2,2,2-trifluoroethyl)thiazole-2-carboxamide to give the title compound (25% yield) as a yellow solid. $^1$H NMR (400 MHz, DMSO-d$_6$) δ ppm 0.76-0.95 (m, 4 H) 1.98 (t, J=5.05 Hz, 1 H) 4.14 (dd, J=9.35, 6.82 Hz, 2 H) 8.09 (d, J=9.35 Hz, 1 H) 8.19 (d, J=9.35 Hz, 1 H) 8.29 (s, 1 H) 8.72 (s, 1 H) 9.65 (t, J=6.44 Hz, 1 H) 11.29 (s, 1 H); ESI-MS m/z [M+H]$^+$ 411.0.

EXAMPLE 22

5-(2-(cyclopropanecarboxamido)imidazo[1,2-a]pyridin-6-yl)-N-(2,2,2-trifluoroethyl)thiazole-2-carboxamide

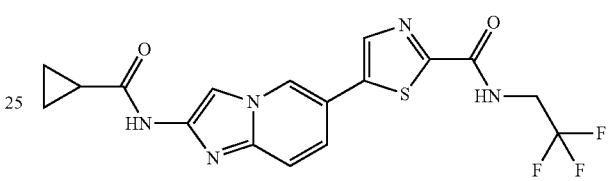

Prepared by the methodology of Example 13 using 5-bromo-N-(2,2,2-trifluoroethyl)thiazole-2-carboxamide to give the title compound (15.8% yield) as a tan solid. $^1$H NMR (400 MHz, DMSO-d$_6$) δ ppm 0.74-0.88 (m, 4 H) 1.88-2.01 (m, 1 H) 3.99-4.17 (m, 2 H) 7.49-7.59 (m, 1 H) 7.65 (dd, J=9.35, 1.77 Hz, 1 H) 8.08 (s, 1 H) 8.46 (s, 1 H) 9.12 (s, 1 H) 9.53 (t, J=6.44 Hz, 1 H) 11.07 (s, 1 H); ESI-MS: m/z 410.4 [M+H]$^+$.

EXAMPLE 23

4-(2-(cyclopropanecarboxamido)imidazo[1,2-b]pyridazin-6-yl)-5-methyl-N-(2,2,2-trifluoroethyl)thiophene-2-carboxamide

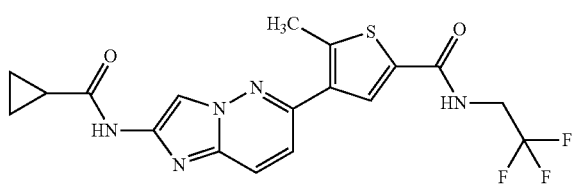 [SMILES: Cc1sc(C(=O)NCC(F)(F)F)cc1-c1ccc2nc(NC(=O)C3CC3)cn2n1]

Prepared by the methodology of Example 13 using N-(6-chloroimidazo[1,2-b]pyridazin-2-yl)cyclopropanecarboxamide and 5-methyl-4-(4,4,5,5-tetramethyl-1,3,2-dioxaborolan-2-yl)-N-(2,2,2-trifluoroethyl)thiophene-2-carboxamide to give the title compound (14% yield) as a green solid. $^1$H NMR (400 MHz, DMSO-d$_6$) δ ppm 0.73-0.96 (m, 4 H) 1.83-2.04 (m, 1 H) 2.71 (s, 3 H) 3.98-4.16 (m, 2 H) 7.47 (d, J=9.35 Hz, 1 H) 8.09 (d, J=9.35 Hz, 1 H) 8.25 (d, J=2.27 Hz, 2 H) 9.20 (t, J=6.19 Hz, 1 H) 11.24 (s, 1 H); ESI-MS m/z [M+H]$^+$ 424.0.

EXAMPLE 24

4-(2-(cyclopropanecarboxamido)imidazo[1,2-a]pyridin-6-yl)-N-(1,1,1-trifluoropropan-2-yl)-1H-imidazole-2-carboxamide

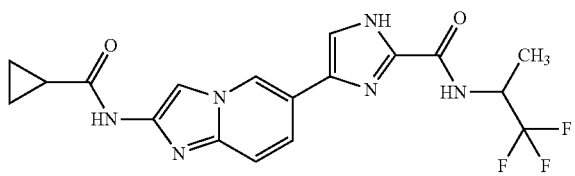 [SMILES: CC(NC(=O)c1nc(-c2ccc3nc(NC(=O)C4CC4)cn3c2)c[nH]1)C(F)(F)F]

Prepared by the methodology of Example 13 using (2-(cyclopropanecarboxamido)imidazo[1,2-a]pyridin-6-yl)boronic acid and 4-bromo-N-(1,1,1-trifluoropropan-2-yl)-1H-imidazole-2-carboxamide to give the title compound (51.7% yield) as a white solid. $^1$H NMR (400 MHz, DMSO-d$_6$) δ ppm 0.76-0.87 (m, 4 H) 1.42 (d, J=6.82 Hz, 3 H) 1.93 (br. s., 1 H) 4.78-4.88 (m, 1 H) 7.48 (d, J=9.35 Hz, 1 H) 7.76 (d, J=9.09 Hz, 1 H) 7.81 (br. s., 1 H) 8.01 (s, 1 H) 8.89 (d, J=8.84 Hz, 1 H) 8.97 (s, 1 H) 11.03 (s, 1 H); ESI-MS: m/z 407.4 [M+H]$^+$.

EXAMPLE 25

3-(2-(cyclopropanecarboxamido)imidazo[1,2-a]pyridin-6-yl)-4-methyl-N-(2,2,2-trifluoroethyl)-1H-pyrazole-5-carboxamide

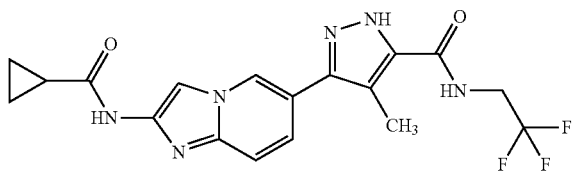 [SMILES: Cc1c(-c2ccc3nc(NC(=O)C4CC4)cn3c2)n[nH]c1C(=O)NCC(F)(F)F]

Prepared by the methodology of Example 13 using (2-(cyclopropanecarboxamido)imidazo[1,2-a]pyridin-6-yl)boronic acid and 5-bromo-4-methyl-N-(2,2,2-trifluoroethyl)-1H-pyrazole-3-carboxamide to give the title compound (34.4% yield) as an tan solid. $^1$H NMR (400 MHz, DMSO-d$_6$) δ ppm 0.74-0.88 (m, 4 H) 1.95 (t, J=4.93 Hz, 1 H) 2.35 (s, 3 H) 3.94-4.11 (m, 2 H) 7.38 (d, J=8.84 Hz, 1 H) 7.55 (d, J=9.09 Hz, 1 H) 8.15 (s, 1 H) 8.69 (t, J=6.44 Hz, 1 H) 8.77 (s, 1 H) 11.03 (s, 1 H) 13.55 (br. s., 1 H); ESI-MS: m/z 407.4 [M+H]$^+$. mp>275° C.

EXAMPLE 26

5-(2-(cyclopropanecarboxamido)imidazo[1,2-a]pyridin-6-yl)-N-(2,2,2-trifluoroethyl)isothiazole-3-carboxamide

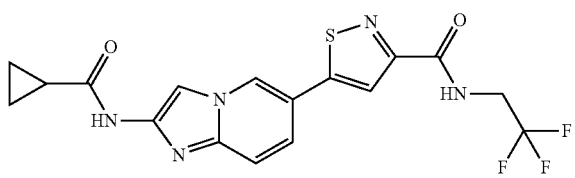 [SMILES: O=C(NCC(F)(F)F)c1cc(-c2ccc3nc(NC(=O)C4CC4)cn3c2)sn1]

Prepared by the methodology of Example 13 using (2-(cyclopropanecarboxamido)imidazo[1,2-a]pyridin-6-yl)boronic acid and 5-bromo-N-(2,2,2-trifluoroethyl)isothiazole-3-carboxamide to give the title compound as a white solid. $^1$H NMR (400 MHz, DMSO-d$_6$) δ ppm 0.81-0.84 (m, 4 H) 1.95 (m, 1 H) 4.06-4.09 (m, 2 H) 7.54 (d, J=7.60 Hz, 1 H) 7.62 (d, J=7.60 Hz, 1 H) 8.09 (s, 1 H) 8.21 (s, 1 H) 8.25 (s, 1 H) 9.31 (s, 1 H) 11.07 (s, 1 H); ESI-MS: m/z 410.0 [M+H]$^+$.

EXAMPLE 27

5-(2-(cyclopropanecarboxamido)imidazo[1,2-a]pyridin-6-yl)-N-(2,2-difluoroethyl)-1H-pyrazole-3-carboxamide

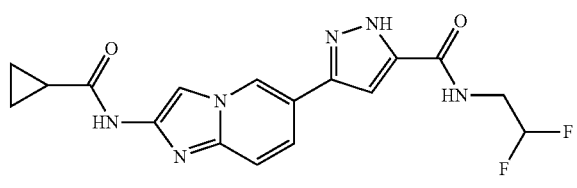 [SMILES: O=C(NCC(F)F)c1cc(-c2ccc3nc(NC(=O)C4CC4)cn3c2)n[nH]1]

Combined (2-(cyclopropanecarboxamido)imidazo[1,2-a]pyridin-6-yl)boronic acid (1.060 mL, 0.477 mmol), 5-chloro-N-(2,2-difluoroethyl)-1H-pyrazole-3-carboxamide (0.500 mL, 0.239 mmol) and [1,1'-bis(diphenylphosphino)ferrocene]dichloropalladium(II) complex with dichloromethane (19.63 mg, 0.024 mmol) in dioxane (2.0 mL) and aqueous sodium carbonate solution (2M, 0.477 mL, 0.954 mmol). The reaction mixture was irradiated in a microwave at 125° C. at normal absorbance for 30 minutes, then (2-(cyclopropanecarboxamido)imidazo[1,2-a]pyridin-6-yl) boronic acid (1.060 mL, 0.477 mmol), [1,1'-bis(diphenylphosphino) ferrocene]dichloropalladium(II) complex with dichloromethane and aqueous sodium carbonate solution (2M, 0.477 mL, 0.954 mmol) were added and the reaction mixture was irradiated at 125° C. at normal absorbance for 30 minutes. The product was purified by preparative HPLC (Sunfire™ C18, 5 μm, 30×75 mm column) using a gradient eluent of 20-40% ACN in water (TFA) to give the title compound, (1% yield) as its TFA salt, as a white solid. $^1$H NMR (400 MHz, DMSO-d$_6$) δ ppm 0.79-0.88 (m, 4 H) 1.96 (br. s., 1 H) 3.67 (br. s., 2 H) 5.95-6.29 (m, 1 H) 5.95-6.29 (m, 1 H) 7.54 (s, 1 H) 7.64 (d, J=7.07 Hz, 1 H) 8.07-8.12 (m, 1 H) 8.53-8.61 (m, 1 H) 9.01 (s, 1 H) 11.02 (br. s., 1 H) 13.77 (s, 1 H); ESI-MS m/z [M+H]$^+$ 375.4.

EXAMPLE 28

4-(2-(cyclopropanecarboxamido)imidazo[1,2-a]pyridin-6-yl)-N-methyl-N-(2,2,2-trifluoroethyl)thiophene-2-carboxamide

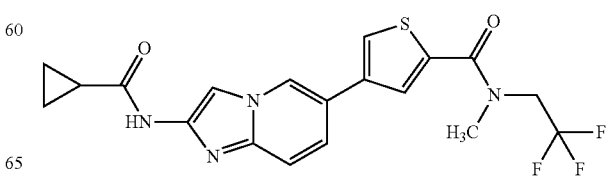

Combined N-(6-bromoimidazo[1,2-a]pyridin-2-yl)cyclopropanecarboxamide (50 mg, 0.178 mmol), N-methyl-4-(4,4,5,5-tetramethyl-1,3,2-dioxaborolan-2-yl)-N-(2,2,2-trifluoroethyl)thiophene-2-carboxamide (100 mg, 0.286 mmol), and [1,1'-bis(diphenylphosphino)ferrocene]-dichloropalladium(II) (13.06 mg, 0.018 mmol) in dioxane (793 μl) and saturated aqueous sodium bicarbonate (397 μl). The mixture was irradiated in a microwave at 120° C., 30 minutes, high absorbance. The reaction mixture was purified by preparative HPLC (Waters XSelect™ C18, 5 um, ID30×75 mm column) using a gradient eluent of 20-45% ACN (with 0.1% FA) in water (with 0.1% FA) to give the title compound (5% yield) as a beige solid. $^1$H NMR (400 MHz, DMSO-$d_6$) δ ppm 0.77-0.90 (m, 4 H) 1.89-2.03 (m, 1 H) 3.42 (br. s., 3 H) 4.44 (d, J=9.60 Hz, 2 H) 7.49 (d, J=9.35 Hz, 1 H) 7.67 (dd, J=9.35, 1.77 Hz, 1 H) 7.99-8.09 (m, 2 H) 8.12-8.21 (m, 1 H) 9.06 (s, 1 H) 11.01 (s, 1 H); ESI-MS m/z [M+H]$^+$ 423.3.

EXAMPLE 29

4-(2-(cyclopropanecarboxamido)imidazo[1,2-a]pyridin-6-yl)-5-methyl-N-(2,2,2-trifluoroethyl)thiophene-2-carboxamide

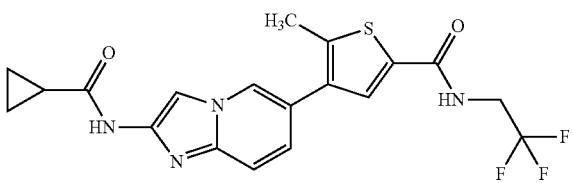 [SMILES: Cc1sc(C(=O)NCC(F)(F)F)cc1-c1ccc2nc(NC(=O)C3CC3)cn2c1]

Combined N-(6-bromoimidazo[1,2-a]pyridin-2-yl)cyclopropanecarboxamide (45 mg, 0.161 mmol), 5-methyl-4-(4,4,5,5-tetramethyl-1,3,2-dioxaborolan-2-yl)-N-(2,2,2-trifluoroethyl)thiophene-2-carboxamide (64.5 mg, 0.185 mmol), 2M solution of sodium carbonate (0.321 mL, 0.643 mmol), and PdCl$_2$(dppf) (17.63 mg, 0.024 mmol) in 1,4-dioxane (1.4 mL) and water (426 μl, 23.66 mmol). The mixture was irradiated in a microwave at 135° C. for 30 min. The reaction mixture purified by preparative HPLC (SunFire™ C18, 5 μm, ID 30 mm×75 mm) using a gradient of 20-50% ACN in water (TFA) to give the title compound (23% yield) as a brown oil. ESI-MS m/z [M+H]$^+$ 422.0.

EXAMPLE 30

4-(2-(cyclopropanecarboxamido)imidazo[1,2-a]pyrazin-6-yl)-5-methyl-N-(2,2,2-trifluoroethyl)thiophene-2-carboxamide

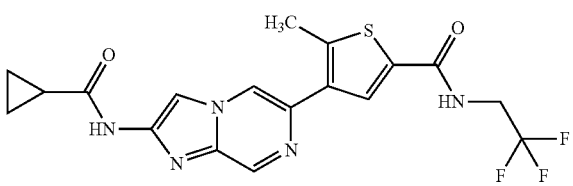 [SMILES: Cc1sc(C(=O)NCC(F)(F)F)cc1-c1cn2cc(NC(=O)C3CC3)nc2cn1]

Prepared by the methodology of Example 29 using N-(6-bromoimidazo[1,2-a]pyrazin-2-yl)cyclopropanecarboxamide to give the title compound (46% yield) as a white solid. ESI-MS m/z [M+H]$^+$ 423.0.

EXAMPLE 31

4-(2-(cyclopropanecarboxamido)imidazo[1,2-a]pyridin-6-yl)-5-methyl-N-(2,2,2-trifluoroethyl)thiazole-2-carboxamide

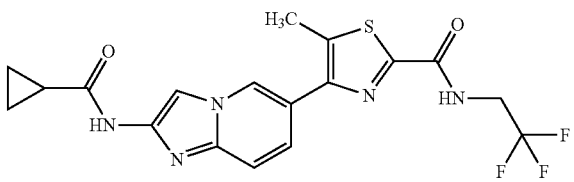 [SMILES: Cc1sc(C(=O)NCC(F)(F)F)nc1-c1ccc2nc(NC(=O)C3CC3)cn2c1]

Prepared by the methodology of Example 29 using (2-(cyclopropanecarboxamido)imidazo[1,2-a]pyridin-6-yl)boronic acid to give the title compound (50% yield) as a clear oil. ESI-MS m/z [M+H]$^+$ 423.0.

EXAMPLE 32

4-(2-(cyclopropanecarboxamido)imidazo[1,2-a]pyridin-6-yl)-N-(2,2,2-trifluoroethyl)thiophene-2-carboxamide

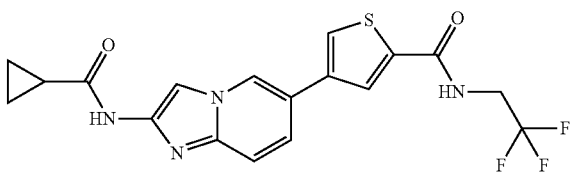

Prepared by the methodology of Example 29 using 4-(4,4,5,5-tetramethyl-1,3,2-dioxaborolan-2-yl)-N-(2,2,2-trifluoroethyl)thiophene-2-carboxamide to give the title compound (15% yield) as a white solid. $^1$H NMR (400 MHz, DMSO-$d_6$) δ ppm 0.73-0.87 (m, 4 H) 1.94 (t, J=4.17 Hz, 1 H) 4.12 (dd, J=9.47, 6.19 Hz, 2 H) 7.46-7.62 (m, 2 H) 8.05 (s, 1 H) 8.14 (s, 1 H) 8.30 (s, 1 H) 8.91 (s, 1 H) 9.20 (t, J=6.06 Hz, 1 H) 11.02 (s, 1 H); ESI-MS m/z [M+H]$^+$ 409.0.

EXAMPLE 33

4-(2-(cyclopropanecarboxamido)imidazo[1,2-a]pyrazin-6-yl)-N-(2,2,2-trifluoroethyl)thiophene-2-carboxamide

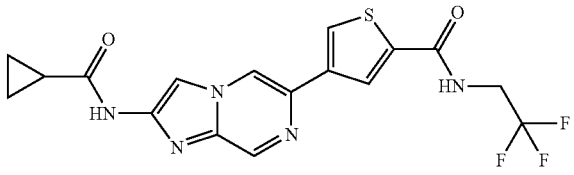 [SMILES: O=C(NCC(F)(F)F)c1cc(-c2cn3cc(NC(=O)C4CC4)nc3cn2)cs1]

Prepared by the methodology of Example 29 using N-(6-bromoimidazo[1,2-a]pyrazin-2-yl)cyclopropanecarboxamide and 4-(4,4,5,5-tetramethyl-1,3,2-dioxaborolan-2-yl)-N-(2,2,2-trifluoroethyl)thiophene-2-carboxamide to give the title compound (5% yield) as a white solid. $^1$H NMR (400

MHz, DMSO-d6) δ ppm 0.80-0.88 (m, 4 H) 1.93-2.01 (m, 1 H) 4.09 (q, J=9.77 Hz, 2 H) 8.21-8.26 (m, 2 H) 8.45 (d, J=1.26 Hz, 1 H) 8.92-8.97 (m, 1 H) 9.05-9.08 (m, 1 H) 9.34 (d, J=16.17 Hz, 1 H) 11.31 (br. s., 1 H); ESI-MS m/z [M+H]$^+$ 410.0.

EXAMPLE 34

1-(2-(cyclopropanecarboxamido)imidazo[1,2-a]pyridin-6-yl)-N-(2,2,2-trifluoroethyl)-1H-pyrazole-3-carboxamide

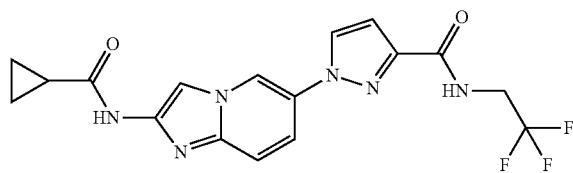

Combined N-(6-bromoimidazo[1,2-a]pyridin-2-yl)cyclopropanecarboxamide (200 mg, 0.714 mmol), N-(2,2,2-trifluoroethyl)-1H-pyrazole-3-carboxamide (207 mg, 1.071 mmol), ((thiophene-2-carbonyl)oxy)copper (13.61 mg, 0.071 mmol) and Cs$_2$CO$_3$ (698 mg, 2.142 mmol) in DMF (3.0 mL) and stirred at 180° C. for 1 hour (normal absorbance) in the microwave. The reaction mixture was filtered and purified by prep HPLC 20-45% ACN in water (0.1% FA) to give the title compound (8.6% yield) as a tan solid. $^1$H NMR (400 MHz, DMSO-d$_6$) δ ppm 0.77-0.88 (m, 4 H) 1.90-1.99 (m, 1 H) 4.07 (dd, J=9.85, 6.57 Hz, 2 H) 7.00 (d, J=2.27 Hz, 1 H) 7.62 (d, J=9.60 Hz, 1 H) 7.82 (dd, J=9.60, 2.02 Hz, 1 H) 8.13 (s, 1 H) 8.52 (d, J=2.53 Hz, 1 H) 8.92-9.02 (m, 1 H) 9.20 (s, 1 H) 11.09 (s, 1 H); ESI-MS: m/z 393.4 [M+H]$^+$.

EXAMPLE 35

1-(2-(cyclopropanecarboxamido)imidazo[1,2-a]pyridin-6-yl)-N-(2,2-difluoroethyl)-1H-pyrazole-3-carboxamide

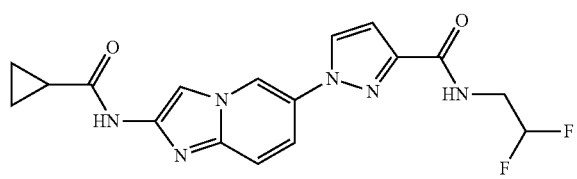 [SMILES: O=C(NCC(F)F)c1ccn(-c2ccc3nc(NC(=O)C4CC4)cn3c2)n1]

Prepared by the methodology of Example 34 using N-(2,2-difluoroethyl)-1H-pyrazole-3-carboxamide to give the title compound (6.81% yield) as a tan solid. $^1$H NMR (400 MHz, DMSO-d$_6$) δ ppm 0.82 (d, J=5.05 Hz, 4 H) 3.56-3.83 (m, 1 H) 5.91-6.36 (m, 1 H) 6.96 (d, J=2.53 Hz, 1 H) 7.29-7.35 (m, 1 H) 7.38-7.44 (m, 1 H) 7.62 (d, J=8.59 Hz, 1 H) 7.82 (d, J=7.83 Hz, 1 H) 8.15 (br. s., 1 H) 8.50 (d, J=2.53 Hz, 1 H) 8.68 (t, J=6.06 Hz, 1 H) 9.20 (br. s., 1 H) 10.97-11.16 (m, 1 H); ESI-MS: m/z 375.4 [M+H]$^+$.

EXAMPLE 36

1-(2-(cyclopropanecarboxamido)imidazo[1,2-a]pyrazin-6-yl)-N-(2,2,2-trifluoroethyl)-1H-pyrazole-3-carboxamide

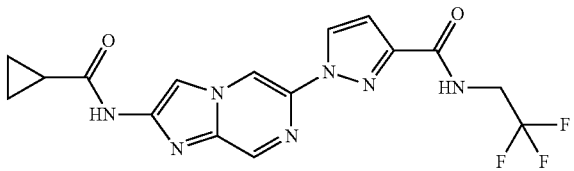 [SMILES: O=C(NCC(F)(F)F)c1ccn(-c2cn3cc(NC(=O)C4CC4)nc3cn2)n1]

Prepared by the methodology of Example 34 using N-(6-bromoimidazo[1,2-a]pyrazin-2-yl)cyclopropanecarboxamide to give the title compound (8.9% yield) as a tan solid. $^1$H NMR (400 MHz, DMSO-d$_6$) δ ppm 0.79-0.91 (m, 4 H) 1.93-2.03 (m, 1 H) 4.03-4.17 (m, 2 H) 7.00 (d, J=2.53 Hz, 1 H) 8.44 (s, 1 H) 8.60 (d, J=2.53 Hz, 1 H) 8.90 (s, 1 H) 8.96 (t, J=6.44 Hz, 1 H) 9.23 (d, J=1.26 Hz, 1 H) 11.36 (s, 1 H); ESI-MS: m/z 394.3 [M+H]$^+$.

EXAMPLE 37

1-(2-(cyclopropanecarboxamido)imidazo[1,2-b]pyridazin-6-yl)-N-(2,2-difluoroethyl)-1H-pyrazole-3-carboxamide

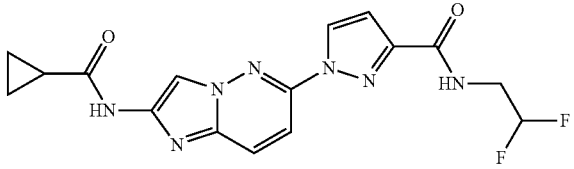

Prepared by the methodology of Example 34 using N-(6-iodoimidazo[1,2-b]pyridazin-2-yl)cyclopropanecarboxamide and N-(2,2-difluoroethyl)-1H-pyrazole-3-carboxamide to give the title compound (11.5% yield) as a tan solid. $^1$H NMR (400 MHz, DMSO-d$_6$) δ ppm 0.78-0.90 (m, 4 H) 1.96 (t, J=5.18 Hz, 1 H) 3.62-3.77 (m, 2 H) 5.97-6.32 (m, 1 H) 6.98-7.04 (m, 1 H) 7.96 (d, J=9.60 Hz, 1 H) 8.24-8.32 (m, 2 H) 8.68 (d, J=2.78 Hz, 1 H) 8.87 (t, J=6.06 Hz, 1 H) 11.29 (s, 1 H); ESI-MS: m/z 376.3 [M+H]$^+$.

EXAMPLE 38

1-(2-(cyclopropanecarboxamido)imidazo[1,2-a]pyrazin-6-yl)-N-(2,2-difluoroethyl)-1H-pyrazole-3-carboxamide

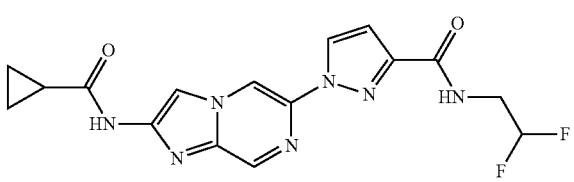

Prepared by the methodology of Example 34 using N-(6-bromoimidazo[1,2-a]pyrazin-2-yl)cyclopropanecarboxamide and N-(2,2-difluoroethyl)-1H-pyrazole-3-carboxamide to give the title compound (17.1% yield) as a tan solid. ¹H NMR (400 MHz, DMSO-d₆) δ ppm 0.77-0.93 (m, 4 H) 1.98 (quin, J=6.06 Hz, 1 H) 3.62-3.79 (m, 1 H) 5.96-6.35 (m, 1 H) 6.95-7.09 (m, 1 H) 7.43 (s, 1 H) 8.27 (s, 1 H) 8.41-8.53 (m, 1 H) 8.64-8.70 (m, 1 H) 8.90 (s, 1 H) 9.19-9.34 (m, 1 H) 11.35 (d, J=11.62 Hz, 1 H); ESI-MS: m/z 376.3 [M+H]⁺.

EXAMPLE 39

1-(2-(cyclopropanecarboxamido)imidazo[1,2-b]pyridazin-6-yl)-N-(2,2,2-trifluoroethyl)-1H-pyrazole-3-carboxamide

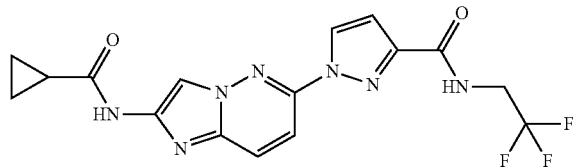 [SMILES: O=C(NCC(F)(F)F)c1ccn(-c2ccc3nc(NC(=O)C4CC4)cn3n2)n1]

Prepared by the methodology of Example 34 using N-(6-iodoimidazo[1,2-b]pyridazin-2-yl)cyclopropanecarboxamide to give the title compound (7.9% yield) as a tan solid. ¹H NMR (400 MHz, DMSO-d₆) δ ppm 0.79-0.90 (m, 4 H) 1.96 (t, J=5.18 Hz, 1 H) 4.01-4.15 (m, 2 H) 7.04 (d, J=2.78 Hz, 1 H) 7.98 (d, J=9.60 Hz, 1 H) 8.24-8.31 (m, 2 H) 8.70 (d, J=2.78 Hz, 1 H) 9.15 (t, J=6.44 Hz, 1 H) 11.30 (s, 1 H); ESI-MS: m/z 394.3 [M+H]⁺.

EXAMPLE 40

1-(2-(cyclopropanecarboxamido)imidazo[1,2-a]pyridin-6-yl)-N-(2,2,2-trifluoroethyl)-1H-pyrazole-4-carboxamide

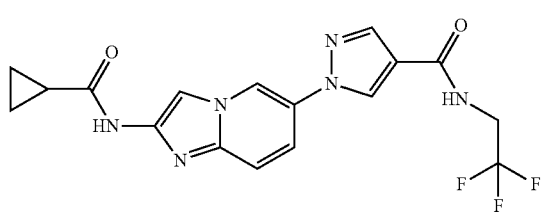 [SMILES: O=C(NCC(F)(F)F)c1cnn(-c2ccc3nc(NC(=O)C4CC4)cn3c2)c1]

Prepared by the methodology of Example 34 using N-(2,2,2-trifluoroethyl)-1H-pyrazole-4-carboxamide to give the title compound. ¹H NMR (400 MHz, DMSO-d₆) δ ppm 0.80-0.83 (m, 4 H) 1.95 (m, 1 H) 4.08-4.11 (m, 1 H) 7.58 (d, J=7.60 Hz, 1 H) 7.72 (d, J=7.60 Hz, 1 H) 8.15 (s, 1 H) 8.25 (s, 1 H) 8.87 (t, J=6.19 Hz, 1 H) 8.92 (s, 1 H) 9.16 (s, 1 H) 11.04 (s, 1 H); ESI-MS: m/z 393.3 [M+H]⁺.

EXAMPLE 41

1-(2-(cyclopropanecarboxamido)imidazo[1,2-a]pyridin-6-yl)-N-(2,2,2-trifluoroethyl)-1H-imidazole-4-carboxamide

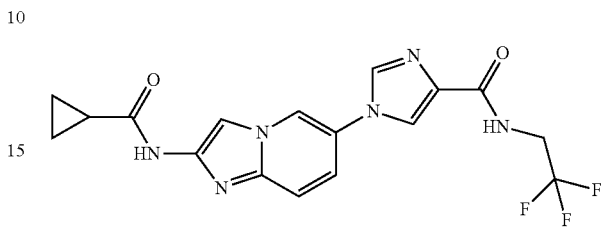

Combined 1-(2-(cyclopropanecarboxamido)imidazol[1,2-a]pyridine-6-yl)-1H-imidazole-4-carboxylic acid (20 mg, 0.064 mmol), 2,2,2-trifluoroethanamine (9.55 mg, 0.096 mmol), EDC (18.47 mg, 0.096 mmol), HOBT (14.76 mg, 0.096 mmol) and DIEA (0.022 mL, 0.128 mmol) in DMF (1 mL) and stirred for 18 hrs. The reaction mixture was then purified on HPLC using a 15-40% ACN gradient in water with (TFA) to give the title compound (12% yield) as a white solid. ¹H NMR (400 MHz, DMSO-d₆) δ ppm 0.74-0.90 (m, 4 H) 1.87-2.04 (m, 1 H) 3.92-4.13 (m, 2 H) 7.54-7.69 (m, 2 H) 8.03-8.13 (m, 1 H) 8.25-8.39 (m, 2 H) 8.63-8.77 (m, 1 H) 9.03-9.17 (m, 1 H) 11.01-11.16 (m, 1 H); ESI-MS: m/z 393.2 [M+H]⁺.

EXAMPLE 42

1-(2-(cyclopropanecarboxamido)imidazo[1,2-a]pyridin-6-yl)-N-(2,2-difluoropropyl)-1H-imidazole-4-carboxamide

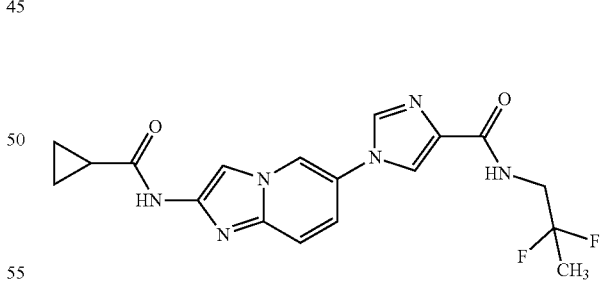

Prepared by the methodology of Example 41 using 2,2-difluoropropane-1-amine to give the title compound, as its TFA salt, (20% yield) as a white solid. ¹H NMR (400 MHz, DMSO-d₆) δ ppm 0.77-0.86 (m, 4 H) 1.51-1.69 (m, 3 H) 1.88-2.00 (m, 1 H) 3.64-3.79 (m, 2 H) 7.53-7.67 (m, 2 H) 8.02-8.13 (m, 1 H) 8.22-8.40 (m, 3 H) 9.05-9.15 (m, 1 H) 11.06-11.15 (m, 1 H); ESI-MS: m/z 389.2 [M+H]⁺.

EXAMPLE 43

(R)-1-(2-cyclopropanecarboxamido)imidazol[1,2-a]pyridine-6-yl)-N-(1,1,1-trifluoropropan-2-yl)-1H-imidazole-4-caboxamide

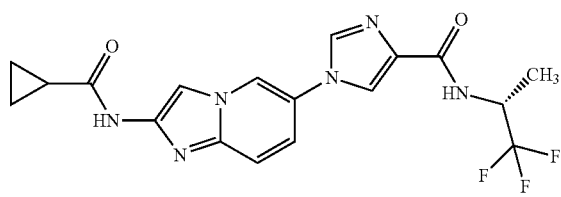 [SMILES: C[C@@H](NC(=O)c1cn(-c2ccc3nc(NC(=O)C4CC4)cn3c2)cn1)C(F)(F)F]

Combined 1-(2-(cyclopropanecarboxamido)imidazo[1,2-a]pyridine-6-yl)-1H-imidazol-4-carboxylic acid (16 mg, 0.051 mmol), (R)-1,1,1-trifluoropropan-2-amine (8.72mg, 0.077 mmol), HATU (29.3 mg, 0.077 mmol), and triethylamine (0.014 mL. 0.103 mmol) in DMF (1 mL) and stirred overnight. Purified the reaction mixture by HPLC eluting with 15-40% ACN gradient in water (TFA) to give the title compound, as its TFA salt, (17% yield) as an off-white solid. $^1$H NMR (400 MHz, DMSO-$d_6$) δ ppm 0.73-0.90 (m, 4 H) 1.34-1.42 (m, 4 H) 1.88-2.00 (m, 1 H) 4.73-4.89 (m, 1 H) 7.54-7.67 (m, 2 H) 8.05-8.10 (m, 1 H) 8.25-8.36 (m, 2 H) 8.50-8.57 (m, 1 H) 9.06-9.12 (m, 1 H) 11.05-11.11 (m, 1 H); ESI-MS: m/z 407.5 [M+H]$^+$.

EXAMPLE 44

4-(2-(cyclopropanecarboxamido)imidazo[1,2-b]pyridazin-6-yl)-N-(2,2,2-trifluoroethyl)thiophene-2-carboxamide

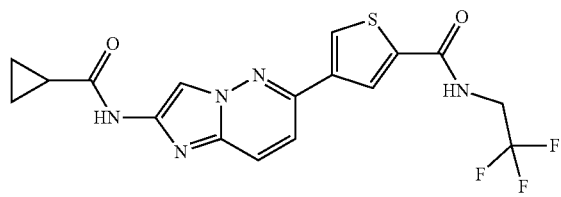 [SMILES: O=C(NCC(F)(F)F)c1cc(-c2ccc3nc(NC(=O)C4CC4)cn3n2)cs1]

Combined N-(6-chloroimidazo[1,2-b]pyridazin-2-yl)cyclopropanecarboxamide (70 mg, 0.296 mmol), 4-(4,4,5,5-tetramethyl-1,3,2-dioxaborolan-2-yl)-N-(2,2,2-trifluoroethyl)thiophene-2-carboxamide (114 mg, 0.340 mmol), potassium carbonate (164 mg, 1.183 mmol), and Pd-118 (JM catalyst) (16.13 mg, 0.024 mmol) in dioxane (1479 µl) and water (426 µl, 23.66 mmol). The mixture was irradiated in a microwave at 135° C. for 30 min. The mixture was then partitioned between EtOAc and water, layers were separated and the aqueous layer was extracted twice more with EtOAc. Organic layers were combined and dried over $Na_2SO_4$, filtered, and concentrated in vacuo and purified by preparative HPLC (SunFire™ C18, 5 µm, 30 mm×75 mm) using a gradient of 20-50% ACN in water (TFA) to give the title compound (8% yield) as a white solid. $^1$H NMR (400 MHz, DMSO-$d_6$) δ ppm 0.71-0.95 (m, 4 H) 1.97 (t, J=5.31 Hz, 1 H) 4.12 (dd, J=9.60, 6.32 Hz, 2 H) 7.77 (d, J=9.60 Hz, 1 H) 8.10 (d, J=9.35 Hz, 1 H) 8.23 (s, 1 H) 8.56 (s, 1 H) 8.61 (s, 1 H) 9.41 (t, J=6.19 Hz, 1 H) 11.24 (s, 1 H); ESI-MS m/z [M+H]$^+$ 410.0.

EXAMPLE 45

4-(2-(cyclopropanecarboxamido)imidazo[1,2-a]pyrazin-6-yl)-N-((1R,2S)-2-hydroxycyclohexyl)thiazole-2-carboxamide

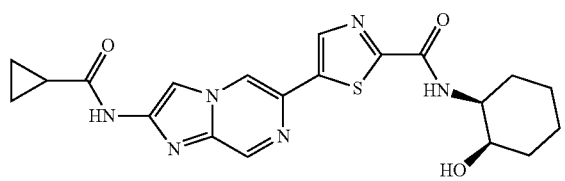 [SMILES: O=C(N[C@H]1CCCC[C@H]1O)c1ncc(-c2cn3cc(NC(=O)C4CC4)nc3cn2)s1]

Combined EDC (87 mg, 0.455 mmol), DIEA (119 0.683 mmol), HOBT (45.3 mg, 0.296 mmol) and 4-(2-(cyclopropanecarboxamido)imidazo[1,2-a]pyrazin-6-yl)thiazole-2-carboxylic acid (75 mg, 0.228 mmol) in DMF (455 µl). After 10 minutes, (1R,2S)-2-aminocyclohexanol (52.5 mg, 0.455 mmol) was added and stirred overnight at room temperature, then purified the reaction mixture by preparative HPLC (SunFire™ C18, 5 µm, ID 30 mm×75 mm) using a gradient of 35-50% ACN in water (TFA) to give title compound, as its TFA salt, (14% yield) as a yellow solid. $^1$H NMR (400 MHz, DMSO-d6) δ ppm 0.80-0.88 (m, 4 H) 1.35 (br. s., 2 H) 1.48-1.80 (m, 7 H) 1.98 (br. s., 1 H) 3.88 (br. s., 2 H) 7.92 (d, J=8.08 Hz, 1 H) 8.39 (d, J=11.87 Hz, 2 H) 8.96 (s, 1 H) 9.33 (s, 1 H) 11.30 (s, 1 H); ESI-MS: m/z [M+H]$^+$ 427.4.

EXAMPLE 46

4-(2-(cyclopropanecarboxamido)imidazo[1,2-a]pyrazin-6-yl)-N-(4-hydroxytetrahydrofuran-3-yl)thiazole-2-carboxamide

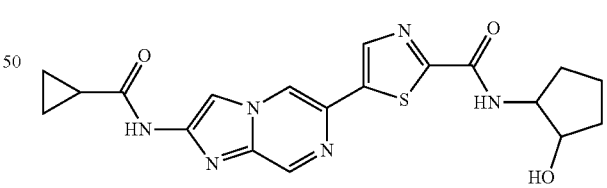

Prepared by the methodology of Example 45 using 4-aminotetrahydrofuran-3-ol to give the title compound, as its TFA salt, (30% yield) as a white solid. $^1$H NMR (400 MHz, DMSO-d6) δ ppm 0.83-0.87 (m, 4 H) 1.93-2.01 (m, 1 H) 3.56 (dd, J=9.35, 2.78 Hz, 1 H) 3.74 (dd, J=9.09, 3.54 Hz, 1 H) 4.01 (ddd, J=17.05, 9.22, 5.56 Hz, 2 H) 4.22-4.29 (m, 1 H) 4.34 (br. s., 1 H) 5.41 (br. s., 1 H) 8.30 (s, 1 H) 8.39 (s, 1 H) 8.74 (d, J=7.58 Hz, 1 H) 8.95-8.98 (m, 1 H) 9.27-9.31 (m, 1 H) 11.32 (s, 1 H); ESI-MS: m/z [M+H]$^+$ 415.4.

EXAMPLE 47

(R)-N-(6-(2-(2-(trifluoromethyl)pyrrolidine-1-carbonyl)thiazol-4-yl)imidazo[1,2-a]pyrazin-2-yl)cyclopropanecarboxamide

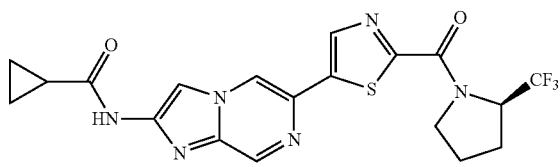 [SMILES: O=C(Nc1cn2cc(-c3cnc(C(=O)N4CCC[C@@H]4C(F)(F)F)s3)ncc2n1)C1CC1]

Prepared by the methodology of Example 45 using (R)-2-(trifluoromethyl)pyrrolidine to give the title compound, as its TFA salt, (23% yield) as a tan solid. $^1$H NMR (400 MHz, DMSO-d6) δ ppm 0.80-0.88 (m, 4 H) 1.98 (br. s., 1 H) 2.10 (br. s., 4 H) 4.24 (br. s., 1 H) 4.36-4.46 (m, 1 H) 5.06-5.17 (m, 1 H) 8.38-8.46 (m, 2 H) 8.96 (s, 1 H) 9.34 (s, 1 H) 11.29 (s, 1 H); ESI-MS: m/z [M+H]$^+$ 451.4.

EXAMPLE 48

(S)-4-(2-(cyclopropanecarboxamido)imidazo[1,2-a]pyrazin-6-yl)-N-(tetrahydro-2H-pyran-3-yl)thiazole-2-carboxamide

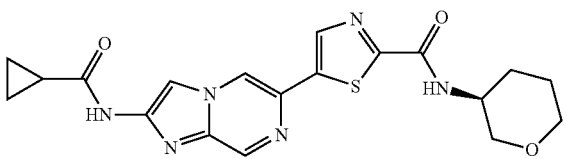 [SMILES: O=C(N[C@H]1CCCOC1)c1ncc(-c2cn3cc(NC(=O)C4CC4)nc3cn2)s1]

Prepared by the methodology of Example 45 using (S)-tetrahydro-2H-pyran-3-amine to give the title compound, as its TFA salt, (19% yield) as a tan solid. $^1$H NMR (400 MHz, DMSO-d6) δ ppm 0.80-0.88 (m, 4 H) 1.61 (d, J=11.12 Hz, 1 H) 1.69-1.79 (m, 2 H) 1.97 (d, J=5.81 Hz, 2 H) 3.38-3.44 (m, 2 H) 3.72-3.85 (m, 2 H) 3.96 (dd, J=8.46, 4.42 Hz, 1 H) 8.32 (s, 1 H) 8.39 (s, 1 H) 8.53 (d, J=8.59 Hz, 1 H) 8.97 (s, 1 H) 9.28 (s, 1 H) 11.32 (s, 1 H); ESI-MS: m/z [M+H]$^+$ 413.4.

EXAMPLE 49

(S)-4-(2-(cyclopropanecarboxamido)imidazo[1,2-a]pyrazin-6-yl)-N-(tetrahydrofuran-3-yl)thiazole-2-carboxamide

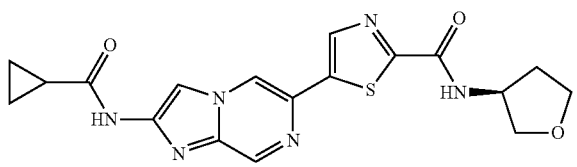 [SMILES: O=C(N[C@H]1CCOC1)c1ncc(-c2cn3cc(NC(=O)C4CC4)nc3cn2)s1]

Prepared by the methodology of Example 45 using (S)-tetrahydrofuran-3-amine to give the title compound, as its TFA salt, (22% yield) as a beige solid. $^1$H NMR (400 MHz, DMSO-d6) δ ppm 0.81-0.89 (m, 4 H) 1.92-2.07 (m, 2 H) 2.17-2.29 (m, 1 H) 3.66-3.79 (m, 2 H) 3.84-3.97 (m, 2 H) 4.53 (d, J=7.07 Hz, 1 H) 8.30 (s, 1 H) 8.39 (s, 1 H) 8.84 (d, J=7.07 Hz, 1 H) 8.97 (s, 1 H) 9.29 (d, J=1.26 Hz, 1 H) 11.32 (s, 1 H); ESI-MS: m/z [M+H]$^+$ 399.3.

EXAMPLE 50

4-(2-(cyclopropanecarboxamido)imidazo[1,2-a]pyridin-6-yl)-N-(2,2,2-trifluoroethyl)-1H-imidazole-2-carboxamide

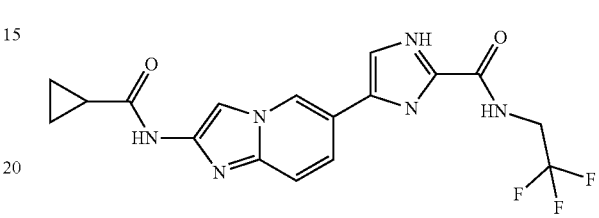

Combined 4-bromo-N-(2,2,2-trifluoroethyl)-1H-imidazole-2-carboxamide (100 mg, 0.368 mmol), (2-(cyclopropanecarboxamido)imidazo[1,2-a]pyridin-6-yl)boronic acid (241 mg, 0.985 mmol), and PdCl$_2$(dppf) (13.45 mg, 0.018 mmol) in dioxane (1634 μl) and saturated aqueous sodium bicarbonate (817 μl). The mixture was microwaved at 115° C. for 30 minutes then PdCl$_2$(dppf) (13.45 mg, 0.018 mmol) and N-(6-(4,4,5,5-tetramethyl-1,3,2-dioxaborolan-2-yl)imidazo[1,2-a]pyridin-2-yl)cyclopropanecarboxamide (241 mg, 0.735 mmol) were added and microwaved at 115° C. for 60 minutes. The reaction mixture was purified preparative HPLC (SunFire™ C18, 5 μm, ID 30 mm×75 mm) using a gradient of 20-25% ACN in water (TFA) to give the title compound, as its TFA salt, (17% yield) as a white solid. $^1$H NMR (400 MHz, DMSO-d6) δ ppm 0.75-0.87 (m, 4 H) 1.90-1.99 (m, 1 H) 4.01-4.13 (m, 2 H) 7.48 (d, J=10.11 Hz, 1 H) 7.74 (d, J=8.84 Hz, 1 H) 7.81 (s, 1 H) 8.02 (br. s., 1 H) 8.91-9.04 (m, 2 H) 11.02 (s, 1 H); ESI-MS: m/z [M+H]$^+$ 393.4.

EXAMPLE 51

5-(2-(cyclopropanecarboxamido)imidazo[1,2-a]pyridin-6-yl)-N-(2,2,2-trifluoroethyl)-1H-pyrazole-3-carboxamide

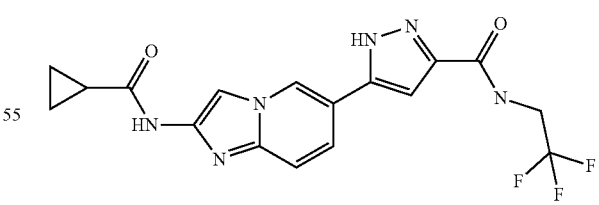

Combined (2-(cyclopropanecarboxamido)imidazo[1,2-a]pyridin-6-yl)boronic acid (289 mg, 1.178 mmol), 5-chloro-N-(2,2,2-trifluoroethyl)-1H-pyrazole-3-carboxamide (100mg, 0.439 mmol), and PdCl$_2$(dppf) (16.08 mg, 0.022 mmol) in dioxane (1953 μl) and saturated aqueous sodium bicarbonate (976 μl). The reaction mixture was microwaved at 115° C. for 30 minutes and then microwaved at 125° C.

for 30 minutes. The reaction mixture was purified by preparative HPLC (SunFire™ C18, 5 μm, ID 30 mm×75 mm) using a gradient of 25-25% ACN in water (TFA) to give the title compound, as its TFA salt, (6% yield) as a beige solid. ¹H NMR (400 MHz, DMSO-d6) δ ppm 0.75-0.90 (m, 4 H) 1.95 (br. s., 1 H) 4.07 (br. s., 2 H) 7.19 (br. s., 1 H) 7.54 (d, J=7.58 Hz, 1 H) 7.65 (d, J=9.35 Hz, 1 H) 8.08 (br. s., 1 H) 9.01 (br. s., 1 H) 11.05 (br. s., 1 H); ESI-MS: m/z [M+H]⁺ 393.3.

EXAMPLE 52

(R)-N-(6-(3-(2-(trifluoromethyl)pyrrolidine-1-carbonyl)-1H-pyrazol-5-yl)imidazo[1,2-a]pyridin-2-yl)cyclopropanecarboxamide

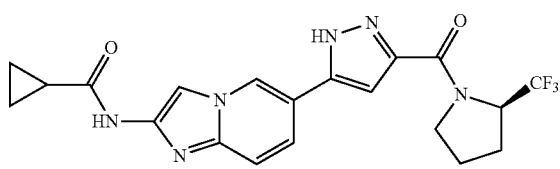 [SMILES: O=C(Nc1cn2cc(-c3cc(C(=O)N4CCC[C@@H]4C(F)(F)F)n[nH]3)ccc2n1)C1CC1]

Prepare by the methodology of Example 51 using (R)-(5-chloro-1H-pyrazol-3-yl)(2-(trifluoromethyl)pyrrolidin-1-yl)methanone to give the title compound, as its TFA salt, (5% yield) as a beige solid. ¹H NMR (400 MHz, DMSO-d6) δ ppm 0.70-0.93 (m, 4 H) 1.89-2.22 (m, 5 H) 3.97 (br. s., 2 H) 5.11 (br. s., 1 H) 7.44-7.81 (m, 3 H) 8.06 (br. s., 1 H) 9.07 (br. s., 1 H) 11.03 (br. s., 1 H) 13.71-13.93 (m, 1 H); ESI-MS: m/z [M+H]⁺ 433.4.

EXAMPLE 53

(S)-5-(2-(cyclopropanecarboxamido)imidazo[1,2-a]pyridin-6-yl)-N-(tetrahydrofuran-3-yl)-1H-pyrazole-3-carboxamide

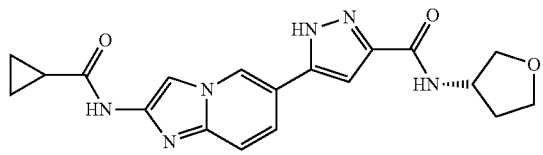

Prepare by the methodology of Example 51 using (S)-5-chloro-N-(tetrahydrofuran-3-yl)-1H-pyrazole-3-carboxamide to give the title compound, as its TFA salt, (16% yield) as a pink solid. ¹H NMR (400 MHz, DMSO-d6) δ ppm 0.75-0.89 (m, 4 H) 1.93 (d, J=4.04 Hz, 2 H) 2.16 (dd, J=12.88, 7.07 Hz, 1 H) 3.59 (dd, J=8.97, 4.42 Hz, 1 H) 3.69-3.77 (m, 1 H) 3.82-3.89 (m, 2 H) 4.45 (br. s., 1 H) 7.17-7.26 (m, 1 H) 7.56 (br. s., 1 H) 7.68 (d, J=8.59 Hz, 1 H) 8.09 (br. s., 1 H) 8.50 (br. s., 1 H) 9.01 (br. s., 1 H) 11.10 (br. s., 1 H); ESI-MS: m/z [M+H] 381.4.

EXAMPLE 54

N-{6-[5-(morpholine-4-carbonyl)thiophen-3-yl]imidazo[1,2-a]pyridin-2-yl}cyclopropanecarboxamide

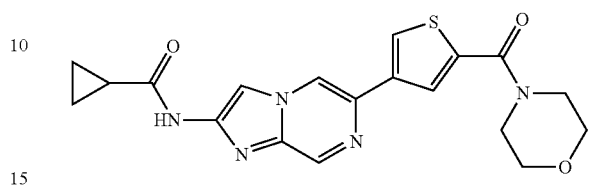

Combined 4-(2-(cyclopropanecarboxamido)imidazo[1,2-a]pyridin-6-yl)thiophene-2-carboxylic acid (50 mg, 0.153 mmol), morpholine (17.30 μl, 0.199 mmol), 1-(3-dimethylaminopropyl)-3-ethylcarbodiimide hydrochloride (58.6 mg, 0.305 mmol), and HOBT (26.8 mg, 0.199 mmol) in DMF (305 μl) then added N,N-diisopropylethylamine (80 μl, 0.458 mmol) at 23° C. The reaction mixture was stirred at 23° C. for 16 hours. The product was purified by preparative HPLC (Phenomenex Gemini™ C18, 5 μm, ID30×75 mm column) using a gradient eluent of 15-40% ACN in water (TFA) to give the title compound, as its TFA salt, (66% yield) as an off-white solid. ¹H NMR (400 MHz, DMSO-d₆) δ ppm 0.79-0.89 (m, 4 H) 1.93 (quin, J=6.19 Hz, 1 H) 3.61-3.75 (m, 8 H) 7.56 (d, J=9.35 Hz, 1 H) 7.75-7.81 (m, 1 H) 7.84 (d, J=1.26 Hz, 1 H) 8.02 (s, 1 H) 8.12 (d, J=1.26 Hz, 1 H) 9.07 (s, 1 H) 11.19 (s, 1 H); ESI-MS m/z [M+H]⁺ 397.3.

EXAMPLE 55

4-(2-(cyclopropanecarboxamido)imidazo[1,2-a]pyridin-6-yl)-N-(2,2-difluoroethyl)thiophene-2-carboxamide

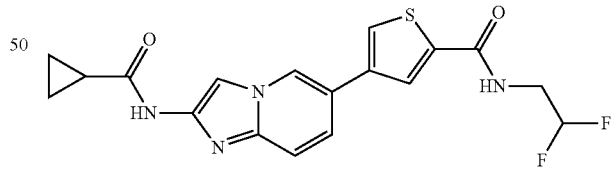

Prepared by the methodology of Example 54 using 4-(2-(cyclopropanecarboxamido)imidazo[1,2-a]pyridin-6-yl)thiophene-2-carboxylic acid and 2,2-difluoroethanamine to give the title compound, as its TFA salt, (72% yield) as an off-white solid. ¹H NMR (400 MHz, DMSO-d₆) δ ppm 0.75-0.91 (m, 4 H) 1.90-2.01 (m, 1 H) 3.60-3.86 (m, 2 H) 5.95-6.34 (m, 1 H) 7.53-7.71 (m, 2 H) 8.02-8.10 (m, 1 H) 8.13 (d, J=1.26 Hz, 1 H) 8.27 (d, J=1.26 Hz, 1 H) 8.91-9.03 (m, 2 H) 11.14 (s, 1 H); ESI-MS m/z [M+H]⁺ 391.3.

EXAMPLE 56

4-(2-(cyclopropanecarboxamido)imidazo[1,2-a]pyridin-6-yl)-N-(1,1,1-trifluoro-2-methylpropan-2-yl)thiophene-2-carboxamide

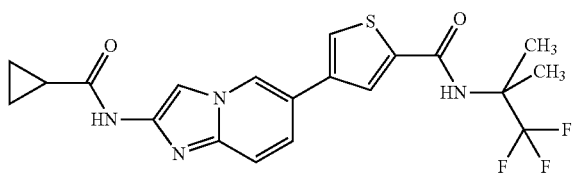 [SMILES: CC(C)(NC(=O)c1cc(-c2ccc3nc(NC(=O)C4CC4)cn3c2)cs1)C(F)(F)F]

Prepared by the methodology of Example 54 using 4-(2-(cyclopropanecarboxamido)imidazo[1,2-a]pyridin-6-yl)thiophene-2-carboxylic acid and 1,1,1-trifluoro-2-methylpropan-2-amine to give the title compound, as its TFA salt, (3% yield) as an off-white solid. $^1$H NMR (400 MHz, DMSO-$d_6$) δ ppm 0.78-0.85 (m, 4 H) 1.64 (s, 7 H) 7.49-7.62 (m, 2 H) 8.02-8.12 (m, 2 H) 8.17 (s, 1 H) 8.33 (d, J=1.26 Hz, 1 H) 8.91 (s, 1 H) 11.04 (s, 1 H); ESI-MS m/z [M+H]$^+$ 437.4.

EXAMPLE 57

4-(2-(cyclopropanecarboxamido)imidazo[1,2-a]pyridin-6-yl)-N-(2,2-difluoropropyl)thiophene-2-carboxamide

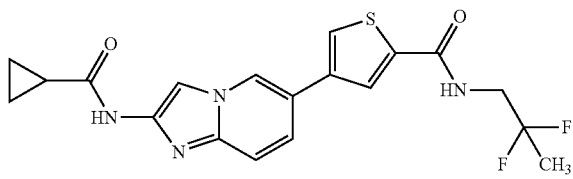 [SMILES: CC(F)(F)CNC(=O)c1cc(-c2ccc3nc(NC(=O)C4CC4)cn3c2)cs1]

Prepared by the methodology of Example 54 using 2,2-difluoropropan-1-amine, HCl to give the title compound, as its TFA salt, (19% yield) as an off-white solid. $^1$H NMR (400 MHz, DMSO-$d_6$) δ ppm 0.79-0.86 (m, 4 H) 1.65 (t, J=19.07 Hz, 3 H) 1.95 (br. s., 1 H) 3.71-3.79 (m, 2 H) 7.50-7.65 (m, 2 H) 8.05 (s, 1 H) 8.11 (d, J=1.26 Hz, 1 H) 8.32 (d, J=1.52 Hz, 1 H) 8.89-8.97 (m, 2 H) 11.06 (s, 1 H); ESI-MS m/z [M+H]$^+$ 405.4.

EXAMPLE 58

N-(6-(5-(4-methoxypiperidine-1-carbonyl)thiophen-3-yl)imidazo[1,2-a]pyridin-2-yl)cyclopropanecarboxamide

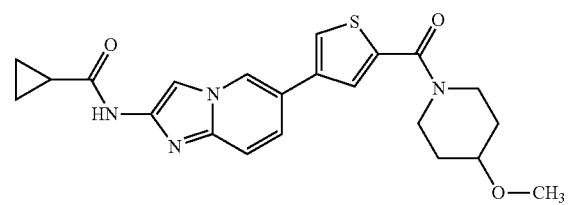 [SMILES: COC1CCN(C(=O)c2cc(-c3ccc4nc(NC(=O)C5CC5)cn4c3)cs2)CC1]

Prepared by the methodology of Example 54 using 4-(2-(cyclopropanecarboxamido)imidazo[1,2-a]pyridin-6-yl)thiophene-2-carboxylic acid and 4-methoxypiperidine (27.4 mg, 0.238 mmol) to give the title compound, (15% yield) as a beige solid. $^1$H NMR (400 MHz, DMSO-$d_6$) δ ppm 0.76-0.86 (m, 4 H) 1.50-1.57 (m, 1 H) 1.86-1.97 (m, 4 H) 3.23-3.28 (m, 3 H) 3.86-3.97 (m, 4 H) 6.58 (d, J=5.56 Hz, 1 H) 7.47 (d, J=9.35 Hz, 1 H) 7.64 (dd, J=9.35, 1.77 Hz, 1 H) 7.79 (d, J=1.26 Hz, 1 H) 8.00-8.07 (m, 2 H) 9.01 (s, 1 H) 11.00 (s, 1 H); ESI-MS m/z [M+H]$^+$ 425.4.

EXAMPLE 59

4-(2-(cyclopropanecarboxamido)imidazo[1,2-a]pyridin-6-yl)-N-(1,1,1-trifluoropropan-2-yl)thiophene-2-carboxamide

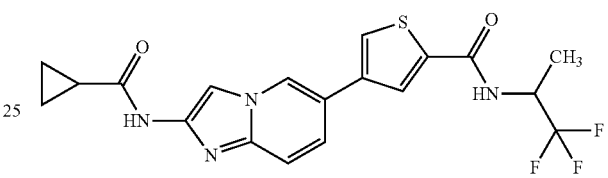

Prepared by the methodology of Example 54 using 4-(2-(cyclopropanecarboxamido)imidazo[1,2-a]pyridin-6-yl)thiophene-2-carboxylic acid and 1,1,1-trifluoropropan-2-amine to give the title compound, as its TFA salt, (51% yield) as an off-white solid. $^1$H NMR (400 MHz, DMSO-$d_6$) δ ppm 0.75-0.91 (m, 4 H) 1.39 (d, J=7.07 Hz, 3 H) 1.87-1.99 (m, 1 H) 4.70-4.94 (m, 1 H) 7.54-7.63 (m, 1 H) 7.63-7.70 (m, 1 H) 8.06 (s, 1 H) 8.16 (d, J=1.52 Hz, 1 H) 8.34 (d, J=1.26 Hz, 1 H) 8.92-9.04 (m, 2 H) 11.13 (s, 1 H); ESI-MS m/z [M+H]$^+$ 423.3.

EXAMPLE 60

N-(6-(5-(2-(trifluoromethyl)pyrrolidine-1-carbonyl)thiophen-3-yl)imidazo[1,2-a]pyridin-2-yl)cyclopropanecarboxamide

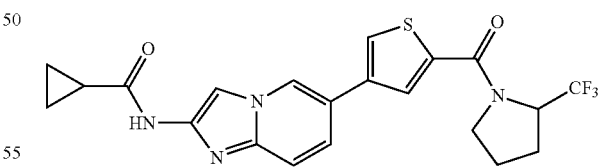

Prepared by the methodology of Example 54 using 4-(2-(cyclopropanecarboxamido)imidazo[1,2-a]pyridin-6-yl)thiophene-2-carboxylic acid and 2-(trifluoromethyl)pyrrolidine to give the title compound, as its TFA salt, (53% yield) as an off-white solid. $^1$H NMR (400 MHz, DMSO-$d_6$) δ ppm 0.81-0.91 (m, 5 H) 1.90-1.98 (m, 1 H) 2.00-2.14 (m, 3 H) 3.84-3.96 (m, 2 H) 5.14 (t, J=7.71 Hz, 1 H) 7.53 (d, J=9.35 Hz, 1 H) 7.64-7.80 (m, 1 H) 8.01 (s, 1 H) 8.12 (d, J=1.26 Hz, 1 H) 8.21 (d, J=1.01 Hz, 1 H) 9.12 (s, 1 H) 11.10 (s, 1 H); ESI-MS m/z [M+H]$^+$ 449.3.

EXAMPLE 61

(S)-N-(6-(5-(2-(trifluoromethyl)pyrrolidine-1-carbonyl)thiophen-3-yl)imidazo[1,2-a]pyridin-2-yl)cyclopropanecarboxamide

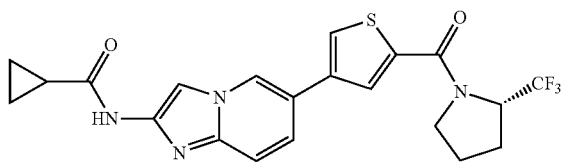 [SMILES: O=C(Nc1cn2cc(-c3csc(C(=O)N4CCCC4C(F)(F)F)c3)ccc2n1)C1CC1]

Prepared by the methodology of Example 54 using 4-(2-(cyclopropanecarboxamido)imidazo[1,2-a]pyridin-6-yl)thiophene-2-carboxylic acid and (S)-2-(trifluoromethyl)pyrrolidine to give the title compound (32% yield) as an off-white solid. $^1$H NMR (400 MHz, DMSO-$d_6$) δ ppm 0.76-0.93 (m, 4 H) 1.90-1.98 (m, 1 H) 1.98-2.14 (m, 3 H) 3.87-4.00 (m, 1 H) 4.05 (t, J=8.21 Hz, 1 H) 4.35-4.47 (m, 1 H) 5.10-5.21 (m, 1 H) 7.48 (d, J=9.35 Hz, 1 H) 7.68 (dd, J=9.35, 1.77 Hz, 1 H) 7.92-8.07 (m, 1 H) 8.09-8.16 (m, 1 H) 8.18 (d, J=1.01 Hz, 1 H) 9.08 (s, 1 H) 11.01 (s, 1 H); ESI-MS m/z [M+H]$^+$ 449.3.

EXAMPLE 62

(R)-N-(6-(5-(2-(trifluoromethyl)pyrrolidine-1-carbonyl)thiophen-3-yl)imidazo[1,2-a]pyridin-2-yl)cyclopropanecarboxamide

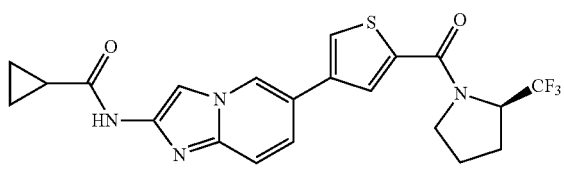 [SMILES: O=C(Nc1cn2cc(-c3csc(C(=O)N4CCC[C@@H]4C(F)(F)F)c3)ccc2n1)C1CC1]

Prepared by the methodology of Example 54 using 4-(2-(cyclopropanecarboxamido)imidazo[1,2-a]pyridin-6-yl)thiophene-2-carboxylic acid and (R)-2-(trifluoromethyl)pyrrolidine to give the title compound (27% yield) as an off-white solid. $^1$H NMR (400 MHz, DMSO-$d_6$) δ ppm 0.74-0.88 (m, 4 H) 1.91-2.02 (m, 1 H) 2.02-2.25 (m, 3 H) 4.11 (d, J=4.80 Hz, 3 H) 7.49 (d, J=9.35 Hz, 1 H) 7.68 (dd, J=9.35, 1.77 Hz, 1 H) 8.01 (s, 1 H) 8.12 (d, J=1.26 Hz, 1 H) 8.19 (d, J=1.26 Hz, 1 H) 8.25 (s, 1 H) 9.09 (s, 1 H) 11.01 (s, 1 H); ESI-MS m/z [M+H]$^+$ 449.3.

EXAMPLE 63

4-(2-(cyclopropanecarboxamido)imidazo[1,2-a]pyridin-6-yl)-N-isobutylthiophene-2-carboxamide

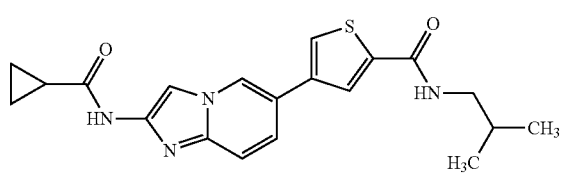

Prepared by the methodology of Example 54 using 4-(2-(cyclopropanecarboxamido)imidazo[1,2-a]pyridin-6-yl)thiophene-2-carboxylic acid and 2-methylpropan-1-amine to give the title compound, as its TFA salt, (57% yield) as a white solid. $^1$H NMR (400 MHz, DMSO-$d_6$) δ ppm 0.79-0.89 (m, 4 H) 0.91 (d, J=6.82 Hz, 6 H) 1.80-1.90 (m, 1 H) 1.91-2.01 (m, 1 H) 3.09 (t, J=6.32 Hz, 2 H) 7.51-7.65 (m, 2 H) 8.05 (d, J=1.01 Hz, 2 H) 8.20 (d, J=1.26 Hz, 1 H) 8.51-8.58 (m, 1 H) 8.90 (s, 1 H) 11.05 (s, 1 H); ESI-MS m/z [M+H]$^+$ 383.3.

EXAMPLE 64

4-(2-(cyclopropanecarboxamido)imidazo[1,2-a]pyridin-6-yl)-N-(2-fluoroethyl)thiophene-2-carboxamide

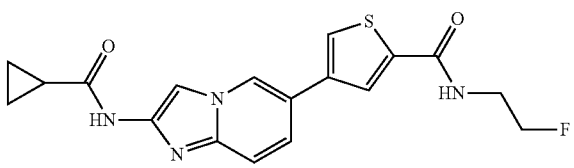 [SMILES: O=C(NCCF)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and 2-fluoroethanamine, HCl to give the title compound, as its TFA salt, (32% yield) as an off-white solid. $^1$H NMR (400 MHz, DMSO-$d_6$) δ ppm 0.78-0.91 (m, 4 H) 1.88-1.98 (m, 1 H) 3.54-3.67 (m, 2 H) 4.50 (t, J=5.05 Hz, 1 H) 4.62 (t, J=5.05 Hz, 1 H) 7.45-7.61 (m, 2 H) 8.02-8.10 (m, 2 H) 8.23 (d, J=1.26 Hz, 1 H) 8.80 (t, J=5.56 Hz, 1 H) 8.89 (s, 1 H) 11.02 (s, 1 H); ESI-MS m/z [M+H]$^+$ 373.3.

EXAMPLE 65

4-(2-(cyclopropanecarboxamido)imidazo[1,2-a]pyridin-6-yl)-N-(2-fluoroethyl)thiophene-2-carboxamide

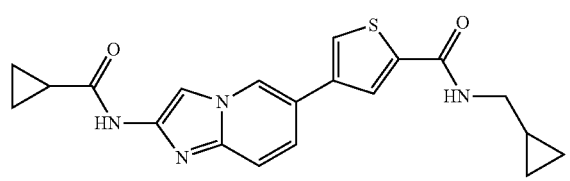 [SMILES: O=C(NCC1CC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and cyclopropylmethanamine HCl to give the title compound, as its TFA salt, (30% yield) as an off-white solid. $^1$H NMR (400 MHz, DMSO-$d_6$) δ ppm 0.21-0.31 (m, 2 H) 0.46-0.56 (m, 1 H) 0.76-0.86 (m, 4 H) 0.99-1.13 (m, 1 H) 1.92-2.02 (m, 1 H) 3.14 (t, J=6.19 Hz, 2 H) 7.48-7.60 (m, 2 H) 8.03-8.15 (m, 2 H) 8.20 (d, J=1.52 Hz, 1 H) 8.64 (t, J=5.68 Hz, 1 H) 8.90 (s, 1 H) 11.01 (s, 1 H); ESI-MS m/z [M+H]$^+$ 381.3.

EXAMPLE 66

4-(2-(cyclopropanecarboxamido)imidazo[1,2-a]pyridin-6-yl)-N-(tetrahydro-2H-pyran-4-yl)thiophene-2-carboxamide

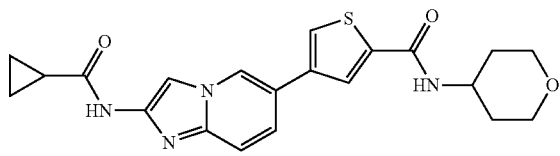 [SMILES: O=C(NC1CCOCC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and tetrahydro-2H-pyran-4-amine to give the title compound (35% yield) as an off-white solid. $^1$H NMR (400 MHz, DMSO-$d_6$) δ ppm 0.76-0.92 (m, 4 H) 1.57 (qd, J=12.00, 4.42 Hz, 2 H) 1.76-1.83 (m, 2 H) 1.91-1.99 (m, 1 H) 3.37-3.44 (m, 2 H) 3.84-4.05 (m, 3 H) 7.47-7.62 (m, 2 H) 8.05 (d, J=1.52 Hz, 2 H) 8.22 (d, J=1.52 Hz, 1 H) 8.41 (d, J=7.58 Hz, 1 H) 8.90 (s, 1 H) 11.02 (s, 1 H); ESI-MS m/z [M+H]$^+$ 411.3.

EXAMPLE 67

4-(2-(cyclopropanecarboxamido)imidazo[1,2-a]pyridin-6-yl)-N-(tetrahydro-2H-pyran-3-yl)thiophene-2-carboxamide

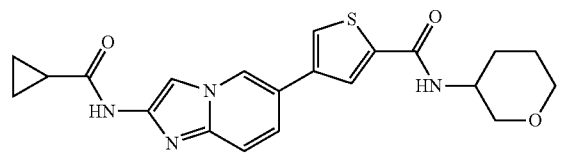

Prepared by the methodology of Example 54 using 4-(2-(cyclopropanecarboxamido)imidazo[1,2-a]pyridin-6-yl)thiophene-2-carboxylic acid and tetrahydro-2H-pyran-3-amine to give the title compound (35% yield) as an off-white solid. $^1$H NMR (400 MHz, DMSO-$d_6$) δ ppm 0.74-0.89 (m, 4 H) 1.54-1.67 (m, 2 H) 1.67-1.79 (m, 1 H) 1.91-1.99 (m, 2 H) 3.19 (br. s., 2 H) 3.72-3.93 (m, 3 H) 7.48-7.59 (m, 2 H) 8.01-8.11 (m, 2 H) 8.25 (d, J=1.52 Hz, 1 H) 8.33 (d, J=7.83 Hz, 1 H) 8.89 (s, 1 H) 11.01 (s, 1 H); ESI-MS m/z [M+H]$^+$ 411.3.

EXAMPLE 68

(S)-4-(2-(cyclopropanecarboxamido)imidazo[1,2-a]pyridin-6-yl)-N-(tetrahydro-2H-pyran-3-yl)thiophene-2-carboxamide

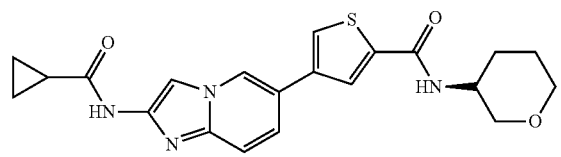 [SMILES: O=C(NC1CCCOC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (S)-tetrahydro-2H-pyran-3-amine, HCl to give the title compound (37% yield) as an off-white solid. $^1$H NMR (400 MHz, DMSO-$d_6$) δ ppm 0.76-0.88 (m, 4 H) 1.54-1.68 (m, 2 H) 1.73 (d, J=10.61 Hz, 1 H) 1.95 (br. s., 2 H) 3.15-3.25 (m, 1 H) 3.73-3.94 (m, 3 H) 7.46-7.62 (m, 2 H) 8.01-8.09 (m, 2 H) 8.25 (d, J=1.52 Hz, 1 H) 8.34 (d, J=7.58 Hz, 1 H) 8.90 (s, 1 H) 11.02 (s, 1 H); ESI-MS m/z [M+H]$^+$ 411.3.

EXAMPLE 69

(R)-4-(2-(cyclopropanecarboxamido)imidazo[1,2-a]pyridin-6-yl)-N-(tetrahydro-2H-pyran-3-yl)thiophene-2-carboxamide

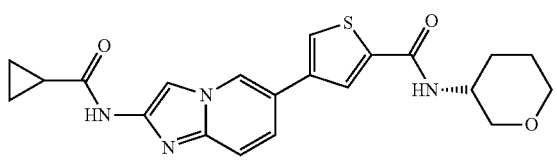

Prepared by the methodology of Example 54 using 4-(2-(cyclopropanecarboxamido)imidazo[1,2-a]pyridin-6-yl)thiophene-2-carboxylic acid and (R)-tetrahydro-2H-pyran-3-amine, HCl to give the title compound (29% yield) as an off-white solid. $^1$H NMR (400 MHz, DMSO-$d_6$) δ ppm 0.76-0.85 (m, 4 H) 1.54-1.64 (m, 2 H) 1.68-1.77 (m, 1 H) 1.91-2.01 (m, 2 H) 3.20 (dd, J=10.48, 8.97 Hz, 1 H) 3.69-3.88 (m, 2 H) 7.45-7.63 (m, 2 H) 8.02-8.13 (m, 2 H) 8.23-8.38 (m, 3 H) 8.89 (s, 1 H) 11.01 (s, 1 H); ESI-MS m/z [M+H]$^+$ 411.3.

EXAMPLE 70

4-(2-(cyclopropanecarboxamido)imidazo[1,2-a]pyridin-6-yl)-N-(tetrahydrofuran-3-yl)thiophene-2-carboxamide

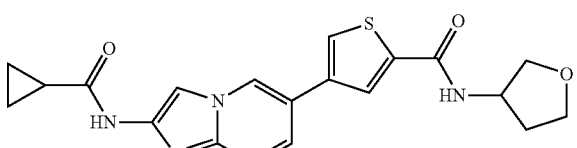

Prepared by the methodology of Example 54 using 4-(2-(cyclopropanecarboxamido)imidazo[1,2-a]pyridin-6-yl)thiophene-2-carboxylic acid and tetrahydrofuran-3-amine (9.58 mg, 0.110 mmol) to give the title compound (14% yield) as an off-white solid. $^1$H NMR (400 MHz, DMSO-$d_6$) δ ppm 0.77-0.85 (m, 4 H) 1.87-1.99 (m, 1 H) 2.15-2.25 (m, 1 H) 3.62 (dd, J=8.97, 3.92 Hz, 1 H) 3.74 (td, J=8.21, 5.81 Hz, 1 H) 3.84-3.91 (m, 2 H) 7.48-7.60 (m, 2 H) 8.02-8.08 (m, 2 H) 8.27 (d, J=1.52 Hz, 1 H) 8.64 (d, J=6.57 Hz, 1 H) 8.89 (s, 1 H) 11.02 (s, 1 H); ESI-MS m/z [M+H]$^+$ 397.3.

EXAMPLE 71

(R)-4-(2-(cyclopropanecarboxamido)imidazo[1,2-a]pyridin-6-yl)-N-(tetrahydrofuran-3-yl)thiophene-2-carboxamide

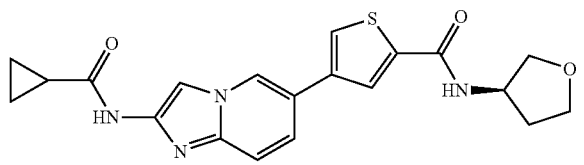 [SMILES: O=C(N[C@@H]1CCOC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (R)-tetrahydrofuran-3-amine, HCl to give the title compound (30% yield) as an off-white solid. $^1$H NMR (400 MHz, DMSO-d$_6$) δ ppm 0.71-0.91 (m, 4 H) 1.83-2.03 (m, 2 H) 2.11-2.25 (m, 1 H) 3.61 (dd, J=8.97, 3.92 Hz, 1 H) 3.73 (td, J=8.15, 5.94 Hz, 1 H) 3.82-3.95 (m, 2 H) 4.04-4.18 (m, 1 H) 4.45 (br. s., 1 H) 7.47-7.63 (m, 1 H) 7.98-8.12 (m, 1 H) 8.26 (d, J=1.52 Hz, 1 H) 8.64 (d, J=6.32 Hz, 1 H) 8.88 (s, 1 H) 11.01 (s, 1 H); ESI-MS m/z [M+H]$^+$ 397.3.

EXAMPLE 72

(S)-4-(2-(cyclopropanecarboxamido)imidazo[1,2-a]pyridin-6-yl)-N-(tetrahydrofuran-3-yl)thiophene-2-carboxamide

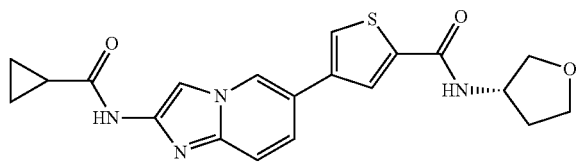 [SMILES: O=C(N[C@H]1CCOC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (S)-tetrahydrofuran-3-amine, HCl to give the title compound (30% yield) as an off-white solid. $^1$H NMR (400 MHz, DMSO-d$_6$) δ ppm 0.75-0.86 (m, 4 H) 1.85-1.99 (m, 2 H) 2.11-2.26 (m, 1 H) 3.61 (dd, J=8.97, 3.92 Hz, 1 H) 3.73 (td, J=8.21, 5.81 Hz, 1 H) 3.82-3.94 (m, 2 H) 4.39-4.55 (m, 1 H) 7.48-7.71 (m, 2 H) 7.99-8.17 (m, 2 H) 8.26 (d, J=1.26 Hz, 1 H) 8.47-8.69 (m, 1 H) 8.89 (s, 1 H) 11.01 (s, 1 H); ESI-MS m/z [M+H]$^+$ 397.3.

EXAMPLE 73

4-(2-(cyclopropanecarboxamido)imidazo[1,2-a]pyridin-6-yl)-N-(2-methoxyethyl)thiophene-2-carboxamide

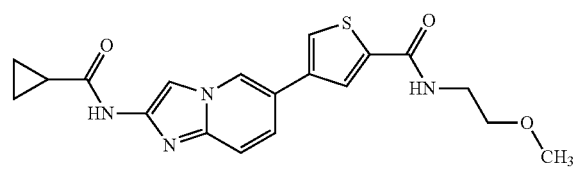 [SMILES: COCCNC(=O)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and 2-methoxyethanamine to give the title compound, as its TFA salt, (26% yield) as a white solid. $^1$H NMR (400 MHz, DMSO-d$_6$) δ ppm 0.77-0.86 (m, 4 H) 1.90-2.00 (m, 1 H) 3.17 (s, 7 H) 7.47-7.66 (m, 2 H) 7.98-8.10 (m, 2 H) 8.17-8.28 (m, 1 H) 8.61 (t, J=5.05 Hz, 1 H) 8.90 (s, 1 H) 11.06 (s, 1 H); ESI-MS m/z [M+H]$^+$ 385.3.

EXAMPLE 74

N-(6-(5-(3,3-difluoropyrrolidine-1-carbonyl)thiophen-3-yl)imidazo[1,2-a]pyridin-2-yl)cyclopropanecarboxamide

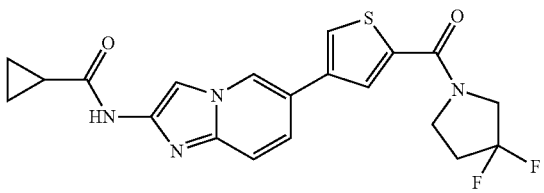 [SMILES: O=C(Nc1cn2cc(-c3csc(C(=O)N4CCC(F)(F)C4)c3)ccc2n1)C1CC1]

Prepared by the methodology of Example 54 using 4-(2-(cyclopropanecarboxamido)imidazo[1,2-a]pyridin-6-yl)thiophene-2-carboxylic acid and 3,3-difluoropyrrolidine, HCl to give the title compound, as its TFA salt, (42% yield) as a white solid. $^1$H NMR (400 MHz, DMSO-d$_6$) δ ppm 0.76-0.95 (m, 4 H) 1.89-2.05 (m, 1 H) 3.78 (br. s., 2 H) 4.14-4.19 (m, 2 H) 4.38 (br. s., 2 H) 7.54 (d, J=9.35 Hz, 1 H) 7.76 (d, J=8.59 Hz, 1 H) 8.02 (s, 2 H) 8.18 (d, J=1.01 Hz, 1 H) 9.10 (s, 1 H) 11.12 (s, 1 H); ESI-MS m/z [M+H]$^+$ 417.3.

EXAMPLE 75

4-(2-(cyclopropanecarboxamido)imidazo[1,2-a]pyridin-6-yl)-N-((tetrahydrofuran-3-yl)methyl)thiophene-2-carboxamide

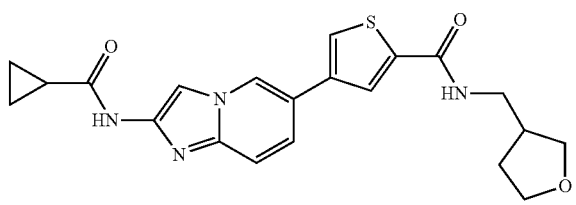 [SMILES: O=C(NCC1CCOC1)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (tetrahydrofuran-3-yl)methanamine to give the title compound, as its TFA salt, (34% yield) as an off-white solid. $^1$H NMR (400 MHz, DMSO-d$_6$) δ ppm 0.77-0.91 (m, 4 H) 1.61 (td, J=12.88, 6.82 Hz, 1 H) 1.92-2.06 (m, 2 H) 3.17-3.28 (m, 2 H) 3.48 (dd, J=8.46, 5.18 Hz, 1 H) 3.54-3.81 (m, 4 H) 7.50-7.59 (m, 1 H) 7.59-7.69 (m, 1 H) 8.02-8.14 (m, 2 H) 8.15-8.24 (m, 1 H) 8.66 (t, J=5.81 Hz, 1 H) 8.93 (s, 1 H) 11.12 (s, 1 H); ESI-MS m/z [M+H]$^+$ 411.3.

EXAMPLE 76

4-(2-(cyclopropanecarboxamido)imidazo[1,2-a]pyridin-6-yl)-N-((1S,2R)-2-hydroxycyclohexyl)thiophene-2-carboxamide

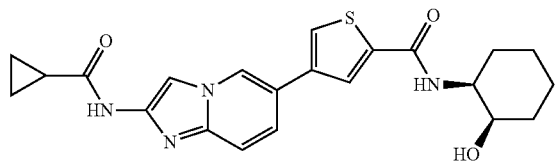 [SMILES: O=C(N[C@H]1CCCC[C@H]1O)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (1R,2S)-2-aminocyclohexanol, HCl to give the title compound (41% yield) as an off-white solid. $^1$H NMR (400 MHz, DMSO-d$_6$) δ ppm 0.77-0.86 (m, 4 H) 1.32 (br. s., 2 H) 1.45-1.58 (m, 2 H) 1.75 (d, J=12.63 Hz, 1 H) 1.91-1.98 (m, 1 H) 3.17 (d, J=5.05 Hz, 4 H) 3.85 (br. s., 2 H) 4.10 (q, J=5.47 Hz, 1 H) 4.74 (d, J=3.79 Hz, 1 H) 7.48-7.64 (m, 2 H) 7.94 (d, J=7.83 Hz, 1 H) 8.01-8.06 (m, 2 H) 8.35 (d, J=1.52 Hz, 1 H) 8.91 (s, 1 H) 11.01 (s, 1 H); ESI-MS m/z [M+H]$^+$ 425.4.

EXAMPLE 77

N-(6-(5-(3,3-difluoroazetidine-1-carbonyl)thiophen-3-yl)imidazo[1,2-a]pyridin-2-yl)cyclopropanecarboxamide

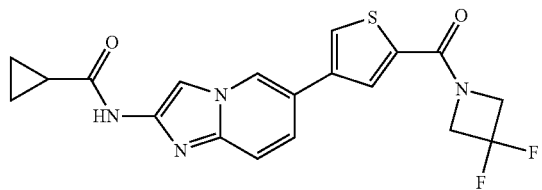 [SMILES: O=C(Nc1cn2cc(-c3csc(C(=O)N4CC(F)(F)C4)c3)ccc2n1)C1CC1]

Prepared by the methodology of Example 54 using 4-(2-(cyclopropanecarboxamido)imidazo[1,2-a]pyridin-6-yl)thiophene-2-carboxylic acid and 3,3-difluoroazetidine, HCl to give the title compound (46% yield) as an off-white solid (17 mg, 46% yield). $^1$H NMR (400 MHz, DMSO-d$_6$) δ ppm 0.74-0.89 (m, 4 H) 1.91-2.00 (m, 1 H) 3.17 (d, J=5.05 Hz, 3 H) 4.10 (q, J=5.39 Hz, 1 H) 7.46-7.71 (m, 2 H) 7.93 (d, J=1.26 Hz, 1 H) 8.01 (s, 1 H) 8.19 (d, J=1.52 Hz, 1 H) 9.05 (s, 1 H) 11.02 (s, 1 H); ESI-MS m/z [M+H]$^+$ 403.3.

EXAMPLE 78

4-(2-(cyclopropanecarboxamido)imidazo[1,2-a]pyridin-6-yl)-N-(3,3,3-trifluoropropyl)thiophene-2-carboxamide

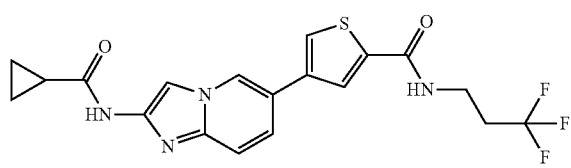 [SMILES: O=C(NCCC(F)(F)F)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and 3,3,3-trifluoropropan-1-amine, HCl to give the title compound (28% yield) as an off-white solid. $^1$H NMR (400 MHz, DMSO-d$_6$) δ ppm 0.77-0.86 (m, 4 H) 1.90-1.99 (m, 1 H) 3.47-3.56 (m, 2 H) 4.11 (q, J=5.31 Hz, 2 H) 7.47-7.59 (m, 2 H) 8.04-8.12 (m, 2 H) 8.15 (d, J=1.52 Hz, 1 H) 8.78 (t, J=5.68 Hz, 1 H) 8.90 (s, 1 H) 11.02 (s, 1 H); ESI-MS m/z [M+H]$^+$ 423.3.

EXAMPLE 79

N-(1-acetylpyrrolidin-3-yl)-4-(2-(cyclopropanecarboxamido)imidazo[1,2-a]pyridin-6-yl)thiophene-2-carboxamide

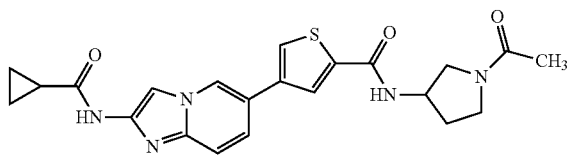 [SMILES: CC(=O)N1CCC(NC(=O)c2cc(-c3ccc4nc(NC(=O)C5CC5)cn4c3)cs2)C1]

Prepared by the methodology of Example 54 using 4-(2-(cyclopropanecarboxamido)imidazo[1,2-a]pyridin-6-yl)thiophene-2-carboxylic acid and 1-(3-aminopyrrolidin-1-yl)ethanone to give the title compound (20% yield) as an off-white solid. $^1$H NMR (400 MHz, DMSO-d$_6$) δ ppm 0.74-0.92 (m, 4 H) 1.24 (br. s., 1 H) 1.87-2.09 (m, 4 H) 2.09-2.24 (m, 1 H) 3.37-3.61 (m, 3 H) 3.78 (dd, J=10.48, 6.44 Hz, 1 H) 4.39-4.54 (m, 1 H) 7.43-7.63 (m, 2 H) 8.00-8.17 (m, 2 H) 8.18-8.45 (m, 1 H) 8.65 (dd, J=14.78, 6.44 Hz, 1 H) 8.90 (d, J=1.77 Hz, 1 H) 11.02 (s, 1 H); ESI-MS m/z [M+H]$^+$ 438.3.

EXAMPLE 80

(S)-4-(2-(cyclopropanecarboxamido)imidazo[1,2-a]pyridin-6-yl)-N-(1,1,1-trifluoropropan-2-yl)thiophene-2-carboxamide

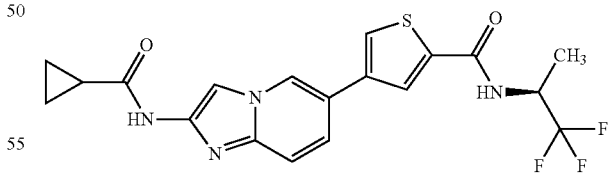

Prepared by the methodology of Example 54 using 4-(2-(cyclopropanecarboxamido)imidazo[1,2-a]pyridin-6-yl)thiophene-2-carboxylic acid and (S)-1,1,1-trifluoropropan-2-amine, HCl to give the title compound (18% yield) as a pale beige solid. $^1$H NMR (400 MHz, DMSO-d$_6$) δ ppm 0.67-0.90 (m, 4 H) 1.39 (d, J=7.07 Hz, 3 H) 1.86-2.00 (m, 1 H) 4.71-4.95 (m, 1 H) 7.42-7.69 (m, 2 H) 8.05 (s, 1 H) 8.14 (d, J=1.26 Hz, 1 H) 8.35 (d, J=1.52 Hz, 1 H) 8.87-9.11 (m, 2 H) 10.98-11.14 (m, 1 H); ESI-MS m/z [M+H]$^+$ 423.3.

EXAMPLE 81

(R)-4-(2-(cyclopropanecarboxamido)imidazo[1,2-a]pyridin-6-yl)-N-(1,1,1-trifluoropropan-2-yl)thiophene-2-carboxamide

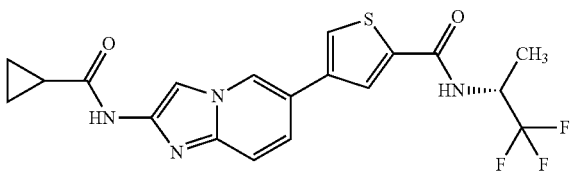 [SMILES: C[C@@H](NC(=O)c1cc(-c2ccc3nc(NC(=O)C4CC4)cn3c2)cs1)C(F)(F)F]

Prepared by the methodology of Example 54 using 4-(2-(cyclopropanecarboxamido)imidazo[1,2-a]pyridin-6-yl)thiophene-2-carboxylic acid and (R)-1,1,1-trifluoropropan-2-amine, HCl to give the title compound (23% yield) as a pale beige solid. $^1$H NMR (400 MHz, DMSO-$d_6$) δ ppm 0.74-0.88 (m, 4 H) 1.33-1.44 (m, 3 H) 1.95 (t, J=5.05 Hz, 1 H) 4.78-4.91 (m, 1 H) 7.47-7.66 (m, 3 H) 8.05 (s, 1 H) 8.14 (d, J=1.52 Hz, 1 H) 8.34 (d, J=1.52 Hz, 1 H) 8.95 (d, J=9.09 Hz, 1 H) 11.02 (s, 1 H); ESI-MS m/z [M+H]$^+$ 423.3.

EXAMPLE 82

(S)-1-(4-(2-(cyclopropanecarboxamido)imidazo[1,2-a]pyridin-6-yl)thiophene-2-carbonyl)-4,4-difluoropyrrolidine-2-carboxamide

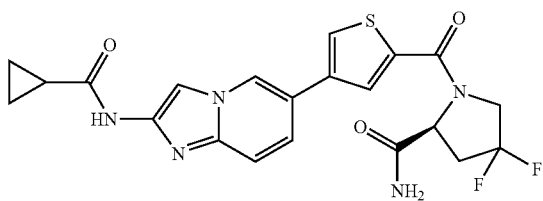 [SMILES: NC(=O)[C@@H]1CC(F)(F)CN1C(=O)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and (S)-4,4-difluoropyrrolidine-2-carboxamide, HCl to give the title compound (16% yield) as an off-white solid. $^1$H NMR (400 MHz, DMSO-$d_6$) δ ppm 0.72-0.97 (m, 4 H) 1.84-2.01 (m, 1 H) 4.11 (br. s., 2 H) 4.39-4.57 (m, 2 H) 4.71 (br. s., 1 H) 6.64 (br. s., 1 H) 7.20 (br. s., 1 H) 7.49 (d, J=9.35 Hz, 1 H) 7.55-7.75 (m, 2 H) 8.00-8.12 (m, 2 H) 8.17 (s, 1 H) 8.35 (s, 1 H) 9.09 (s, 1 H) 11.01 (s, 1 H); ESI-MS m/z [M+H]$^+$ 460.3.

EXAMPLE 83

4-(2-(cyclopropanecarboxamido)imidazo[1,2-a]pyridin-6-yl)-N-(2-methoxyethyl)-N-(2,2,2-trifluoroethyl)thiophene-2-carboxamide

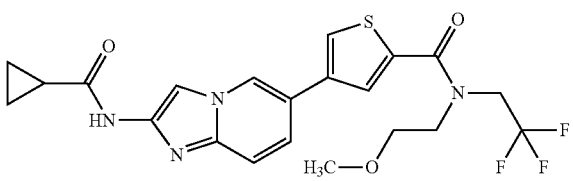 [SMILES: COCCN(CC(F)(F)F)C(=O)c1cc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiophene-2-carboxylic acid and 2,2,2-trifluoro-N-(2-methoxyethyl)ethanamine to give the title compound (9% yield) as a beige solid. $^1$H NMR (400 MHz, DMSO-$d_6$) δ ppm 0.77-0.87 (m, 4 H) 1.91-1.98 (m, 1 H) 3.23 (s, 3 H) 3.56 (t, J=5.31 Hz, 2 H) 3.89 (br. s., 2 H) 4.46 (d, J=8.84 Hz, 1 H) 6.57 (s, 1 H) 7.49 (d, J=9.35 Hz, 1 H) 7.64 (dd, J=9.35, 1.77 Hz, 1 H) 7.97 (s, 1 H) 8.02 (s, 1 H) 8.13 (d, J=1.26 Hz, 1 H) 9.03 (s, 1 H) 11.01 (s, 1 H); ESI-MS m/z [M+H]$^+$ 467.4.

EXAMPLE 84

4-(2-(cyclopropanecarboxamido)imidazo[1,2-a]pyridin-6-yl)-N-(4-hydroxytetrahydrofuran-3-yl)thiophene-2-carboxamide

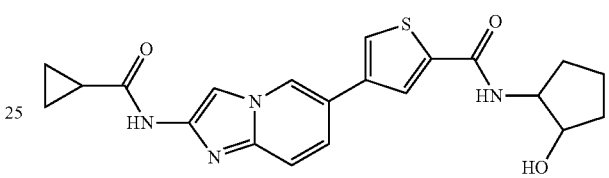

Prepared by the methodology of Example 54 using 4-(2-(cyclopropanecarboxamido)imidazo[1,2-a]pyridin-6-yl)thiophene-2-carboxylic acid and 4-aminotetrahydrofuran-3-ol to give the title compound (37% yield) as an off-white solid. $^1$H NMR (400 MHz, DMSO-$d_6$) δ ppm 0.74-0.90 (m, 4 H) 1.86-2.04 (m, 1 H) 3.49-3.74 (m, 2 H) 3.89-4.05 (m, 2 H) 4.20 (br. s., 2 H) 5.35 (d, J=3.79 Hz, 1 H) 7.46-7.62 (m, 2 H) 7.98-8.12 (m, 2 H) 8.30 (d, J=1.26 Hz, 1 H) 8.58 (d, J=6.82 Hz, 1 H) 8.87 (s, 1 H) 11.02 (s, 1 H); ESI-MS m/z [M+H]$^+$ 413.3.

EXAMPLE 85

4-(2-(cyclopropanecarboxamido)imidazo[1,2-a]pyridin-6-yl)-N-(2-oxocyclopentyl)thiophene-2-carboxamide

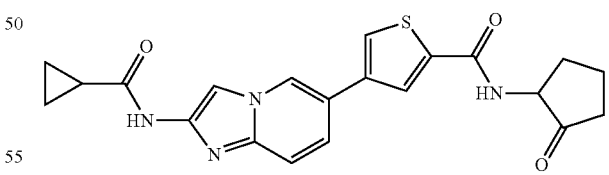

Prepared by the methodology of Example 54 using 4-(2-(cyclopropanecarboxamido)imidazo[1,2-a]pyridin-6-yl)thiophene-2-carboxylic acid and 2-aminocyclopentanone, TFA to give the title compound (8% yield) as an off-white solid. $^1$H NMR (400 MHz, DMSO-$d_6$) δ ppm 0.76-0.87 (m, 4 H) 1.82-2.03 (m, 4 H) 2.16-2.28 (m, 2 H) 4.25 (d, J=10.36 Hz, 1 H) 6.65 (br. s., 1 H) 7.45-7.60 (m, 1 H) 8.05 (s, 1 H) 8.08 (d, J=1.52 Hz, 1 H) 8.17 (d, J=1.52 Hz, 1 H) 8.42 (s, 1 H) 8.76 (d, J=8.08 Hz, 1 H) 8.90 (s, 1 H) 11.02 (s, 1 H); ESI-MS m/z [M+H]$^+$ 409.3.

EXAMPLE 86

4-(2-(cyclopropanecarboxamido)imidazo[1,2-a]pyridin-6-yl)-N-(2,2-difluoroethyl)thiazole-2-carboxamide

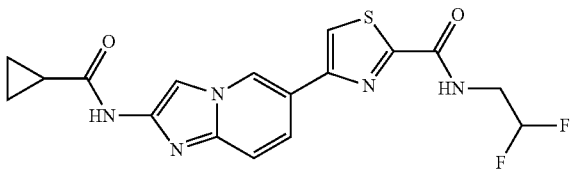 [SMILES: O=C(NCC(F)F)c1nc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiazole-2-carboxylic acid and 2,2-difluoroethanamine to give the title compound (25% yield) as an off-white solid. $^1$H NMR (400 MHz, DMSO-$d_6$) δ ppm 0.75-0.90 (m, 4 H) 1.91-2.01 (m, 1 H) 3.69-3.82 (m, 2 H) 5.99-6.38 (m, 1 H) 7.56 (d, J=9.35 Hz, 1 H) 7.89 (dd, J=9.35, 1.77 Hz, 1 H) 8.07 (s, 1 H) 8.41 (s, 1 H) 9.18-9.28 (m, 2 H) 11.06 (s, 1 H); ESI-MS m/z [M+H]$^+$ 392.3.

EXAMPLE 87

(S)-4-(2-(cyclopropanecarboxamido)imidazo[1,2-a]pyridin-6-yl)-N-(tetrahydrofuran-3-yl)thiazole-2-carboxamide

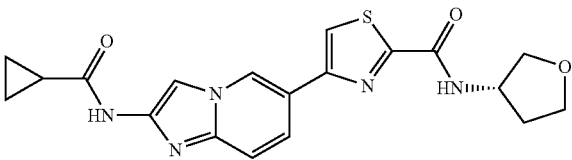 [SMILES: O=C(N[C@H]1CCOC1)c1nc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiazole-2-carboxylic acid and (S)-tetrahydrofuran-3-amine, HCl to give the title compound (36% yield) as an off-white solid. $^1$H NMR (400 MHz, DMSO-$d_6$) δ ppm 0.77-0.87 (m, 4 H) 1.92-1.99 (m, 1 H) 1.99-2.09 (m, 1 H) 2.17-2.27 (m, 1 H) 3.65-3.77 (m, 2 H) 3.85-3.97 (m, 2 H) 4.52 (d, J=7.33 Hz, 1 H) 7.53 (d, J=9.35 Hz, 1 H) 7.90 (dd, J=9.35, 1.77 Hz, 1 H) 8.07 (s, 1 H) 8.37 (s, 1 H) 8.89 (d, J=7.58 Hz, 1 H) 9.24 (s, 1 H) 11.05 (s, 1 H); ESI-MS m/z [M+H]$^+$ 398.3.

EXAMPLE 88

(S)-4-(2-(cyclopropanecarboxamido)imidazo[1,2-a]pyridin-6-yl)-N-(tetrahydro-2H-pyran-3-yl)thiazole-2-carboxamide

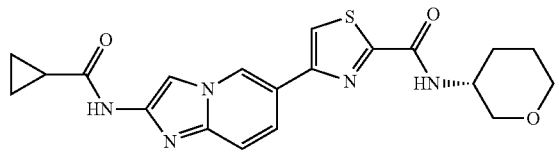 [SMILES: O=C(N[C@@H]1CCCOC1)c1nc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiazole-2-carboxylic acid and (S)-tetrahydro-2H-pyran-3-amine, HCl to give the title compound (22% yield) as an off-white solid. $^1$H NMR (400 MHz, DMSO-$d_6$) δ ppm 0.77-0.91 (m, 4 H) 1.55-1.81 (m, 2 H) 1.91-2.00 (m, 2 H) 3.80 (t, J=14.15 Hz, 2 H) 3.95 (br. s., 1 H) 4.10 (q, J=5.14 Hz, 3 H) 7.54 (d, J=9.35 Hz, 1 H) 7.89 (dd, J=9.35, 1.77 Hz, 1 H) 8.08 (s, 1 H) 8.37 (s, 1 H) 8.59 (d, J=8.34 Hz, 1 H) 9.23 (s, 1 H) 11.05 (s, 1 H); ESI-MS m/z [M+H]$^+$ 412.4.

EXAMPLE 89

4-(2-(cyclopropanecarboxamido)imidazo[1,2-a]pyridin-6-yl)-N-((1S, 2R)-2-hydroxycyclopentyl)thiazole-2-carboxamide

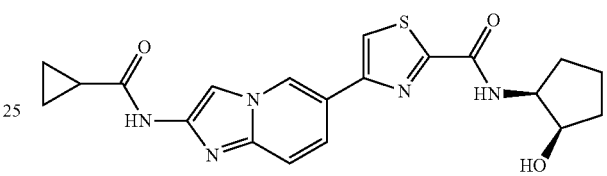

Prepared by the methodology of Example 54 4-(2-(cyclopropanecarboxamido)imidazo[1,2-a]pyridin-6-yl)thiazole-2-carboxylic acid and (1R,2S)-2-aminocyclopentanol, HCl to give the title compound (18% yield) as an off-white solid. $^1$H NMR (400 MHz, DMSO-$d_6$) δ ppm 0.78-0.87 (m, 4 H) 1.46-1.92 (m, 3 H) 1.96 (d, J=7.58 Hz, 2 H) 3.99-4.13 (m, 3 H) 5.14 (d, J=4.04 Hz, 1 H) 6.55 (s, 1 H) 7.54 (d, J=9.09 Hz, 1 H) 7.85 (dd, J=9.35, 1.77 Hz, 1 H) 8.06-8.14 (m, 2 H) 8.38 (s, 1 H) 9.21-9.28 (m, 1 H) 11.04 (s, 1 H); ESI-MS m/z [M+H]$^+$ 412.4.

EXAMPLE 90

4-(2-(cyclopropanecarboxamido)imidazo[1,2-a]pyridin-6-yl)-N-(2,2-difluorocyclopentyl)thiazole-2-carboxamide

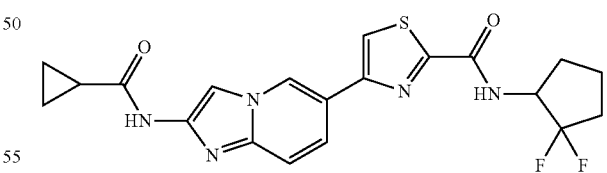

Prepared by the methodology of Example 54 4-(2-(cyclopropanecarboxamido)imidazo[1,2-a]pyridin-6-yl)thiazole-2-carboxylic acid and 2,2-difluorocyclopentanamine to give the title compound (6% yield) as a tan solid. $^1$H NMR (400 MHz, DMSO-$d_6$) δ ppm 0.80-0.89 (m, 4 H) 1.16-1.32 (m, 2 H) 1.68-1.87 (m, 1 H) 1.94-2.02 (m, 1 H) 2.11-2.22 (m, 2 H) 4.59-4.67 (m, 1 H) 7.55 (d, J=9.09 Hz, 1 H) 7.92 (dd, J=9.35, 1.77 Hz, 1 H) 8.09 (s, 1 H) 8.21 (s, 1 H) 8.41 (s, 1 H) 8.83 (d, J=8.84 Hz, 1 H) 9.25 (s, 1 H) 11.06 (s, 1 H); ESI-MS m/z [M+H]$^+$ 432.3.

EXAMPLE 91

4-(2-(cyclopropanecarboxamido)imidazo[1,2-a]pyridin-6-yl)-N-(2-oxocyclopentyl)thiazole-2-carboxamide

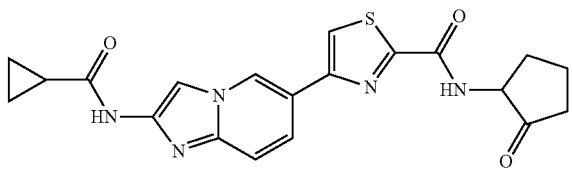 [SMILES: O=C(NC1CCCC1=O)c1nc(-c2ccc3nc(NC(=O)C4CC4)cn3c2)cs1]

Prepared by the methodology of Example 54 using 4-(2-(cyclopropanecarboxamido)imidazo[1,2-a]pyridin-6-yl)thiazole-2-carboxylic acid and 2-aminocyclopentanone, TFA to give the title compound (26% yield) as a beige solid. $^1$H NMR (400 MHz, DMSO-$d_6$) δ ppm 0.77-0.92 (m, 4 H) 1.82-2.12 (m, 3 H) 2.12-2.41 (m, 3 H) 4.24-4.43 (m, 1 H) 7.38-7.57 (m, 1 H) 7.88 (dd, J=9.35, 1.77 Hz, 1 H) 8.01-8.12 (m, 1 H) 8.32-8.43 (m, 2 H) 9.06 (d, J=8.34 Hz, 1 H) 9.18 (dd, J=1.64, 0.88 Hz, 1 H) 11.05 (s, 1 H); ESI-MS m/z [M+H]$^+$ 410.3.

EXAMPLE 92

4-(2-(cyclopropanecarboxamido)imidazo[1,2-a]pyridin-6-yl)-N-(3,3,3-trifluoropropyl)thiazole-2-carboxamide

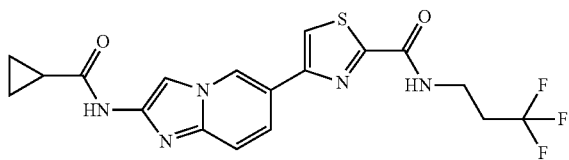

Prepared by the methodology of Example 54 using 4-(2-(cyclopropanecarboxamido)imidazo[1,2-a]pyridin-6-yl)thiazole-2-carboxylic acid and 3,3,3-trifluoropropan-1-amine, HCl to give the title compound (19% yield) as a beige solid. $^1$H NMR (400 MHz, DMSO-$d_6$) δ ppm 0.75-0.90 (m, 4 H) 1.95 (br. s., 1 H) 2.59-2.72 (m, 2 H) 3.54-3.67 (m, 2 H) 7.55 (d, J=9.35 Hz, 1 H) 7.84-7.93 (m, 1 H) 8.06 (s, 1 H) 8.37 (s, 1 H) 9.09 (t, J=5.68 Hz, 1 H) 9.18 (s, 1 H) 11.05 (s, 1 H); ESI-MS m/z [M+H]$^+$ 424.3.

EXAMPLE 93

(R)-N-(6-(2-(2-(trifluoromethyl)pyrrolidine-1-carbonyl)thiazol-4-yl)imidazo[1,2-a]pyridin-2-yl)cyclopropanecarboxamide

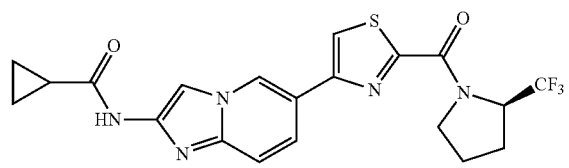 [SMILES: O=C(Nc1cn2cc(-c3csc(C(=O)N4CCC[C@@H]4C(F)(F)F)n3)ccc2n1)C1CC1]

Prepared by the methodology of Example 54 using 4-(2-(cyclopropanecarboxamido)imidazo[1,2-a]pyridin-6-yl)thiazole-2-carboxylic acid and (R)-2-(trifluoromethyl)pyrrolidine to give the title compound (18% yield) as a beige solid. $^1$H NMR (400 MHz, DMSO-$d_6$) δ ppm 0.78-0.90 (m, 4 H) 1.90-2.01 (m, 1 H) 2.01-2.17 (m, 3 H) 4.23 (dt, J=11.12, 6.95 Hz, 1 H) 4.31-4.49 (m, 1 H) 5.11 (t, J=7.71 Hz, 1 H) 7.57 (d, J=9.60 Hz, 1 H) 7.72-7.93 (m, 1 H) 8.06-8.25 (m, 1 H) 8.36-8.52 (m, 1 H) 9.17-9.41 (m, 1 H) 11.12 (s, 1 H); ESI-MS m/z [M+H]$^+$ 450.4.

EXAMPLE 94

4-(2-(cyclopropanecarboxamido)imidazo[1,2-a]pyridin-6-yl)-N-(2-oxotetrahydrofuran-3-yl)thiazole-2-carboxamide

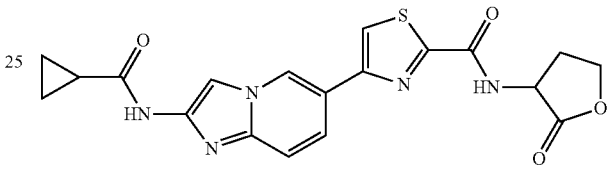

Prepared by the methodology of Example 54 using 4-(2-(cyclopropanecarboxamido)imidazo[1,2-a]pyridin-6-yl)thiazole-2-carboxylic acid and 3-aminodihydrofuran-2(3H)-one, HBr to give the title compound (24% yield) as an off-white solid. $^1$H NMR (400 MHz, DMSO-$d_6$) δ ppm 0.72-0.87 (m, 6 H) 1.92-2.04 (m, 1 H) 4.26-4.38 (m, 1 H) 4.38-4.52 (m, 1 H) 4.85-4.98 (m, 1 H) 7.56 (d, J=9.35 Hz, 1 H) 7.89 (dd, J=9.35, 1.77 Hz, 1 H) 8.06 (s, 1 H) 8.41 (s, 1 H) 9.19 (s, 1 H) 9.43 (d, J=8.59 Hz, 1 H) 11.06 (s, 1 H); ESI-MS m/z [M+H]$^+$ 412.3.

EXAMPLE 95

4-(2-(cyclopropanecarboxamido)imidazo[1,2-a]pyridin-6-yl)-N-(2-hydroxyethyl)thiazole-2-carboxamide

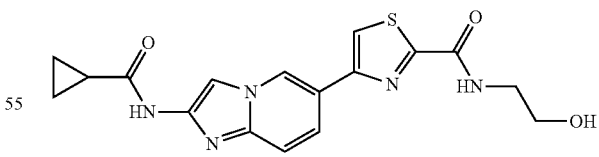

Prepared by the methodology of Example 54 using 4-(2-(cyclopropanecarboxamido)imidazo[1,2-a]pyridin-6-yl)thiazole-2-carboxylic acid and 2-aminoethanol to give the title compound (8% yield) as a tan solid. $^1$H NMR (400 MHz, DMSO-$d_6$) δ ppm 0.77-0.88 (m, 5 H) 1.24 (s, 1 H) 3.54-3.60 (m, 3 H) 6.56 (s, 2 H) 7.48-7.66 (m, 1 H) 7.88 (dd, J=9.35, 1.77 Hz, 1 H) 8.07 (s, 1 H) 8.37-8.44 (m, 1 H) 9.23 (s, 1 H) 11.05 (s, 1 H); ESI-MS m/z [M+H]$^+$ 372.3.

EXAMPLE 96

(S)-N-(6-(2-(4,4-difluoro-2-(hydroxymethyl)pyrrolidine-1-carbonyl)thiazol-4-yl)imidazo[1,2-a]pyridin-2-yl)cyclopropanecarboxamide

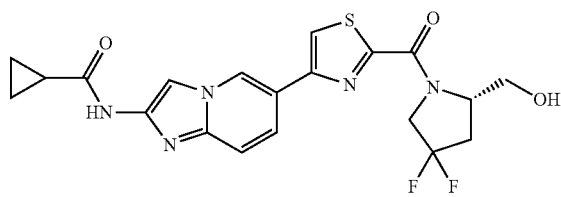 [SMILES: O=C(Nc1cn2cc(-c3csc(C(=O)N4CC(F)(F)C[C@H]4CO)n3)ccc2n1)C1CC1]

Prepared by the methodology of Example 54 using 4-(2-(cyclopropanecarboxamido)imidazo[1,2-a]pyridin-6-yl)thiazole-2-carboxylic acid and (S)-(4,4-difluoropyrrolidin-2-yl)methanol (25.06 mg, 0.183 mmol) to give the title compound (24% yield) as a beige solid. $^1$H NMR (400 MHz, DMSO-$d_6$) δ ppm 0.77-0.85 (m, 4 H) 1.94 (d, J=6.82 Hz, 1 H) 3.65 (d, J=18.44 Hz, 2 H) 4.10 (br. s., 1 H) 4.51 (br. s., 1 H) 4.86 (d, J=9.35 Hz, 1 H) 5.11 (br. s., 1 H) 6.71 (br. s., 2 H) 7.45-7.56 (m, 1 H) 7.82 (dd, J=9.35, 1.77 Hz, 1 H) 8.10-8.23 (m, 1 H) 8.39-8.46 (m, 1 H) 9.14-9.28 (m, 1 H) 10.98-11.05 (m, 1 H); ESI-MS m/z [M+H]$^+$ 448.4.

EXAMPLE 97

N-(6-(2-(3-methoxypyrrolidine-1-carbonyl)thiazol-4-yl)imidazo[1,2-a]pyridin-2-yl)cyclopropanecarboxamide

Prepared by the methodology of Example 54 using 4-(2-(cyclopropanecarboxamido)imidazo[1,2-a]pyridin-6-yl)thiazole-2-carboxylic acid 3-methoxypyrrolidine, HCl give the title compound, as its TFA salt, (42% yield) as an off-white solid. $^1$H NMR (400 MHz, DMSO-$d_6$) δ ppm 0.79-0.88 (m, 4 H) 1.91-2.00 (m, 1 H) 2.06 (d, J=8.08 Hz, 1 H) 2.17 (br. s., 1 H) 3.29 (s, 3 H) 3.47-3.56 (m, 1 H) 3.56-3.62 (m, 1 H) 4.14 (d, J=10.11 Hz, 2 H) 4.31-4.41 (m, 1 H) 7.56 (dd, J=9.09, 2.78 Hz, 1 H) 7.86 (d, J=9.35 Hz, 1 H) 8.19 (s, 1 H) 8.38 (s, 1 H) 9.23 (d, J=3.54 Hz, 1 H) 11.07 (s, 1 H); ESI-MS m/z [M+H]$^+$ 412.4.

EXAMPLE 98

1-(4-(2-(cyclopropanecarboxamido)imidazo[1,2-a]pyridin-6-yl)thiazole-2-carbonyl)pyrrolidine-3-carboxamide

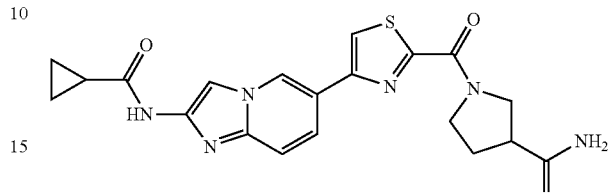

Prepared by the methodology of Example 54 using 4-(2-(cyclopropanecarboxamido)imidazo[1,2-a]pyridin-6-yl)thiazole-2-carboxylic acid and pyrrolidine-3-carboxamide, HCl to give the title compound (26% yield) as a beige solid. $^1$H NMR (400 MHz, DMSO-$d_6$) δ ppm 0.76-0.87 (m, 4 H) 1.91-2.02 (m, 1 H) 2.10-2.24 (m, 1 H) 2.94-3.03 (m, 1 H) 3.58-3.70 (m, 1 H) 3.71-3.82 (m, 1 H) 4.08-4.23 (m, 1 H) 4.30-4.43 (m, 1 H) 6.64 (br. s., 1 H) 7.02 (br. s., 1 H) 7.51-7.61 (m, 2 H) 7.81 (dt, J=9.35, 2.02 Hz, 1 H) 8.11-8.19 (m, 1 H) 8.31-8.39 (m, 1 H) 9.18 (d, J=12.13 Hz, 1 H) 11.01 (d, J=4.55 Hz, 1 H); ESI-MS m/z [M+H]$^+$ 425.4.

EXAMPLE 99

4-(2-(cyclopropanecarboxamido)imidazo[1,2-a]pyridin-6-yl)-N-(5-oxopyrrolidin-3-yl)thiazole-2-carboxamide

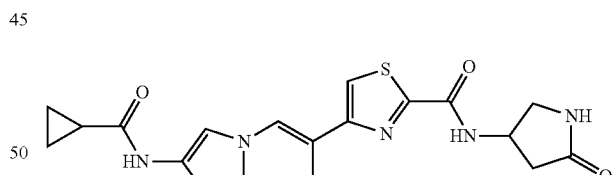

Prepared by the methodology of Example 54 using 4-(2-(cyclopropanecarboxamido)imidazo[1,2-a]pyridin-6-yl)thiazole-2-carboxylic acid and 4-aminopyrrolidin-2-one, HCl to give the title compound (24% yield) as an off-white solid. $^1$H NMR (400 MHz, DMSO-$d_6$) δ ppm 0.78-0.86 (m, 4 H) 1.91-2.01 (m, 1 H) 3.58-3.65 (m, 1 H) 4.10 (q, J=5.31 Hz, 2 H) 4.68 (d, J=7.58 Hz, 1 H) 6.55 (s, 2 H) 7.18 (br. s., 1 H) 7.54 (d, J=9.60 Hz, 1 H) 7.73 (s, 1 H) 7.90 (dd, J=9.35, 1.77 Hz, 1 H) 8.38 (s, 1 H) 9.14-9.23 (m, 2 H) 11.05 (s, 1 H); ESI-MS m/z [M+H]$^+$ 411.3.

EXAMPLE 100

N-(6-(2-(3-(hydroxymethyl)pyrrolidine-1-carbonyl)thiazol-4-yl)imidazo[1,2-a]pyridin-2-yl)cyclopropanecarboxamide

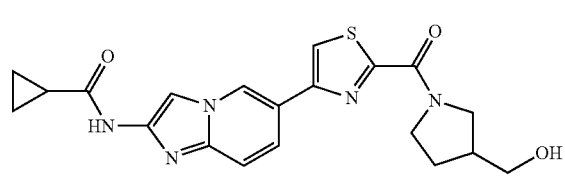 [SMILES: O=C(Nc1cn2cc(-c3csc(C(=O)N4CCC(CO)C4)n3)ccc2n1)C1CC1]

Prepared by the methodology of Example 54 using 4-(2-(cyclopropanecarboxamido)imidazo[1,2-a]pyridin-6-yl)thiazole-2-carboxylic acid and pyrrolidin-3-ylmethanol to give the title compound (5% yield) as a white solid. $^1$H NMR (400 MHz, METHANOL-$d_4$) δ ppm 3.57-3.75 (m, 5 H) 3.75-3.91 (m, 2 H) 4.05 (dd, J=12.00, 7.45 Hz, 1 H) 4.18-4.30 (m, 1 H) 4.43-4.53 (m, 2 H) 7.51 (d, J=9.35 Hz, 2 H) 7.87 (d, J=7.33 Hz, 2 H) 8.13 (d, J=1.26 Hz, 4 H) 8.55 (br. s., 1 H) 9.07 (d, J=8.84 Hz, 1 H); ESI-MS m/z [M+H]$^+$ 412.4.

EXAMPLE 101

N-(6-(2-(3-methoxyazetidine-1-carbonyl)thiazol-4-yl)imidazo[1,2-a]pyridin-2-yl)cyclopropanecarboxamide

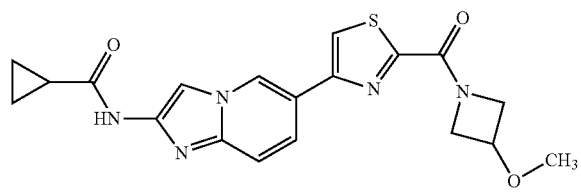 [SMILES: COC1CN(C(=O)c2nc(-c3ccc4nc(NC(=O)C5CC5)cn4c3)cs2)C1]

Prepared by the methodology of Example 54 using 4-(2-(cyclopropanecarboxamido)imidazo[1,2-a]pyridin-6-yl)thiazole-2-carboxylic acid and 3-methoxyazetidine, HCl to give the title compound (5% yield) as an off-white solid. $^1$H NMR (400 MHz, DMSO-$d_6$) δ ppm 0.74-0.88 (m, 4 H) 1.95 (s, 1 H) 3.30 (s, 3 H) 3.93 (d, J=9.35 Hz, 1 H) 4.26-4.39 (m, 2 H) 4.53-4.63 (m, 1 H) 4.96-5.09 (m, 1 H) 7.51 (d, J=9.09 Hz, 1 H) 7.81 (dd, J=9.35, 1.77 Hz, 1 H) 8.20 (s, 1 H) 8.37 (s, 1 H) 9.20 (s, 1 H) 11.01 (s, 1 H); ESI-MS m/z [M+H]$^+$ 398.4.

EXAMPLE 102

N-(6-(2-(3-cyanoazetidine-1-carbonyl)thiazol-4-yl)imidazo[1,2-a]pyridin-2-yl)cyclopropanecarboxamide

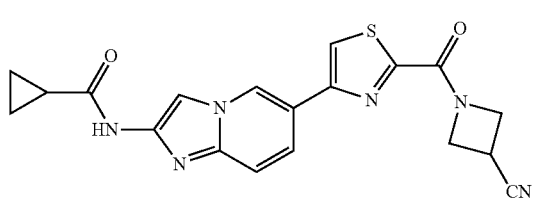 [SMILES: N#CC1CN(C(=O)c2nc(-c3ccc4nc(NC(=O)C5CC5)cn4c3)cs2)C1]

Prepared by the methodology of Example 54 using 4-(2-(cyclopropanecarboxamido)imidazo[1,2-a]pyridin-6-yl)thiazole-2-carboxylic acid and azetidine-3-carbonitrile, HCl to give the title compound (5% yield) as an off-white solid. $^1$H NMR (400 MHz, DMSO-$d_6$) δ ppm 0.78-0.91 (m, 4 H) 1.95 (s, 1 H) 3.90-4.06 (m, 1 H) 4.10 (q, J=5.22 Hz, 3 H) 4.29-4.51 (m, 2 H) 4.98-5.13 (m, 2 H) 7.52 (d, J=9.09 Hz, 1 H) 7.82 (dd, J=9.35, 1.77 Hz, 1 H) 8.19 (s, 1 H) 8.41 (s, 1 H) 9.21 (s, 1 H) 11.01 (s, 1 H); ESI-MS m/z [M+H]$^+$ 393.3.

EXAMPLE 103

N-(6-(2-(3-methylpyrrolidine-1-carbonyl)thiazol-4-yl)imidazo[1,2-a]pyridin-2-yl)cyclopropanecarboxamide

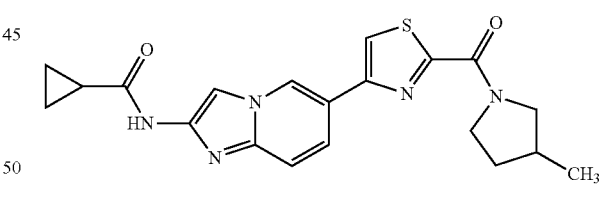

Prepared by the methodology of Example 54 using 4-(2-(cyclopropanecarboxamido)imidazo[1,2-a]pyridin-6-yl)thiazole-2-carboxylic acid and 3-methylpyrrolidine, HCl to give the title compound (22% yield) as a tan solid. $^1$H NMR (400 MHz, DMSO-$d_6$) δ ppm 0.76-0.87 (m, 4 H) 1.05-1.13 (m, 3 H) 1.49-1.58 (m, 1 H) 1.61-1.70 (m, 1 H) 1.91-2.08 (m, 1 H) 3.07-3.13 (m, 1 H) 3.50-3.67 (m, 1 H) 3.67-3.83 (m, 1 H) 4.07-4.19 (m, 1 H) 4.14-4.52 (m, 1 H) 7.45-7.61 (m, 1 H) 7.75-7.88 (m, 1 H) 8.14-8.24 (m, 1 H) 8.28-8.44 (m, 1 H) 9.09-9.26 (m, 1 H) 10.97-11.07 (m, 1 H); ESI-MS m/z [M+H]$^+$ 396.4.

EXAMPLE 104

(R)-3-(2-(cyclopropanecarboxamido)imidazo[1,2-a]pyridin-6-yl)-N-(1,1,1-trifluoropropan-2-yl)-1H-pyrazole-5-carboxamide

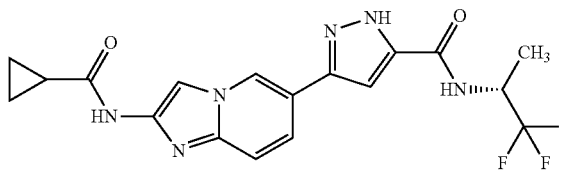

Prepared by the methodology of Example 54 using 3-(2-(cyclopropanecarboxamido)imidazo[1,2-a]pyridin-6-yl)-1H-pyrazole-5-carboxylic acid and (R)-1,1,1-trifluoropropan-2-amine, HCl to give the title compound (12% yield) as a beige solid. $^1$H NMR (400 MHz, DMSO-$d_6$) δ ppm 0.73-0.91 (m, 4 H) 1.38 (d, J=6.82 Hz, 3 H) 1.88-2.07 (m, 1 H) 4.81-4.89 (m, 1 H) 5.40 (br. s., 1 H) 6.62 (br. s., 1 H) 7.23 (br. s., 1 H) 7.52 (d, J=9.09 Hz, 1 H) 7.61-7.71 (m, 1 H) 8.07 (s, 1 H) 8.99 (s, 1 H) 11.02 (s, 1 H); ESI-MS m/z [M+H]$^+$ 407.4.

EXAMPLE 105

N-(6-(5-(4-fluoropiperidine-1-carbonyl)-1H-pyrazol-3-yl)imidazo[1,2-a]pyridin-2-yl)cyclopropanecarboxamide

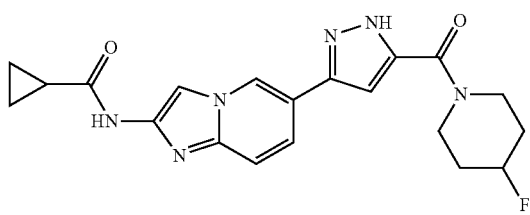 [SMILES: O=C(Nc1cn2cc(-c3cc(C(=O)N4CCC(F)CC4)[nH]n3)ccc2n1)C1CC1]

Prepared by the methodology of Example 54 using 3-(2-(cyclopropanecarboxamido)imidazo[1,2-a]pyridin-6-yl)-1H-pyrazole-5-carboxylic acid and 4-fluoropiperidine, HCl to give the title compound (19% yield) as an off-white solid. $^1$H NMR (400 MHz, DMSO-d6) δ ppm 0.72-0.92 (m, 4 H) 1.75 (br. s., 2 H) 1.84-2.06 (m, 3 H) 3.70 (br. s., 2 H) 4.87-5.05 (m, 1 H) 6.68 (br. s., 1 H) 7.01 (br. s., 1 H) 7.51 (br. s., 1 H) 7.57-7.77 (m, 1 H) 8.02-8.09 (m, 1 H) 8.44 (s, 1 H) 9.01 (s, 1 H) 11.01 (s, 1 H) 13.65 (br. s., 1 H); ESI-MS m/z [M+H]$^+$ 397.4.

EXAMPLE 106

3-(2-(cyclopropanecarboxamido)imidazo[1,2-a]pyridin-6-yl)-N-methyl-N-(2,2,2-trifluoroethyl)-1H-pyrazole-5-carboxamide

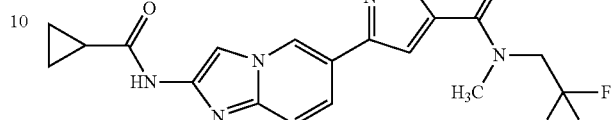

Prepared by the methodology of Example 54 using 3-(2-(cyclopropanecarboxamido)imidazo[1,2-a]pyridin-6-yl)-1H-pyrazole-5-carboxylic acid and 2,2,2-trifluoro-N-methylethanamine, HCl to give the title compound (11% yield) as an off-white solid. $^1$H NMR (400 MHz, DMSO-$d_6$) δ ppm 0.77-0.89 (m, 4 H) 1.95 (s, 1 H) 3.06-3.17 (m, 1 H) 3.41-3.50 (m, 3 H) 4.31-4.45 (m, 1 H) 4.98-5.07 (m, 1 H) 7.47-7.60 (m, 1 H) 7.60-7.72 (m, 1 H) 8.01-8.07 (m, 1 H) 9.00-9.08 (m, 1 H) 11.03 (br. s., 1 H) 13.80-13.88 (m, 1 H); ESI-MS m/z [M+H]$^+$ 407.4.

EXAMPLE 107

N-(6-(5-(3-fluoropyrrolidine-1-carbonyl)-1H-pyrazol-3-yl)imidazo[1,2-a]pyridin-2-yl)cyclopropanecarboxamide

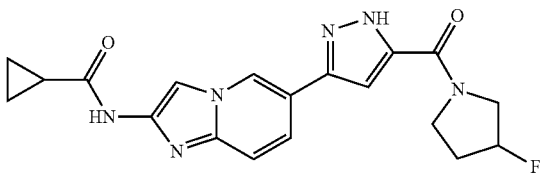 [SMILES: O=C(Nc1cn2cc(-c3cc(C(=O)N4CCC(F)C4)[nH]n3)ccc2n1)C1CC1]

Prepared by the methodology of Example 54 using 3-(2-(cyclopropanecarboxamido)imidazo[1,2-a]pyridin-6-yl)-1H-pyrazole-5-carboxylic acid and 3-fluoropyrrolidine, HCl to give the title compound (4% yield) as a white solid. $^1$H NMR (400 MHz, DMSO-$d_6$) δ ppm 0.76-0.87 (m, 4 H) 1.23 (s, 1 H) 6.67 (s, 3 H) 7.50 (s, 1 H) 8.04 (s, 1 H) 8.50 (s, 1 H) 9.04 (s, 1 H) 11.01 (s, 1 H) 13.74 (s, 1 H); ESI-MS m/z [M+H]$^+$ 383.4.

EXAMPLE 108

4-(2-(cyclopropanecarboxamido)imidazo[1,2-a]pyridin-6-yl)-N-((3S,4S)-4-hydroxytetrahydrofuran-3-yl)thiazole-2-carboxamide

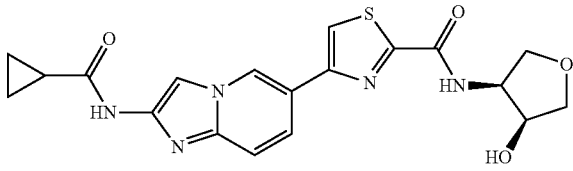 [SMILES: O=C(N[C@H]1COC[C@H]1O)c1nc(-c2ccc3nc(NC(=O)C4CC4)cn3c2)cs1]

Combined 4-(2-(cyclopropanecarboxamido)imidazo[1,2-a]pyridin-6-yl)thiazole-2-carboxylic acid (26.5 mg, 0.081 mmol), 1-(3-dimethylaminopropyl)-3-ethylcarbodiimide hydrochloride (30.9 mg, 0.161 mmol) and HOBT (14.18 mg, 0.105 mmol) in DMF (161 µl) then added (3S,4S)-4-aminotetrahydrofuran-3-ol, HCl (16.90 mg, 0.121 mmol) and N,N-diisopropylethylamine (42.2 µl, 0.242 mmol) at 23° C. The reaction mixture was stirred at 23° C. for 16 hours. The reaction is then placed on heating block set at 40° C. and held for 16 hours. To the reaction was added HATU (46.0 mg, 0.121 mmol), (3S,4S)-4-aminotetrahydrofuran-3-ol (16.65 mg, 0.161 mmol) and triethylamine (45.0 µl, 0.323 mmol) at 23° C. The reaction mixture was stirred at 23° C. for 16 hours. The product was purified by preparative HPLC (Waters XSelect™ 5 um, ID30×75 mm column) using a gradient eluent of 20-35% ACN (with 0.1% ammonium hydroxide) in water (with 0.1% ammonium hydroxide) to give the title compound (9% yield) as an off-white solid. $^1$H NMR (400 MHz, DMSO-$d_6$) δ ppm 0.76-0.89 (m, 4 H) 1.90-2.00 (m, 1 H) 3.62-3.75 (m, 2 H) 3.91-4.04 (m, 2 H) 4.30-4.45 (m, 2 H) 5.67 (d, J=4.80 Hz, 1 H) 7.49-7.63 (m, 1 H) 7.85 (dd, J=9.35, 1.77 Hz, 1 H) 8.01-8.15 (m, 1 H) 8.25-8.35 (m, 1 H) 8.36-8.42 (m, 1 H) 9.23 (s, 1 H) 11.03 (s, 1 H); ESI-MS m/z [M+H]$^+$ 414.3.

EXAMPLE 109

4-(2-(cyclopropanecarboxamido)imidazo[1,2-a]pyridin-6-yl)-N-(4-hydroxytetrahydrofuran-3-yl)thiazole-2-carboxamide

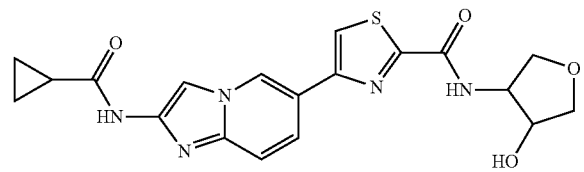 [SMILES: O=C(NC1COCC1O)c1nc(-c2ccc3nc(NC(=O)C4CC4)cn3c2)cs1]

Combined 4-(2-(cyclopropanecarboxamido)imidazo[1,2-a]pyridin-6-yl)thiazole-2-carboxylic acid (100 mg, 0.305 mmol), 1-(3-dimethylaminopropyl)-3-ethylcarbodiimide hydrochloride (117 mg, 0.609 mmol) and HOBT (53.5 mg, 0.396 mmol) in DMF (609 µl) was added 4-aminotetrahydrofuran-3-ol, HCl (87 mg, 0.609 mmol) and N,N-diisopropylethylamine (212 µl, 1.218 mmol) at 23° C. The reaction mixture was stirred at 23° C. for 16 hours. Then HATU (174 mg, 0.457 mmol), 4-aminotetrahydrofuran-3-ol (62.8 mg, 0.609 mmol) and triethylamine (170 µl, 1.218 mmol) were added at 23° C. The reaction mixture was stirred at 23° C. for 16 hours. The product was purified by preparative HPLC (Waters XSelect™ C18, 5 um, ID30×75 mm column) using a gradient eluent of 20-40% ACN (with 0.1% TFA) in water (with 0.1% TFA) to give the title compound (27% yield) as an off-white solid. $^1$H NMR (400 MHz, DMSO-$d_6$) δ ppm 0.79-0.88 (m, 4 H) 1.96 (s, 1 H) 3.17 (s, 1 H) 3.56 (dd, J=9.47, 2.91 Hz, 1 H) 3.73 (dd, J=9.22, 3.66 Hz, 1 H) 4.01 (ddd, J=18.57, 9.35, 5.68 Hz, 2 H) 4.27 (br. s., 1 H) 4.35 (br. s., 1 H) 7.54 (d, J=9.35 Hz, 1 H) 7.92 (d, J=1.77 Hz, 1 H) 8.08 (s, 1 H) 8.38 (s, 1 H) 8.83 (d, J=7.33 Hz, 1 H) 9.24 (s, 1 H) 11.05 (s, 1 H); ESI-MS m/z [M+H]$^+$ 414.3.

EXAMPLE 110

4-(2-(cyclopropanecarboxamido)imidazo[1,2-a]pyridin-6-yl)-N-(4-hydroxytetrahydrofuran-3-yl)thiazole-2-carboxamide

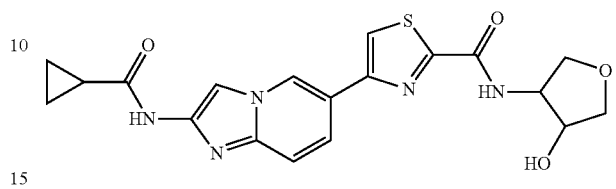

The product of Example 108 was further purified by SFC HPLC (ChiralCel OD-H™, ID 2.1×150 mm column) using an isocratic mobile phase of 16% EtOH in $CO_2$ in (with 0.1% DEA) to give the title compound as a pale beige solid. Retention time: 16.17 min.

EXAMPLE 111

4-(2-(cyclopropanecarboxamido)imidazo[1,2-a]pyridin-6-yl)-N-(4-hydroxytetrahydrofuran-3-yl)thiazole-2-carboxamide

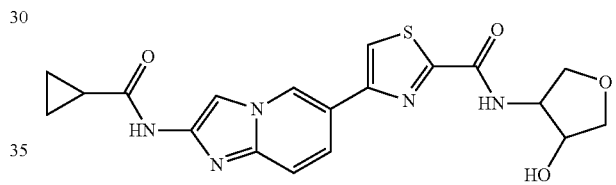

The product of Example 108 was further purified by SFC HPLC (ChiralCel OD-H™, ID 2.1×150 mm column) using an isocratic mobile phase of 16% EtOH in $CO_2$ in (with 0.1% DEA) to give the title compound as a pale beige solid (8 mg). Retention time: 19.71 min.

EXAMPLE 112

N-(6-(2-(3-hydroxypyrrolidine-1-carbonyl)thiazol-4-yl)imidazo[1,2-a]pyridin-2-yl)cyclopropanecarboxamide

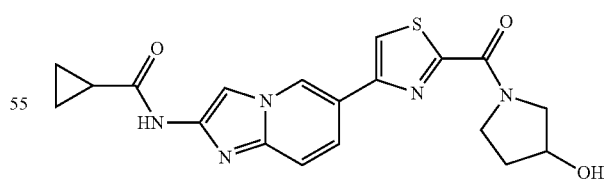

Prepared by the methodology of Example 108 using pyrrolidin-3-ol to give the title compound (39% yield) as an off-white solid. $^1$H NMR (400 MHz, DMSO-$d_6$) δ ppm 0.78-0.90 (m, 4 H) 1.82-2.08 (m, 3 H) 3.50-3.73 (m, 3 H) 4.08-4.27 (m, 1 H) 4.29-4.48 (m, 1 H) 7.53 (dd, J=9.22, 4.17 Hz, 1 H) 7.74-7.86 (m, 1 H) 8.18 (d, J=8.08 Hz, 1 H) 8.33-8.42 (m, 2 H) 9.21 (d, J=8.34 Hz, 1 H) 11.02 (d, J=3.54 Hz, 1 H); ESI-MS m/z [M+H]$^+$ 398.4.

EXAMPLE 113

N-(6-(2-(3-hydroxyazetidine-1-carbonyl)thiazol-4-yl)imidazo[1,2-a]pyridin-2-yl)cyclopropanecarboxamide

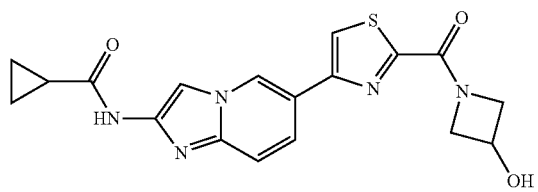

Combined 4-(2-(cyclopropanecarboxamido)imidazo[1,2-a]pyridin-6-yl)thiazole-2-carboxylic acid (30 mg, 0.091 mmol), 1-(3-dimethylaminopropyl)-3-ethylcarbodiimide hydrochloride (35.0 mg, 0.183 mmol) and HOBT (16.05 mg, 0.119 mmol) in DMF (183 µl) then added azetidin-3-ol, HCl (20.02 mg, 0.183 mmol) and N,N-diisopropylethylamine (47.7 µl, 0.274 mmol) at 23° C. The reaction mixture was stirred at 23° C. for 16 hours then additional azetidin-3-ol, HCl (20.02 mg, 0.183 mmol) was added. The reaction mixture was stirred at 23° C. for 16 hours. The product was purified by preparative HPLC (Waters XSelect™ C18, 5 um, ID30×75 mm column) using a gradient eluent of 15-30% ACN (with 0.1% TFA) in water (with 0.1% TFA) to give the title compound (23% yield) as an off-white solid. $^1$H NMR (400 MHz, DMSO-d$_6$) δ ppm 0.76-0.87 (m, 4 H) 1.94-2.07 (m, 1 H) 3.11-3.19 (m, 2 H) 3.86 (dd, J=11.62, 3.54 Hz, 1 H) 4.33-4.43 (m, 1 H) 4.43-4.56 (m, 1 H) 4.98-5.10 (m, 1 H) 7.51 (d, J=9.35 Hz, 1 H) 7.80 (dd, J=9.35, 1.77 Hz, 1 H) 8.19 (s, 1 H) 8.36-8.43 (m, 1 H) 9.20 (s, 1 H) 11.00 (s, 1 H); ESI-MS m/z [M+H]$^+$ 384.3.

EXAMPLE 114

N-(6-(2-(2-(hydroxymethyl)pyrrolidine-1-carbonyl)thiazol-4-yl)imidazo[1,2-a]pyridin-2-yl)cyclopropanecarboxamide

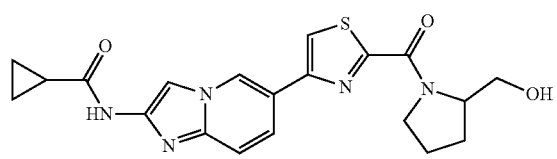 [SMILES: O=C(Nc1cn2cc(-c3csc(C(=O)N4CCCC4CO)n3)ccc2n1)C1CC1]

Prepared by the methodology of Example 113 using pyrrolidin-2-ylmethanol to give the title compound (5% yield) as a white solid. $^1$H NMR (400 MHz, DMSO-d$_6$) δ ppm 0.75-0.90 (m, 4 H) 1.82-2.16 (m, 4 H) 3.17 (s, 1 H) 3.42-3.64 (m, 3 H) 4.09-4.35 (m, 2 H) 4.77-5.23 (m, 2 H) 7.52 (d, J=8.84 Hz, 1 H) 7.74-7.88 (m, 1 H) 8.18 (s, 1 H) 8.36 (d, J=3.54 Hz, 1 H) 9.15-9.27 (m, 1 H) 11.02 (d, J=7.83 Hz, 1 H); ESI-MS m/z [M+H]$^+$ 412.4.

EXAMPLE 115

4-(2-(cyclopropanecarboxamido)imidazo[1,2-a]pyridin-6-yl)-N-(3,3,3-trifluoro-2-hydroxypropyl)thiazole-2-carboxamide Prepared by the methodology of Example 113 using 3-amino-1,1,1-trifluoropropan-2-ol to give the title compound (30% yield) as an off-white solid. $^1$H NMR (400 MHz, DMSO-d$_6$) δ ppm 0.77-0.88 (m, 4 H) 1.95 (s, 1 H) 4.30 (br. s., 1 H) 6.66 (br. s., 3 H) 7.56 (d, J=9.35 Hz, 1 H) 7.89 (dd, J=9.35, 1.77 Hz, 1 H) 8.07 (s, 1 H) 8.41 (br. s., 1 H) 9.00-9.07 (m, 1 H) 9.22 (s, 1 H) 11.06 (s, 1 H); ESI-MS m/z [M+H]$^+$ 440.4.

EXAMPLE 116

5-(2-(cyclopropanecarboxamido)imidazo[1,2-a]pyridin-6-yl)-N-(2,2-difluoroethyl)-1H-pyrazole-3-carboxamide Prepared by the methodology of Example 113 using 3-(2-(cyclopropanecarboxamido)imidazo[1,2-a]pyridin-6-yl)-1H-pyrazole-5-carboxylic acid and pyrrolidine to give the title compound (4% yield) as a beige solid. $^1$H NMR (400 MHz, DMSO-d$_6$) δ ppm 0.68-0.95 (m, 4 H) 1.71-2.02 (m, 5 H) 3.80 (br. s., 1 H) 6.76 (br. s., 1 H) 7.17 (br. s., 1 H) 7.49 (d, J=8.59 Hz, 1 H) 7.69 (br. s., 1 H) 8.04 (s, 1 H) 8.46 (s, 1 H) 9.04 (s, 1 H) 11.01 (s, 1 H) 13.66 (s, 1 H); ESI-MS m/z [M+H]$^+$ 365.4.

EXAMPLE 117

4-(2-(cyclopropanecarboxamido)imidazo[1,2-a]pyridin-6-yl)-N-(1,1,1-trifluoro-3-methylbutan-2-yl)thiophene-2-carboxamide Combined 4-(2-(cyclopropanecarboxamido)imidazo[1,2-a]pyridin-6-yl)thiophene-2-carboxylic acid (35 mg, 0.107 mmol) and HATU (61.0 mg, 0.160 mmol) in DMF (214 μl) then added 1,1,1-trifluoro-3-methylbutan-2-amine (45.3 mg, 0.321 mmol) and triethylamine (59.6 μl, 0.428 mmol) at 23° C. The reaction mixture was stirred at 23° C. for 16 hours. Then was purified by preparative HPLC (Phenomenex Gemini™ C18, 5 μm, ID30×75 mm column) using a gradient eluent of 30-50% ACN in water (TFA) to give the title compound, as its TFA salt, (49% yield) as a white solid. $^1$H NMR (400 MHz, DMSO-$d_6$) δ ppm 0.79-0.87 (m, 4 H) 1.00-1.07 (m, 6 H) 1.91-1.98 (m, 1 H) 2.16-2.24 (m, 1 H) 4.53-4.62 (m, 1 H) 7.52-7.59 (m, 1 H) 7.59-7.68 (m, 1 H) 8.07 (s, 1 H) 8.16 (d, J=1.26 Hz, 1 H) 8.44 (d, J=1.52 Hz, 1 H) 8.80 (d, J=9.60 Hz, 1 H) 8.94 (s, 1 H) 11.07 (s, 1 H); ESI-MS m/z [M+H]$^+$ 451.3.

EXAMPLE 118

4-(2-(cyclopropanecarboxamido)imidazo[1,2-a]pyridin-6-yl)-N-(1-(trifluoromethyl)cyclopropyl)thiophene-2-carboxamide

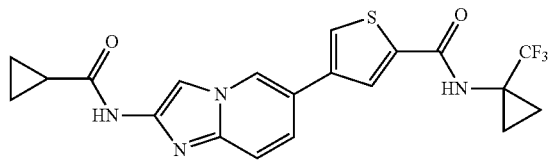 [SMILES: O=C(NC1(C(F)(F)F)CC1)c1cc(-c2ccc3nc(NC(=O)C4CC4)cn3c2)cs1]

Prepared by the methodology of Example 117 using 1-(trifluoromethyl)cyclopropanamine to give title compound, (52% yield) as its TFA salt, as a white solid. $^1$H NMR (400 MHz, DMSO-$d_6$) δ ppm 0.79-0.86 (m, 4 H) 1.18 (br. s., 2 H) 1.33-1.40 (m, 2 H) 1.89-1.99 (m, 1 H) 7.56-7.68 (m, 2 H) 8.06 (s, 1 H) 8.14 (d, J=1.26 Hz, 1 H) 8.28 (d, J=1.52 Hz, 1 H) 8.93 (s, 1 H) 9.29 (s, 1 H) 11.14 (s, 1 H); ESI-MS m/z [M+H]$^+$ 435.3.

EXAMPLE 119

4-(2-(cyclopropanecarboxamido)imidazo[1,2-a]pyridin-6-yl)-N-(3-hydroxypropyl)-N-(2,2,2-trifluoroethyl)thiophene-2-carboxamide

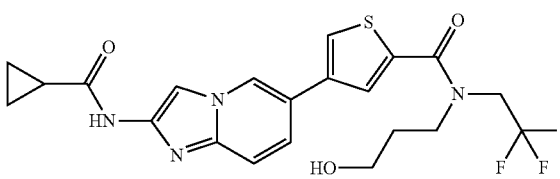

Prepared by the methodology of Example 117 using 3-((2,2,2-trifluoroethyl)amino)propan-1-ol to give the title compound (23% yield) as an off-white solid. $^1$H NMR (400 MHz, DMSO-$d_6$) δ ppm 0.77-0.91 (m, 4 H) 1.84 (br. s., 1 H) 1.88-1.97 (m, 1 H) 3.48 (d, J=4.29 Hz, 2 H) 4.11 (d, J=5.05 Hz, 4 H) 4.39-4.49 (m, 1 H) 6.67 (s, 1 H) 7.48 (d, J=9.35 Hz, 1 H) 7.66 (dd, J=9.22, 1.64 Hz, 1 H) 7.96-8.10 (m, 2 H) 8.15 (s, 1 H) 8.98 (s, 1 H) 11.01 (s, 1 H); ESI-MS m/z [M+H]$^+$ 467.3.

EXAMPLE 120

4-(2-(cyclopropanecarboxamido)imidazo[1,2-a]pyridin-6-yl)-N-(2-hydroxyethyl)-N-(2,2,2-trifluoroethyl)thiophene-2-carboxamide

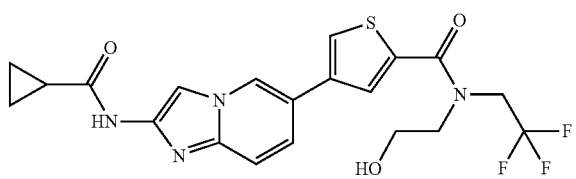 [SMILES: O=C(Nc1cn2cc(-c3csc(C(=O)N(CCO)CC(F)(F)F)c3)ccc2n1)C1CC1]

Prepared by the methodology of Example 117 using 2-((2,2,2-trifluoroethyl)amino)ethanol to give the title compound (28% yield) as an off-white solid. $^1$H NMR (400 MHz, DMSO-$d_6$) δ ppm 0.75-0.88 (m, 4 H) 1.90-2.01 (m, 1 H) 2.98 (t, J=5.68 Hz, 2 H) 3.29-3.32 (m, 2 H) 4.31 (t, J=5.68 Hz, 2 H) 7.49 (d, J=9.35 Hz, 1 H) 7.60-7.73 (m, 1 H) 8.03 (s, 1 H) 8.25-8.33 (m, 2 H) 9.08 (s, 1 H) 11.01 (s, 1 H); ESI-MS m/z [M+H]$^+$ 453.3.

EXAMPLE 121

4-(2-(cyclopropanecarboxamido)imidazo[1,2-a]pyridin-6-yl)-N-(2,2-difluoroethyl)-N-(2-methoxyethyl)thiophene-2-carboxamide

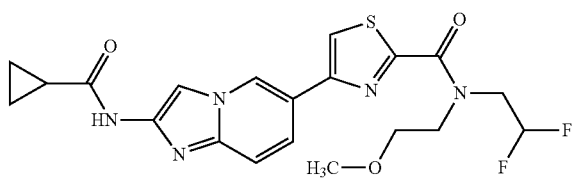

Prepared by the methodology of Example 117 using 2,2-difluoro-N-(2-methoxyethyl)ethanamine, HCl to give the title compound (28% yield) as an off-white solid. $^1$H NMR (400 MHz, DMSO-$d_6$) δ ppm 0.71-0.90 (m, 4 H) 1.89-2.02 (m, 1 H) 3.17 (s, 1 H) 3.27 (s, 3 H) 3.58 (t, J=5.43 Hz, 2 H) 3.83 (br. s., 1 H) 6.12-6.62 (m, 1 H) 7.49 (d, J=9.09 Hz, 1 H) 7.62 (dd, J=9.35, 1.77 Hz, 1 H) 7.91 (br. s., 1 H) 8.03 (s, 1 H) 8.10 (d, J=1.26 Hz, 1 H) 9.00 (d, J=0.76 Hz, 1 H) 11.01 (s, 1 H); ESI-MS m/z [M+H]$^+$ 449.3.

EXAMPLE 122

4-(2-(cyclopropanecarboxamido)imidazo[1,2-a]pyridin-6-yl)-N-(oxetan-3-yl)thiazole-2-carboxamide

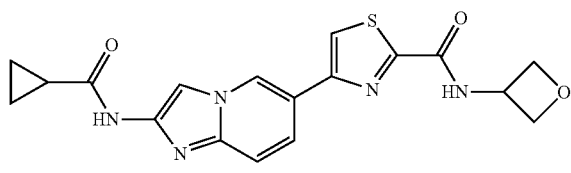 [SMILES: O=C(NC1COC1)c1nc(-c2ccc3nc(NC(=O)C4CC4)cn3c2)cs1]

Prepared by the methodology of Example 117 using 4-(2-(cyclopropanecarboxamido)imidazo[1,2-a]pyridin-6- yl)thiazole-2-carboxylic acid and oxetan-3-amine to give the title compound (20% yield) as an off-white solid. $^1$H NMR (400 MHz, DMSO-$d_6$) δ ppm 0.76-0.88 (m, 4 H) 1.90-2.03 (m, 1 H) 4.69-4.84 (m, 4 H) 5.02-5.13 (m, 1 H) 7.55 (d, J=9.35 Hz, 1 H) 7.92 (dd, J=9.35, 1.77 Hz, 1 H) 8.07 (s, 1 H) 8.34-8.46 (m, 2 H) 9.24 (d, J=0.76 Hz, 1 H) 9.57 (d, J=7.33 Hz, 1 H) 11.06 (s, 1 H); ESI-MS m/z [M+H]$^+$ 384.3.

EXAMPLE 123

N-(6-(5-(2-methylpyrrolidine-1-carbonyl)-1H-pyrazol-3-yl)imidazo[1,2-a]pyridin-2-yl)cyclopropanecarboxamide

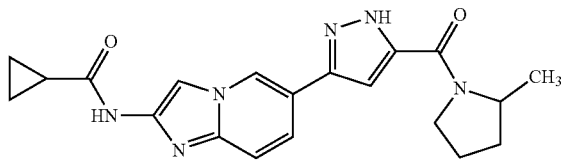 [SMILES: CC1CCCN1C(=O)c1cc(-c2ccc3nc(NC(=O)C4CC4)cn3c2)n[nH]1]

Prepared by the methodology of Example 117 using 3-(2-(cyclopropanecarboxamido)imidazo[1,2-a]pyridin-6-yl)-1H-pyrazole-5-carboxylic acid and 2-methylpyrrolidine to give the title compound (6% yield) as a beige solid. $^1$H NMR (400 MHz, DMSO-$d_6$) δ ppm 0.73-0.86 (m, 4 H) 1.08-1.27 (m, 4 H) 1.84-2.16 (m, 4 H) 6.69 (br. s., 1 H) 7.50 (br. s., 1 H) 7.71 (br. s., 1 H) 8.04 (s, 1 H) 8.41 (br. s., 1 H) 9.03 (s, 2 H) 11.01 (br. s., 1 H) 13.64 (br. s., 1 H); ESI-MS m/z [M+H]$^+$ 379.4

EXAMPLE 124

N-(6-(2-(3-(hydroxymethyl)azetidine-1-carbonyl)thiazol-4-yl)imidazo[1,2-a]pyridin-2-yl)cyclopropanecarboxamide

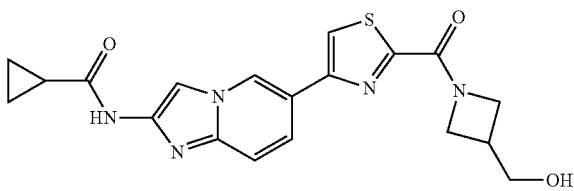 [SMILES: O=C(Nc1cn2cc(-c3csc(C(=O)N4CC(CO)C4)n3)ccc2n1)C1CC1]

Prepared by the methodology of Example 117 using 4-(2-(cyclopropanecarboxamido)imidazo[1,2-a]pyridin-6-yl)thiazole-2-carboxylic acid and 3-(hydroxymethyl)azetidine to give the title compound, as its TFA salt, (21% yield) as a white solid. $^1$H NMR (400 MHz, DMSO-d6) δ ppm 0.75-0.86 (m, 4 H) 1.94 (d, J=5.56 Hz, 1 H) 2.83 (br. s., 1 H) 3.62 (t, J=5.81 Hz, 2 H) 3.87 (dd, J=10.36, 5.05 Hz, 1 H) 4.13 (t, J=9.60 Hz, 1 H) 4.50 (dd, J=10.23, 5.18 Hz, 1 H) 4.80 (t, J=9.47 Hz, 1 H) 4.89 (t, J=5.18 Hz, 1 H) 7.52 (d, J=9.35 Hz, 1 H) 7.77-7.83 (m, 1 H) 8.18 (s, 1 H) 8.35 (s, 1 H) 9.17 (s, 1 H) 11.01 (s, 1 H); ESI-MS m/z [M+H]$^+$ 398.3.

EXAMPLE 125

N-((1R,6R)-6-amino-2,2-difluorocyclohexyl)-4-(2-(cyclopropanecarboxamido)imidazo[1,2-a]pyridin-6-yl)thiophene-2-carboxamide

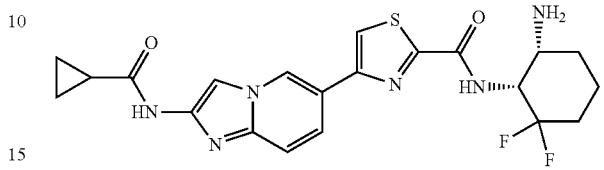

Combined 4-(2-(cyclopropanecarboxamido)imidazo[1,2-a]pyridin-6-yl)thiophene-2-carboxylic acid (50 mg, 0.153 mmol), tert-butyl ((1R,2R)-2-amino-3,3-difluorocyclohexyl)carbamate (45.9 mg, 0.183 mmol) and 2-(3H-[1,2,3]triazolo[4,5-b]pyridin-3-yl)-1,1,3,3-tetramethylisouronium hexafluorophosphate(V) (87 mg, 0.229 mmol) in DMF (1018 μl) and treated with N-ethyl-N-isopropylpropan-2-amine (80 μl, 0.458 mmol). The mixture was stirred at ambient temperature for 5 h and treated with 4N HCl in dioxane (2 mL). The mixture was stirred for 18 h and volatile solvents were removed under a stream of warm nitrogen. The residual DMF solution was diluted with DMSO (0.5 mL) and the reaction mixture was purified by HPLC 15-40% ACN in water (TFA) to give the title compound, as its TFA salt, (53.1% yield) as a white solid. $^1$H NMR (400 MHz, DMSO-$d_6$) δ ppm 0.73-0.95 (m, 4 H) 1.52 (d, J=9.60 Hz, 1 H) 1.77-2.07 (m, 5 H) 2.22-2.47 (m, 1 H) 3.51 (br. s., 1 H) 4.91 (d, J=5.31 Hz, 1 H) 7.55-7.60 (m, 1 H) 7.62-7.69 (m, 1 H) 8.02-8.21 (m, 5 H) 8.27 (d, J=10.11 Hz, 1 H) 8.48 (d, J=1.01 Hz, 1 H) 8.97 (s, 1 H) 11.12 (s, 1 H). MS (ESI) [M+H] 460.

EXAMPLE 126

N-((1R,6S)-6-amino-2,2-difluorocyclohexyl)-4-(2-(cyclopropanecarboxamido)imidazo[1,2-a]pyridin-6-yl)thiophene-2-carboxamide

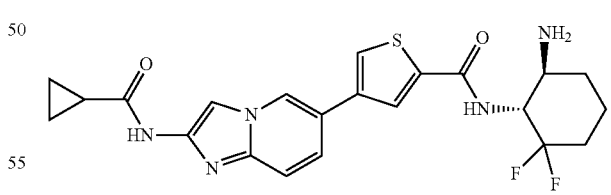

Prepared by the methodology of Example 125 using tert-butyl ((1S,2R)-2-amino-3,3-difluorocyclohexyl)carbamate to give the title compound, as its TFA salt, (20.7% yield) as a white solid. $^1$H NMR (400 MHz, DMSO-$d_6$) δ ppm 0.73-0.90 (m, 4 H) 1.37-1.70 (m, 2 H) 1.78-2.13 (m, 4 H) 2.20 (br. s., 1 H) 3.29 (br. s., 1 H) 4.39-4.61 (m, 1 H) 7.51-7.58 (m, 1 H) 7.58-7.65 (m, 1 H) 8.07 (s, 1 H) 8.15 (d, J=1.01 Hz, 4 H) 8.37 (d, J=1.01 Hz, 1 H) 8.75 (d, J=9.09 Hz, 1 H) 8.94 (s, 1 H) 11.07 (s, 1 H). MS (ESI) [M+H] 460.

EXAMPLE 127

1-(2-(cyclopropanecarboxamido)imidazo[1,2-a]pyrazin-6-yl)-N-(2-hydroxyethyl)-N-(2,2,2-trifluoroethyl)-1H-pyrazole-3-carboxamide

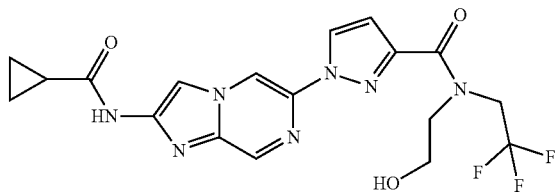 [SMILES: O=C(Nc1cn2cc(-n3ccc(C(=O)N(CCO)CC(F)(F)F)n3)ncc2n1)C1CC1]

Combined cyclopropanecarboxamide (21.0 g, 247 mmol), potassium phosphate (42.0 g, 198 mmol), and dioxane (105 ml), purged with nitrogen, and then heated at 60° C. Via syringe, 2-bromoacetyl bromide (19.89 ml, 229 mmol) was added to the warm mixture and the reaction was allowed to continue stirring at 60° C. After 40 minutes, the reaction mixture was cooled to room temperature followed by further cooling in an ice/brine bath. Water (525 mL) was then slowly added and the reaction mixture was stirred overnight to give a tan solid which was collected by filtration and washed with water until the filtrate was colorless. The resulting off-white solid was dried to give N-(2-bromoacetyl)cyclopropanecarboxamide.

Combined 5-bromopyrazin-2-amine (10.5 g, 60.3 mmol), N-(2-bromoacetyl)cyclopropanecarboxamide (18.65 g, 91 mmol) in DMA (121 ml) and then added disodium phosphate (25.7 g, 181 mmol) and heated the reaction mixture at 80° C. After 44 hours the reaction mixture was cooled to room temperature and crushed ice was added (about 250 mL). Then the reaction mixture was transferred to a 2L Erlenmeyer flask that was ⅔ filled with crushed ice to give a suspension which was stirred and warmed to room temperature. Water was then added to bring the total volume to 1.5L. The dark brown solid was collected by filtration, rinsed with additional water (until fitrate is clear and colorless) and dried under vacuum to give N-(6-bromoimidazo[1,2-a]pyrazin-2-yl)cyclopropanecarboxamide which was used without further purification. ESI-MS: m/z 281.0 (M+H)$^+$.

Combined N-(6-bromoimidazo[1,2-a]pyrazin-2-yl)cyclopropanecarboxamide (12.7 g, 45.2 mmol), ethyl 1H-pyrazole-3-carboxylate (9.50 g, 67.8 mmol), (1S,2S)-N1,N2-dimethylcyclohexane-1,2-diamine (1.285 g, 9.04 mmol), copper (I) iodide (1.721 g, 9.04 mmol) and potassium carbonate (15.61 g, 113 mmol) in DMF (Volume: 156 ml). The reaction mixture was purged with nitrogen, capped, and heated at 130° C. After 48 hours additional (1S,2S)-N1,N2-dimethylcyclohexane-1,2-diamine (1.285 g, 9.04 mmol) and copper (I) iodide (1.721 g, 9.04 mmol) were added. After stirring overnight, the reaction mixture was cooled to room temperature and the DMF was mostly removed via rotovap and then dried under vaccum to give ethyl 1-(2-(cyclopropanecarboxamido)imidazo[1,2-a]pyrazin-6-yl)-1H-pyrazole-3-carboxylate (15.38g) which was used without further purification.

Combined ethyl 1-(2-(cyclopropanecarboxamido)imidazo[1,2-a]pyrazin-6-yl)-1H-pyrazole-3-carboxylate (15.38 g, 45.2 mmol) isopropanol (181 ml), and 1M lithium hydroxide (90 ml, 90 mmol). The reaction mixture was gently warmed and then allowed to stir at room temperature. After 5 hours, additional 1M lithium hydroxide (90 ml, 90 mmol) was added. After 1 hour, the isopropanol was mostly removed by rotovap. Additional water was added to bring the total volume to about 900 mL and the reaction was stirred. After about 1 hour, the reaction mixture was transferred to a 2L Erlenmeyer flask and additional water was added to bring the total volume to about 1.3L. The reaction mixture was then filtered and the filtrate extracted with EtOAc (5×500 mL), the organic layers were discarded and using 6N HCl, the aqueous layer was adjusted to pH=3-4 to give a solid. The solid was collected by filtration, washed with water and dried to give a solid. The solid was pulvarized and further dried undervacuum at 55° C. to give 1-(2-(cyclopropanecarboxamido)imidazo[1,2-a]pyrazin-6-yl)-1H-pyrazole-3-carboxylic (13.482 g) that was used without further purification. ESI-MS: m/z 313.2 (M+H).

Combined pulvarized 1-(2-(cyclopropanecarboxamido)imidazo[1,2-a]pyrazin-6-yl)-1H-pyrazole-3-carboxylic acid (16.5 g, 52.8 mmol) and 2-chloro-1-methylpyridin-1-ium iodide (33.7 g, 132 mmol) in DMF (117 ml). DIEA (32.3 ml, 185 mmol) was added and the mixture was stirred at room temperature. After 8 hours, 2-((2,2,2-trifluoroethyl)amino)ethanol hydrochloride (14.23 g, 79 mmol) was added and the reaction was stirred at 50° C. After stirring overnight, the reaction mixture was cooled to room temperature and filtered through a pad of Celite® into 1.5L saturated aqueous sodium bicarbonate to give a brown solid was collected by vacuum filtration, rinsed with water and dried in a vacuum oven at 55° C. for 4 h, pulvarized, dried further in the vacuum oven at 55° C. The solid was purified by SFC chromatography using an ethyl-pyridine column (2×25 cm) eluing with 15% methanol/CO$_2$, 100 bar at 80 mL/minute. The purified product was dissolved in a mixture of isopropanol/water (4:1) and water was slowly added to give a solid which was collected by filtration, rinsed with water, and dried in a vacuum oven at 50° C. to give the title compound. $^1$H NMR (400 MHz, DMSO-d6) d ppm 0.78-0.91 (m, 4 H) 1.92-2.04 (m, 1 H) 3.58-3.69 (m, 3 H) 4.01 (t, J=5.43 Hz, 1 H) 4.45 (q, J=9.52 Hz, 1 H) 4.82-4.93 (m, 1 H) 5.08 (q, J=8.93 Hz, 1 H) 6.86-6.95 (m, 1 H) 8.48 (s, 1 H) 8.59 (d, J=2.78 Hz, 1 H) 8.89 (s, 1 H) 9.21 (s, 1 H) 11.34 (s, 1 H). ESI-MS: m/z 438.1 (M+H)+.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage, typically on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

In another embodiment, the invention provides methods of treating conditions associated with TBK1, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with TBK1 described herein. The compounds of the present invention are useful as TBK1 inhibitors for a variety of subjects (e.g., humans, non-human mammals and non-mammals).

As used herein terms "condition," "disorder," and "disease" relate to any unhealthy or abnormal state. The term "conditions associated with TBK1" includes conditions, disorders, and diseases in which the inhibition of TBK1 provides a therapeutic benefit, such as immunological disorders, inflammatory disorders, and abnormal cell growth, such as cancer.

The term "conditions associated with TBK1" includes specifically, but is not limited to, autoimmune disorders and conditions include lupus, particularly systemic lupus erythematosus and chilblain lupus, Crohn's disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, the term "conditions associated with TBK1" includes specifically, but is not limited to, inflammatory disorders including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemtic inflammatory response syndrome.

The term "conditions associated with TBK1" includes specifically, includes specific diseases that may fall within one or more general category described above, such as arthritis, including rheumatoid arthritis, and other arthritis diseases, including ankylosing spondylitis, avascular necrosis, Bechet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, among others.

The term "conditions associated with TBK1" includes specifically, fibrotic diseases of the lungs, kidneys, eyes, heart, liver, and skin, including pulmonary fibrosis, idiopathic pulmonary fibrosis, idiopathic interstitial pneumonias, desquamative pulmonary fibrosis, cryptogenic organizing pneumonia, acute interstitial pneumonia, non-specific interstitial pneumonia, respiratory bronchiolitis associated with institial lung disease, cryptogenic organizing pneumonia, lymphocytic interstitial pneumonia, chronic kidney disease, diabetic kidney disease, chronic liver disease, keloidal scarring, and nephrogenic systemic fibrosis.

The term "conditions associated with TBK1" includes specifically, but is not limited to, cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the term "conditions associated with TBK1" includes specifically other diseases related to abnormal cell growth, including non-malignant proliferative diseases such as benign prostatic hypertrophy, restenosis, hyperplasia, synovial proliferation disorder, retinopathy or other neovascular disorders of the eye, among others.

The term "conditions associated with TBK1" includes specifically, but is not limited to, sepsis, septic shock, virally or bacterially induced diseases or infections, mycobateria-induced infections (including opportunistic infections), rejection of transplanted tissues, psoriasis, hemangiomas, diseases with disturbed angiogenesis, especially ischemic or dental diseases, smoker's leg and diabetic ulcers, retinal vasculopathy and cerebral leukodystrophy, systemic sclerosis, glomerulonephritis, dermatomyositis, polymyositis chronic obstructive pulmonary disease, mediating insulin resistance, including as part of the metabolic syndrome, type 2 diabetes mellitus, diabetic dislipidemia, conditions of impaired glucose tolerance, conditions of impaired fasting plasma glucose, metabolic acidosis, ketosis, and appetite regulation, prion diseases, polycystic ovary syndrome, and primary biliary cirrhosis.

In particularly, the term "conditions associated with TBK1" includes primary biliary cirrhosis, ulcerative colitis, and lupus, particularly systemic lupus erythematosus.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for a patient (e.g., an infant) whose mass falls outside of this weight range.

The compounds of the invention may be combined with one or more other pharmacologically active compounds or therapies for the treatment of one or more disorders, diseases or conditions for which TBK1 is indicated may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, a compound of the invention may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, a compound of the invention may be combined with one or more disease modifying antirheumatic drugs (DMARDs), and when treating osteoarthritis, the compounds of formula 1 may be combined with one or more osteoporosis agents.

Particularly useful combinations for treating rheumatoid arthritis include a compound of the invention and methotrexate; a compound of the invention and one or more biological response modifiers, such as lefluonomide, etanercept, adalimumab, and infliximab; or a compound of the invention, methotrexate, and one or more biological response modifiers, such as lefluonomide, etanercept, adalimumab, and infliximab.

The activity of compounds as TBK1 inhibitors may be determined by a variety of methods, including in vitro and in vivo methods.

Example A Inhibition of TBK1 Enzyme

Full length human TBK1 with an N-terminal His-tag was cloned into the pFastBacl vector and was transfected into Sf9 cells. 72 hours later the virus was harvested and amplified through two additional rounds of infections. Then 400 ml of the resulting virus stock was used to infect 10L of Sf9 cells at a density of $2 \times 10^6$ cells/ml. Cell pellets were harvested 48 hours post infection and were lysed by freeze-thaw, homogenization and sonication in binding buffer (25 mM Tris pH7.6, 1 M NaCl, 10 mM imidazole, 0.5 mM TCEP) plus 0.1% Triton X-100 and complete protease inhibitor cocktail. The lysate was spun and the supernatant was purified with a HisTrap FF crude and a Superdex 200 pg column.

TBK1 inhibition is determined using a 384 well plate format in buffer containing 20 mM Hepes, pH 7.4, 10 mM MgCl2, 1 mM EDTA, 0.01% Brij-L23, 1 mM DTT. Each test compound is prepared in DMSO using 2.5-fold serial dilutions for 11 data points, which are added to the buffer so that each dilution contains 1% DMSO. To each well is added 2 µL of 1 µm 5FAM-DRHDSGLDSMKDE-NH$_2$ (in buffer), 2 µL of diluted test compound (1% DMSO in buffer), and 5 µL of 3 nM TBK1 and 25 µM ATP (in buffer). The reaction mixture is incubated at RT for 60 min, and quenched by adding 20 mM Hepes, pH 7.4, 10 mM MgCl$_2$, 1 mM EDTA, 0.01% Brij-L23, 1 mM DTT+25 mM EDTA. To quantify the fluorescent-labeled substrate and product following reaction, the test plate is loaded on a Caliper LC-3000, which measures percent of conversion by microfluidic-based separation. Corresponding $IC_{50}$ values are calculated by non-linear curve fitting of the compound concentrations and percent of inhibition to the standard $IC_{50}$ equation and reported as $pIC_{50}$, i.e., $-\log(IC_{50})$, where $IC_{50}$ is the molar concentration.

Table A provides results for exemplified compounds in Example A.

TABLE A

| TBK1 Inhibition ($pIC_{50}$) for Example (Ex) Compounds | |
|---|---|
| Ex | $pIC_{50}$ |
| 1 | 6.6 |
| 2 | 6.5 |
| 3 | 8.3 |
| 4 | 8.3 |
| 5 | 8.0 |
| 6 | 8.1 |
| 7 | 8.1 |
| 8 | 6.7 |
| 9 | 8.0 |
| 10 | 6.5 |
| 11 | 7.2 |
| 12 | 7.7 |
| 13 | 7.6 |
| 14 | 7.4 |
| 15 | 7.6 |
| 16 | 7.1 |
| 17 | 7.1 |
| 18 | 8.0 |
| 19 | 8.3 |
| 20 | 6.3 |
| 21 | 7.3 |
| 22 | 6.7 |
| 23 | 7.1 |
| 24 | 7.6 |
| 25 | 7.1 |
| 26 | 7.1 |
| 27 | 7.5 |
| 28 | 7.9 |
| 29 | 7.4 |
| 30 | 7.6 |
| 31 | 6.4 |
| 32 | 8.3 |
| 33 | 8.3 |
| 34 | 7.7 |
| 35 | 7.1 |
| 36 | 8.0 |
| 37 | 6.1 |
| 38 | 7.6 |
| 39 | 6.6 |
| 40 | 7.5 |
| 41 | 7.2 |
| 42 | 7.0 |
| 43 | 7.3 |
| 44 | 8.4 |
| 45 | 7.4 |
| 47 | 7.2 |
| 46 | 8.5 |
| 48 | 7.3 |
| 49 | 7.1 |
| 50 | 7.9 |
| 51 | 8.1 |
| 52 | 8.2 |
| 53 | 6.8 |
| 54 | 6.6 |
| 55 | 8.2 |
| 56 | 7.6 |
| 57 | 8.0 |
| 58 | 6.1 |
| 59 | 7.7 |
| 60 | 7.8 |
| 61 | 7.4 |
| 62 | 8.4 |
| 63 | 7.8 |

TABLE A-continued

| TBK1 Inhibition ($pIC_{50}$) for Example (Ex) Compounds | |
|---|---|
| Ex | $pIC_{50}$ |
| 64 | NT |
| 65 | 7.7 |
| 66 | 7.0 |
| 67 | 7.2 |
| 68 | 8.0 |
| 69 | 7.0 |
| 70 | 7.5 |
| 71 | 7.7 |
| 72 | 7.9 |
| 73 | 7.2 |
| 74 | 7.5 |
| 75 | 7.3 |
| 76 | 7.8 |
| 77 | 7.2 |
| 78 | 8.0 |
| 79 | 7.1 |
| 80 | 7.2 |
| 81 | 8.6 |
| 82 | 6.2 |
| 83 | 7.7 |
| 84 | 7.5 |
| 85 | 7.0 |
| 86 | 7.8 |
| 87 | 7.2 |
| 88 | 7.2 |
| 89 | 7.5 |
| 90 | 7.4 |
| 91 | 6.7 |
| 92 | 7.3 |
| 93 | 8.1 |
| 94 | 6.7 |
| 95 | 6.4 |
| 96 | 7.2 |
| 97 | 6.9 |
| 98 | 6.7 |
| 99 | 6.6 |
| 100 | 6.7 |
| 101 | 6.2 |
| 102 | 6.7 |
| 103 | 7.1 |
| 104 | 8.3 |
| 105 | 6.5 |
| 106 | 7.5 |
| 107 | 7.2 |
| 108 | 7.1 |
| 109 | 7.2 |
| 112 | 7.1 |
| 113 | 6.9 |
| 114 | 6.8 |
| 115 | 7.1 |
| 116 | 6.7 |
| 117 | 7.3 |
| 118 | 7.5 |
| 119 | 8.0 |
| 120 | 6.8 |
| 121 | 7.4 |
| 122 | 6.9 |
| 118 | 7.5 |
| 119 | 8.0 |
| 120 | 6.8 |
| 123 | 7.0 |
| 124 | 6.6 |
| 125 | 8.2 |
| 126 | 8.0 |
| 127 | 8.3 |

Example B Inhibition of TBK1 in Cells

TBK1 inhibition is determined using a TLR3 driven RA1-ISRE β-lacatamase reporter assay (Life Technologies). In the assay 50,000 cells/well are plated in black clear bottom 384 well plate. Each test compound is prepared in DMSO using 2.5-fold serial dilutions for 11 data points, which are then added to the media. Cells are stimulated with 0.15 mg/ml poly IC-LMW (Invivogen) for 16 hrs. Reporter activity is detected using the LiveBLAzer-FRET B/G CCF4-AM substrate (Life Technologies) and the plate is read using the Spectramax M5 instrument. Corresponding $EC_{50}$ values are calculated by non-linear curve fitting of the compound concentrations and percent of inhibition to the standard $EC_{50}$ equation and reported as $pEC_{50}$, i.e., $-\log(EC_{50})$, where $EC_{50}$ is the molar concentration.

Table B provides results for exemplified compounds in Example B.

TABLE B

Inhibition of TBK1 in cells
$pEC_{50}$ (EC) for Example (Ex) Compounds

| Ex | EC |
|---|---|
| 1 | 5.08 |
| 2 | 5.08 |
| 3 | 6.78 |
| 4 | 6.21 |
| 5 | 6.10 |
| 6 | 6.45 |
| 7 | 6.41 |
| 8 | 5.04 |
| 9 | 6.64 |
| 10 | <4.3 |
| 11 | 6.09 |
| 12 | 6.02 |
| 13 | 6.09 |
| 14 | 5.76 |
| 15 | 6.03 |
| 16 | 5.98 |
| 17 | 5.53 |
| 18 | 6.60 |
| 19 | 6.39 |
| 20 | NT |
| 21 | 5.47 |
| 22 | NT |
| 23 | 5.27 |
| 24 | 6.33 |
| 25 | 5.48 |
| 26 | 6.12 |
| 27 | 5.43 |
| 28 | 6.17 |
| 29 | 5.17 |
| 30 | 5.19 |
| 31 | NT |
| 32 | 6.92 |
| 33 | 6.57 |
| 34 | 6.29 |
| 35 | 5.28 |
| 36 | 6.61 |
| 37 | NT |
| 38 | 5.93 |
| 39 | <4.3 |
| 40 | 6.15 |
| 41 | NT |
| 42 | 5.29 |
| 43 | 5.63 |
| 44 | 6.67 |
| 45 | 5.90 |
| 46 | 5.18 |
| 47 | 7.06 |
| 48 | 5.70 |
| 49 | 5.50 |
| 50 | 6.32 |
| 51 | 6.31 |
| 52 | 6.83 |
| 53 | 4.60 |
| 54 | 4.70 |
| 55 | 6.56 |
| 56 | 6.20 |
| 57 | 6.66 |
| 58 | NT |
| 59 | 6.62 |
| 60 | 6.63 |

TABLE B-continued

Inhibition of TBK1 in cells
$pEC_{50}$ (EC) for Example (Ex) Compounds

| Ex | EC |
|---|---|
| 61 | 5.58 |
| 62 | 7.13 |
| 63 | 6.43 |
| 64 | NT |
| 65 | 6.17 |
| 66 | 5.69 |
| 67 | 5.93 |
| 68 | 5.99 |
| 69 | 5.54 |
| 70 | 6.05 |
| 71 | 5.62 |
| 72 | 5.92 |
| 73 | 5.78 |
| 74 | 5.87 |
| 75 | 5.77 |
| 76 | 6.04 |
| 77 | 5.78 |
| 78 | 6.32 |
| 79 | 4.64 |
| 80 | 5.86 |
| 81 | 7.35 |
| 82 | NT |
| 83 | 6.19 |
| 84 | 5.55 |
| 85 | 5.39 |
| 86 | 6.27 |
| 87 | 5.54 |
| 88 | 5.81 |
| 89 | 5.99 |
| 90 | 5.99 |
| 91 | 5.29 |
| 92 | 5.95 |
| 93 | 6.96 |
| 94 | 5.26 |
| 95 | NT |
| 96 | 6.07 |
| 97 | 5.81 |
| 98 | 4.84 |
| 99 | NT |
| 100 | NT |
| 101 | NT |
| 102 | 6.11 |
| 103 | 6.10 |
| 104 | 6.78 |
| 105 | 5.27 |
| 106 | 6.23 |
| 107 | 5.56 |
| 108 | 5.36 |
| 109 | 5.49 |
| 112 | 5.36 |
| 113 | 5.57 |
| 114 | 5.79 |
| 115 | 5.82 |
| 116 | 5.52 |
| 117 | 5.19 |
| 118 | 6.17 |
| 119 | 6.48 |
| 120 | 6.07 |
| 121 | 5.95 |
| 122 | 5.43 |
| 123 | 5.66 |
| 124 | 5.67 |
| 125 | 7.72 |
| 126 | 7.26 |
| 127 | 6.68 |

NT means not tested.

Example C Inhibition of ConA Induced Hepatitis

Orally administer compound into normal C57/BL6 mice at several doses. After 1 hr, inject i.v. with ConA 15 mg/kg, (N=5). Post 8-24 hrs, collect plasma and liver. Measure plasma ALT enzyme level. An $ED_{50}$ is determined as the amount of test compound that reduces ConA induced increase in plasma ALT level by 50%.

In the assay of Example C, the compound of Example 86 gave $ED_{50}=5$ mg/kg.

What is claimed is:
1. A compound of the formula:

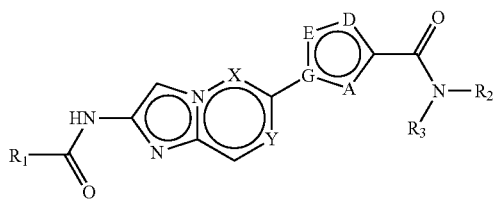

or a pharmaceutically acceptable salt thereof, wherein
$R_1$ is selected from the group consisting of optionally substituted $C_{1-4}$ alkyl and optionally substituted $C_{3-8}$ cycloalkyl;
$R_2$ is selected from the group consisting of hydrogen and optionally substituted $C_{1-4}$ alkyl;
$R_3$ is selected from the group consisting of substituted $C_{1-6}$ alkyl, optionally substituted $C_{3-8}$ cycloalkyl, and optionally substituted $C_{3-6}$ heterocyclyl;
or
$R_2$ and $R_3$ together with the nitrogen to which they are attached form a 4 to 6 membered, saturated ring optionally having an additional ring heteroatom selected from the group N, O, and S and optionally substituted on any ring carbon with 1 to 5 substituents independently selected from the group consisting of cyano, halo, hydroxy, amino, $C_{1-9}$ amide, $C_{1-4}$ alkyl, $C_{1-4}$ alkoxy, hydroxymethyl, and trifluoromethyl and optionally substituted on any optional additional ring nitrogen by optionally substituted $C_{1-4}$ alkyl;
X and Y are independently selected from the group consisting of N and $CR_4$;
$R_4$, each time taken, is independently selected from the group consisting of hydrogen, cyano, halo, hydroxy, $C_{1-2}$ alkyl, $C_{1-2}$ alkoxy, and trifluoromethyl;
G is carbon;
A is selected from the group consisting of N, O, S, $CR_5$ and $NR_6$;
D is selected from the group consisting of N, O, S, $CR_5$ and $NR_6$;
E is selected from the group consisting of N, O, S, $CR_5$ and $NR_6$;
provided that only one of A, D, and E can be O or S;
or G is N when A, D, and E are $CR_5$;
or G is N when one of A, D, or E is N and the others of A, D, and E are $CR_5$;
or G is N when two of A, D, or E are N and the other of A, D, and E is $CR_5$;
$R_5$, each time taken, is independently selected from the group consisting of hydrogen, cyano, halo, $C_{1-4}$ alkyl, $C_{1-4}$ alkoxy, and trifluoromethyl; and
$R_6$ is selected from the group consisting of hydrogen and $C_{1-4}$ alkyl.

2. The compound or pharmaceutically acceptable salt according to claim 1, wherein $R_3$ is substituted $C_{1-6}$ alkyl.

3. The compound or pharmaceutically acceptable salt according to claim 1, wherein $R_3$ is $C_{1-4}$ alkyl substituted with 1 to 6 fluorines.

4. The compound or pharmaceutically acceptable salt according to claim 1, wherein $R_2$ optionally substituted $C_{1-4}$ alkyl.

5. The compound or pharmaceutically acceptable salt according to claim 1, wherein $R_1$ is $C_{3-8}$ cycloalkyl.

6. The compound or pharmaceutically acceptable salt according to claim 1, wherein $R_1$ is cyclopropyl.

7. The compound or pharmaceutically acceptable salt according to claim 1, wherein A is $CR_5$, D is S, E is $CR_5$, and G is carbon.

8. The compound or pharmaceutically acceptable salt according to claim 1, wherein A is $CR_5$, D is $NR_6$, E is N, and G is carbon.

9. The compound or pharmaceutically acceptable salt according to claim 1, wherein A is N, D is S, E is $CR_5$, and G is carbon.

10. The compound or pharmaceutically acceptable salt according to claim 1, wherein X and Y are $CR_4$ and each $R_4$ is hydrogen.

11. The compound or pharmaceutically acceptable salt according to claim 1, wherein X is N and Y is $CR_4$ and each $R_4$ is hydrogen.

12. The compound or pharmaceutically acceptable salt according to claim 1, wherein Y is N and X is $CR_4$ and each $R_4$ is hydrogen.

13. The compound according to claim 1, which is selected from the group consisting of:
   3-(2-(cyclopropanecarboxamido)imidazo[1,2-a]pyridin-6-yl)-1-methyl-N-(2,2,2-trifluoroethyl)-1H-pyrazole-5-carboxamide;
   3-(2-(cyclopropanecarboxamido)imidazo[1,2-a]pyridin-6-yl)-N-(2,2-difluoroethyl)-1-methyl-1H-pyrazole-5-carboxamide;
   4-(2-(cyclopropanecarboxamido)imidazo[1,2-a]pyridin-6-yl)-N-(2,2-difluoropropyl)thiophene-2-carboxamide;
   4-(2-(cyclopropanecarboxamido)imidazo[1,2-a]pyridin-6-yl)-N-(2,2,2-trifluoroethyl)thiazole-2-carboxamide;
   4-(2-(cyclopropanecarboxamido)imidazo[1,2-a]pyrazin-6-yl)-N-(2,2-difluoroethyl)thiazole-2-carboxamide;
   4-(2-(cyclopropanecarboxamido)imidazo[1,2-a]pyrazin-6-yl)-N-(2,2,2-trifluoroethyl)thiazole-2-carboxamide;
   (R)-4-(2-(cyclopropanecarboxamido)imidazo[1,2-a]pyrazin-6-yl)-N-(1,1,1-trifluoropropan-2-yl)thiazole-2-carboxamide;
   4-(2-(cyclopropanecarboxamido)imidazo[1,2-b]pyridazin-6-yl)-N-(2,2-difluoroethyl)thiazole-2-carboxamide;
   4-{2-cyclopropaneamidoimidazo[1,2-a]pyridin-6-yl}-N-[(2R)-1,1,1-trifluoropropan-2-yl]-1H-imidazole-2-carboxamide;
   4-{2-cyclopropaneamidoimidazo[1,2-a]pyridin-6-yl}-N-[(2S)-1,1,1-trifluoropropan-2-yl]-1H-imidazole-2-carboxamide;
   4-{2-cyclopropaneamidoimidazo[1,2-a]pyridin-6-yl}-N-(2,2-difluoropropyl)-1H-imidazole-2-carboxamide;
   4-{2-cyclopropaneamidoimidazo[1,2-a]pyridin-6-yl}-N-(2,2-difluoroethyl)-1H-imidazole-2-carboxamide;
   4-(2-acetamidoimidazo[1,2-a]pyridin-6-yl)-N-(2,2,2-trifluoroethyl)thiophene-2-carboxamide;
   4-(2-(2-methoxyacetamido)imidazo[1,2-a]pyridin-6-yl)-N-(2,2,2-trifluoroethyl)thiophene-2-carboxamide;
   4-(2-(3-methoxypropanamido)imidazo[1,2-a]pyridin-6-yl)-N-(2,2,2-trifluoroethyl)thiophene-2-carboxamide;
   4-(2-(2-fluoroacetamido)imidazo[1,2-a]pyridin-6-yl)-N-(2,2,2-trifluoroethyl)thiophene-2-carboxamide;
   4-(2-(2-cyanoacetamido)imidazo[1,2-a]pyridin-6-yl)-N-(2,2,2-trifluoroethyl)thiophene-2-carboxamide;

4-(2-(cyclopropanecarboxamido)imidazo[1,2-b]
pyridazin-6-yl)-N-(2,2-difluoroethyl)thiophene-2-car-
boxamide;
4-(2-(cyclopropanecarboxamido)imidazo[1,2-a]pyrazin-
6-yl)-N-(2,2-difluoroethyl)thiophene-2-carboxamide;
4-(2-(cyclopropanecarboxamido)imidazo[1,2-b]
pyridazin-6-yl)-5-methyl-N-(2,2,2-trifluoroethyl)thiaz-
ole-2-carboxamide;
4-(2-(cyclopropanecarboxamido)imidazo[1,2-b]
pyridazin-6-yl)-N-(2,2,2-trifluoroethyl)thiazole-2-car-
boxamide;
5-(2-(cyclopropanecarboxamido)imidazo[1,2-a]pyridin-
6-yl)-N-(2,2,2-trifluoroethyl)thiazole-2-carboxamide;
4-(2-(cyclopropanecarboxamido)imidazo[1,2-b]
pyridazin-6-yl)-5-methyl-N-(2,2,2-trifluoroethyl)thio-
phene-2-carboxamide;
4-(2-(cyclopropanecarboxamido)imidazo[1,2-a]pyridin-
6-yl)-N-(1,1,1-trifluoropropan-2-yl)-1H-imidazole-2-
carboxamide;
3-(2-(cyclopropanecarboxamido)imidazo[1,2-a]pyridin-
6-yl)-4-methyl-N-(2,2,2-trifluoroethyl)-1H-pyrazole-
5-carboxamide;
5-(2-(cyclopropanecarboxamido)imidazo[1,2-a]pyridin-
6-yl)-N-(2,2-difluoroethyl)-1H-pyrazole-3-carboxam-
ide;
5-(2-(cyclopropanecarboxamido)imidazo[1,2-a]pyridin-
6-yl)-N-(2,2,2-trifluoroethyl)isothiazole-3-carboxam-
ide;
4-(2-(cyclopropanecarboxamido)imidazo[1,2-a]pyridin-
6-yl)-N-methyl-N-(2,2,2-trifluoroethyl)thiophene-2-
carboxamide;
4-(2-(cyclopropanecarboxamido)imidazo[1,2-a]pyridin-
6-yl)-5-methyl-N-(2,2,2-trifluoroethyl)thiophene-2-
carboxamide;
4-(2-(cyclopropanecarboxamido)imidazo[1,2-a]pyrazin-
6-yl)-5-methyl-N-(2,2,2-trifluoroethyl)thiophene-2-
carboxamide;
4-(2-(cyclopropanecarboxamido)imidazo[1,2-a]pyridin-
6-yl)-5-methyl-N-(2,2,2-trifluoroethyl)thiazole-2-car-
boxamide;
4-(2-(cyclopropanecarboxamido)imidazo[1,2-a]pyridin-
6-yl)-N-(2,2,2-trifluoroethyl)thiophene-2-carboxam-
ide;
4-(2-(cyclopropanecarboxamido)imidazo[1,2-a]pyrazin-
6-yl)-N-(2,2,2-trifluoroethyl)thiophene-2-carboxam-
ide;
1-(2-(cyclopropanecarboxamido)imidazo[1,2-a]pyridin-
6-yl)-N-(2,2,2-trifluoroethyl)-1H-pyrazole-3-carbox-
amide;
1-(2-(cyclopropanecarboxamido)imidazo[1,2-a]pyridin-
6-yl)-N-(2,2-difluoroethyl)-1H-pyrazole-3-carboxam-
ide;
1-(2-(cyclopropanecarboxamido)imidazo[1,2-a]pyrazin-
6-yl)-N-(2,2,2-trifluoroethyl)-1H-pyrazole-3-carbox-
amide;
1-(2-(cyclopropanecarboxamido)imidazo[1,2-b]
pyridazin-6-yl)-N-(2,2-difluoroethyl)-1H-pyrazole-3-
carboxamide;
1-(2-(cyclopropanecarboxamido)imidazo[1,2-a]pyrazin-
6-yl)-N-(2,2-difluoroethyl)-1H-pyrazole-3-carboxam-
ide;
1-(2-(cyclopropanecarboxamido)imidazo[1,2-b]
pyridazin-6-yl)-N-(2,2,2-trifluoroethyl)-1H-pyrazole-
3-carboxamide;
1-(2-(cyclopropanecarboxamido)imidazo[1,2-a]pyridin-
6-yl)-N-(2,2,2-trifluoroethyl)-1H-pyrazole-4-carbox-
amide;
1-(2-(cyclopropanecarboxamido)imidazo[1,2-a]pyridin-
6-yl)-N-(2,2,2-trifluoroethyl)-1H-imidazole-4-carbox-
amide;
1-(2-(cyclopropanecarboxamido)imidazo[1,2-a]pyridin-
6-yl)-N-(2,2-difluoropropyl)-1H-imidazole-4-carbox-
amide;
(R)-1-(2-cyclopropanecarboxamido)imidazol[1,2-a]pyri-
dine-6-yl)-N-(1,1,1-trifluoropropan-2-yl)-1H-imida-
zole-4-caboxamide;
4-(2-(cyclopropanecarboxamido)imidazo[1,2-b]
pyridazin-6-yl)-N-(2,2,2-trifluoroethyl)thiophene-2-
carboxamide;
4-(2-(cyclopropanecarboxamido)imidazo[1,2-a]pyrazin-
6-yl)-N-((1R,2S)-2-hydroxycyclohexyl)thiazole-2-car-
boxamide;
4-(2-(cyclopropanecarboxamido)imidazo[1,2-a]pyrazin-
6-yl)-N-(4-hydroxytetrahydrofuran-3-yl)thiazole-2-
carboxamide;
(S)-N-(6-(2-(2-(trifluoromethyl)pyrrolidine-1-carbonyl)
thiazol-4-yl)imidazo[1,2-a]pyrazin-2-yl)cyclopropan-
ecarboxamide;
(R)-4-(2-(cyclopropanecarboxamido)imidazo[1,2-a]
pyrazin-6-yl)-N-(tetrahydro-2H-pyran-3-yl)thiazole-2-
carboxamide;
(R)-4-(2-(cyclopropanecarboxamido)imidazo[1,2-a]
pyrazin-6-yl)-N-(tetrahydrofuran-3-yl)thiazole-2-car-
boxamide;
4-(2-(cyclopropanecarboxamido)imidazo[1,2-a]pyridin-
6-yl)-N-(2,2,2-trifluoroethyl)-1H-imidazole-2-carbox-
amide;
5-(2-(cyclopropanecarboxamido)imidazo[1,2-a]pyridin-
6-yl)-N-(2,2,2-trifluoroethyl)-1H-pyrazole-3-carbox-
amide;
(R)-N-(6-(3-(2-(trifluoromethyl)pyrrolidine-1-carbonyl)-
1H-pyrazol-5-yl)imidazo[1,2-a]pyridin-2-yl)cyclopro-
panecarboxamide;
(S)-5-(2-(cyclopropanecarboxamido)imidazo[1,2-a]pyri-
din-6-yl)-N-(tetrahydrofuran-3-yl)-1H-pyrazole-3-car-
boxamide;
N-{6-[5-(morpholine-4-carbonyl)thiophen-3-yl]imidazo
[1,2-a]pyridin-2-yl}cyclopropanecarboxamide;
4-(2-(cyclopropanecarboxamido)imidazo[1,2-a]pyridin-
6-yl)-N-(2,2-difluoroethyl)thiophene-2-carboxamide;
4-(2-(cyclopropanecarboxamido)imidazo[1,2-a]pyridin-
6-yl)-N-(1,1,1-trifluoro-2-methylpropan-2-yl)thio-
phene-2-carboxamide;
4-(2-(cyclopropanecarboxamido)imidazo[1,2-a]pyridin-
6-yl)-N-(2,2-difluoropropyl)thiophene-2-carboxamide;
N-(6-(5-(4-methoxypiperidine-1-carbonyl)thiophen-3-yl)
imidazo[1,2-a]pyridin-2-yl)cyclopropanecarboxamide;
4-(2-(cyclopropanecarboxamido)imidazo[1,2-a]pyridin-
6-yl)-N-(1,1,1-trifluoropropan-2-yl)thiophene-2-car-
boxamide;
N-(6-(5-(2-(trifluoromethyl)pyrrolidine-1-carbonyl)thio-
phen-3-yl)imidazo[1,2-a]pyridin-2-yl)cyclopropan-
ecarboxamide;
(S)-N-(6-(5-(2-(trifluoromethyl)pyrrolidine-1-carbonyl)
thiophen-3-yl)imidazo[1,2-a]pyridin-2-yl)cyclopro-
panecarboxamide;
(R)-N-(6-(5-(2-(trifluoromethyl)pyrrolidine-1-carbonyl)
thiophen-3-yl)imidazo[1,2-a]pyridin-2-yl)cyclopro-
panecarboxamide;
4-(2-(cyclopropanecarboxamido)imidazo[1,2-a]pyridin-
6-yl)-N-isobutylthiophene-2-carboxamide;
4-(2-(cyclopropanecarboxamido)imidazo[1,2-a]pyridin-
6-yl)-N-(2-fluoroethyl)thiophene-2-carboxamide;

4-(2-(cyclopropanecarboxamido)imidazo[1,2-a]pyridin-6-yl)-N-(2-fluoroethyl)thiophene-2-carboxamide;
4-(2-(cyclopropanecarboxamido)imidazo[1,2-a]pyridin-6-yl)-N-(tetrahydro-2H-pyran-4-yl)thiophene-2-carboxamide;
4-(2-(cyclopropanecarboxamido)imidazo[1,2-a]pyridin-6-yl)-N-(tetrahydro-2H-pyran-3-yl)thiophene-2-carboxamide;
(S)-4-(2-(cyclopropanecarboxamido)imidazo[1,2-a]pyridin-6-yl)-N-(tetrahydro-2H-pyran-3-yl)thiophene-2-carboxamide;
(R)-4-(2-(cyclopropanecarboxamido)imidazo[1,2-a]pyridin-6-yl)-N-(tetrahydro-2H-pyran-3-yl)thiophene-2-carboxamide;
4-(2-(cyclopropanecarboxamido)imidazo[1,2-a]pyridin-6-yl)-N-(tetrahydrofuran-3-yl)thiophene-2-carboxamide;
(R)-4-(2-(cyclopropanecarboxamido)imidazo[1,2-a]pyridin-6-yl)-N-(tetrahydrofuran-3-yl)thiophene-2-carboxamide;
(S)-4-(2-(cyclopropanecarboxamido)imidazo[1,2-a]pyridin-6-yl)-N-(tetrahydrofuran-3-yl)thiophene-2-carboxamide;
4-(2-(cyclopropanecarboxamido)imidazo[1,2-a]pyridin-6-yl)-N-(2-methoxyethyl)thiophene-2-carboxamide;
N-(6-(5-(3,3-difluoropyrrolidine-1-carbonyl)thiophen-3-yl)imidazo[1,2-a]pyridin-2-yl)cyclopropanecarboxamide;
4-(2-(cyclopropanecarboxamido)imidazo[1,2-a]pyridin-6-yl)-N-((tetrahydrofuran-3-yl)methyl)thiophene-2-carboxamide;
4-(2-(cyclopropanecarboxamido)imidazo[1,2-a]pyridin-6-yl)-N-((1S,2R)-2-hydroxycyclohexyl)thiophene-2-carboxamide;
N-(6-(5-(3,3-difluoroazetidine-1-carbonyl)thiophen-3-yl)imidazo[1,2-a]pyridin-2-yl)cyclopropanecarboxamide;
4-(2-(cyclopropanecarboxamido)imidazo[1,2-a]pyridin-6-yl)-N-(3,3,3-trifluoropropyl)thiophene-2-carboxamide;
N-(1-acetylpyrrolidin-3-yl)-4-(2-(cyclopropanecarboxamido)imidazo[1,2-a]pyridin-6-yl)thiophene-2-carboxamide;
(S)-4-(2-(cyclopropanecarboxamido)imidazo[1,2-a]pyridin-6-yl)-N-(1,1,1-trifluoropropan-2-yl)thiophene-2-carboxamide;
(R)-4-(2-(cyclopropanecarboxamido)imidazo[1,2-a]pyridin-6-yl)-N-(1,1,1-trifluoropropan-2-yl)thiophene-2-carboxamide;
(S)-1-(4-(2-(cyclopropanecarboxamido)imidazo[1,2-a]pyridin-6-yl)thiophene-2-carbonyl)-4,4-difluoropyrrolidine-2-carboxamide;
4-(2-(cyclopropanecarboxamido)imidazo[1,2-a]pyridin-6-yl)-N-(2-methoxyethyl)-N-(2,2,2-trifluoroethyl)thiophene-2-carboxamide;
4-(2-(cyclopropanecarboxamido)imidazo[1,2-a]pyridin-6-yl)-N-(4-hydroxytetrahydrofuran-3-yl)thiophene-2-carboxamide;
4-(2-(cyclopropanecarboxamido)imidazo[1,2-a]pyridin-6-yl)-N-(2-oxocyclopentyl)thiophene-2-carboxamide;
4-(2-(cyclopropanecarboxamido)imidazo[1,2-a]pyridin-6-yl)-N-(2,2-difluoroethyl)thiazole-2-carboxamide;
(S)-4-(2-(cyclopropanecarboxamido)imidazo[1,2-a]pyridin-6-yl)-N-(tetrahydrofuran-3-yl)thiazole-2-carboxamide;
(S)-4-(2-(cyclopropanecarboxamido)imidazo[1,2-a]pyridin-6-yl)-N-(tetrahydro-2H-pyran-3-yl)thiazole-2-carboxamide;
4-(2-(cyclopropanecarboxamido)imidazo[1,2-a]pyridin-6-yl)-N-((1S,2R)-2-hydroxycyclopentyl)thiazole-2-carboxamide;
4-(2-(cyclopropanecarboxamido)imidazo[1,2-a]pyridin-6-yl)-N-(2,2-difluorocyclopentyl)thiazole-2-carboxamide;
4-(2-(cyclopropanecarboxamido)imidazo[1,2-a]pyridin-6-yl)-N-(2-oxocyclopentyl)thiazole-2-carboxamide;
4-(2-(cyclopropanecarboxamido)imidazo[1,2-a]pyridin-6-yl)-N-(3,3,3-trifluoropropyl)thiazole-2-carboxamide;
(R)-N-(6-(2-(2-(trifluoromethyl)pyrrolidine-1-carbonyl)thiazol-4-yl)imidazo[1,2-a]pyridin-2-yl)cyclopropanecarboxamide;
4-(2-(cyclopropanecarboxamido)imidazo[1,2-a]pyridin-6-yl)-N-(2-oxotetrahydrofuran-3-yl)thiazole-2-carboxamide;
4-(2-(cyclopropanecarboxamido)imidazo[1,2-a]pyridin-6-yl)-N-(2-hydroxyethyl)thiazole-2-carboxamide;
(S)-N-(6-(2-(4,4-difluoro-2-(hydroxymethyl)pyrrolidine-1-carbonyl)thiazol-4-yl)imidazo[1,2-a]pyridin-2-yl)cyclopropanecarboxamide;
N-(6-(2-(3-methoxypyrrolidine-1-carbonyl)thiazol-4-yl)imidazo[1,2-a]pyridin-2-yl)cyclopropanecarboxamide;
1-(4-(2-(cyclopropanecarboxamido)imidazo[1,2-a]pyridin-6-yl)thiazole-2-carbonyl)pyrrolidine-3-carboxamide;
4-(2-(cyclopropanecarboxamido)imidazo[1,2-a]pyridin-6-yl)-N-(5-oxopyrrolidin-3-yl)thiazole-2-carboxamide;
N-(6-(2-(3-(hydroxymethyl)pyrrolidine-1-carbonyl)thiazol-4-yl)imidazo[1,2-a]pyridin-2-yl)cyclopropanecarboxamide;
N-(6-(2-(3-methoxyazetidine-1-carbonyl)thiazol-4-yl)imidazo[1,2-a]pyridin-2-yl)cyclopropanecarboxamide;
N-(6-(2-(3-cyanoazetidine-1-carbonyl)thiazol-4-yl)imidazo[1,2-a]pyridin-2-yl)cyclopropanecarboxamide;
N-(6-(2-(3-methylpyrrolidine-1-carbonyl)thiazol-4-yl)imidazo[1,2-a]pyridin-2-yl)cyclopropanecarboxamide;
(R)-3-(2-(cyclopropanecarboxamido)imidazo[1,2-a]pyridin-6-yl)-N-(1,1,1-trifluoropropan-2-yl)-1H-pyrazole-5-carboxamide;
N-(6-(5-(4-fluoropiperidine-1-carbonyl)-1H-pyrazol-3-yl)imidazo[1,2-a]pyridin-2-yl)cyclopropanecarboxamide;
3-(2-(cyclopropanecarboxamido)imidazo[1,2-a]pyridin-6-yl)-N-methyl-N-(2,2,2-trifluoroethyl)-1H-pyrazole-5-carboxamide;
N-(6-(5-(3-fluoropyrrolidine-1-carbonyl)-1H-pyrazol-3-yl)imidazo[1,2-a]pyridin-2-yl)cyclopropanecarboxamide;
4-(2-(cyclopropanecarboxamido)imidazo[1,2-a]pyridin-6-yl)-N-(4-hydroxytetrahydrofuran-3-yl)thiazole-2-carboxamide;
N-(6-(2-(3-hydroxypyrrolidine-1-carbonyl)thiazol-4-yl)imidazo[1,2-a]pyridin-2-yl)cyclopropanecarboxamide;
4-(2-(cyclopropanecarboxamido)imidazo[1,2-a]pyridin-6-yl)-N-((3S,4S)-4-hydroxytetrahydrofuran-3-yl)thiazole-2-carboxamide;
N-(6-(2-(3-hydroxyazetidine-1-carbonyl)thiazol-4-yl)imidazo[1,2-a]pyridin-2-yl)cyclopropanecarboxamide;
N-(6-(2-(2-(hydroxymethyl)pyrrolidine-1-carbonyl)thiazol-4-yl)imidazo[1,2-a]pyridin-2-yl)cyclopropanecarboxamide;
4-(2-(cyclopropanecarboxamido)imidazo[1,2-a]pyridin-6-yl)-N-(3,3,3-trifluoro-2-hydroxypropyl)thiazole-2-carboxamide;

5-(2-(cyclopropanecarboxamido)imidazo[1,2-a]pyridin-6-yl)-N-(2,2-difluoroethyl)-1H-pyrazole-3-carboxamide;

4-(2-(cyclopropanecarboxamido)imidazo[1,2-a]pyridin-6-yl)-N-(1,1,1-trifluoro-3-methylbutan-2-yl)thiophene-2-carboxamide;

4-(2-(cyclopropanecarboxamido)imidazo[1,2-a]pyridin-6-yl)-N-(1-(trifluoromethyl)cyclopropyl)thiophene-2-carboxamide;

4-(2-(cyclopropanecarboxamido)imidazo[1,2-a]pyridin-6-yl)-N-(3-hydroxypropyl)-N-(2,2,2-trifluoroethyl)thiophene-2-carboxamide;

4-(2-(cyclopropanecarboxamido)imidazo[1,2-a]pyridin-6-yl)-N-(2-hydroxyethyl)-N-(2,2,2-trifluoroethyl)thiophene-2-carboxamide;

4-(2-(cyclopropanecarboxamido)imidazo[1,2-a]pyridin-6-yl)-N-(2,2-difluoroethyl)-N-(2-methoxyethyl)thiophene-2-carboxamide;

4-(2-(cyclopropanecarboxamido)imidazo[1,2-a]pyridin-6-yl)-N-(oxetan-3-yl)thiazole-2-carboxamide;

N-(6-(5-(2-methylpyrrolidine-1-carbonyl)-1H-pyrazol-3-yl)imidazo[1,2-a]pyridin-2-yl)cyclopropanecarboxamide;

N-(6-(2-(3-(hydroxymethyl)azetidine-1-carbonyl)thiazol-4-yl)imidazo[1,2-a]pyridin-2-yl)cyclopropanecarboxamide;

N-((1R,6R)-6-amino-2,2-difluorocyclohexyl)-4-(2-(cyclopropanecarboxamido)imidazo[1,2-a]pyridin-6-yl)thiophene-2-carboxamide;

N-((1R,6S)-6-amino-2,2-difluorocyclohexyl)-4-(2-(cyclopropanecarboxamido)imidazo[1,2-a]pyridin-6-yl)thiophene-2-carboxamide; and 1-(2-(cyclopropanecarboxamido)imidazo[1,2-a]pyrazin-6-yl)-N-(2-hydroxyethyl)-N-(2,2,2-trifluoroethyl)-1H-pyrazole-3-carboxamide;

or a pharmaceutically acceptable salt of any one of the above-mentioned compounds.

14. A pharmaceutical composition comprising a compound or pharmaceutically acceptable salt as defined in claim 1, and a pharmaceutically acceptable excipient.

15. A method of inhibiting TBK1 in a patient, the method comprising administering to the patient a compound or pharmaceutical salt as defined in claim 1, wherein the patient is suffering from a condition selected from autoimmune disorders, inflammatory disorders, fibrotic conditions, cancer and sepsis.

\* \* \* \* \*